US006284240B1

(12) United States Patent (10) Patent No.: US 6,284,240 B1
Seed et al. (45) Date of Patent: Sep. 4, 2001

(54) TARGETED CYTOLYSIS OF HIV-INFECTED CELLS BY CHIMERIC CD4 RECEPTOR-BEARING CELLS

(75) Inventors: Brian Seed; Babak Banapour, both of Boston; Charles Romeo, Belmont; Waldemar Kolanus, Watertown, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/218,950

(22) Filed: Dec. 22, 1998

Related U.S. Application Data

(60) Division of application No. 08/284,391, filed on Aug. 2, 1994, now Pat. No. 5,851,828, which is a continuation-in-part of application No. 08/195,395, filed on Feb. 14, 1994, now abandoned, which is a continuation-in-part of application No. 07/847,566, filed on Mar. 6, 1992, now abandoned, which is a continuation-in-part of application No. 07/665,961, filed on Mar. 7, 1991, now abandoned.

(51) Int. Cl.[7] .................................................... A61K 48/00

(52) U.S. Cl. ....................... 424/93.21; 424/93.2

(58) Field of Search ................................ 424/93.21, 93.2

(56) References Cited

U.S. PATENT DOCUMENTS

| | | |
|---|---|---|
| 4,690,915 | 9/1987 | Rosenburg . |
| 4,946,778 | 8/1990 | Ladner et al. . |
| 5,030,576 | 7/1991 | Dull et al. . |
| 5,091,513 | 2/1992 | Huston et al. . |
| 5,225,538 | 7/1993 | Capon et al. . |
| 5,336,603 | 8/1994 | Capon et al. . |
| 5,359,046 | 10/1994 | Capon et al. . |
| 5,439,819 | 8/1995 | Littman et al. . |
| 5,504,000 | 4/1996 | Littman et al. . |
| 5,686,281 | 11/1997 | Roberts . |
| 5,712,149 | 1/1998 | Roberts . |
| 5,851,828 | * 12/1998 | Seed et al. ........................... 435/328 |

FOREIGN PATENT DOCUMENTS

| | | |
|---|---|---|
| 180878 | 5/1986 | (EP) . |
| 0 314 317 | 5/1989 | (EP) . |
| 0 325 262 | 6/1989 | (EP) . |
| 340793 | 11/1989 | (EP) . |
| 0 394 827 | 10/1990 | (EP) . |
| 394827 | 10/1990 | (EP) . |
| 10-63394 | 3/1989 | (JP) . |
| 224379 | 12/1990 | (NL) . |
| 92/15322 | 9/1962 | (WO) . |
| 86/01533 | 3/1986 | (WO) . |
| 88/01649 | 3/1988 | (WO) . |
| 90/04640 | 5/1990 | (WO) . |
| 90/11360 | 10/1990 | (WO) . |
| 91/10736 | 7/1991 | (WO) . |
| 92/10591 | 6/1992 | (WO) . |
| 93/19163 | 9/1993 | (WO) . |
| WO 95/02686 | 1/1995 | (WO) . |
| 95/21528 | 8/1995 | (WO) . |
| WO 96/26265 | 8/1996 | (WO) . |

OTHER PUBLICATIONS

Anderson et al., "Fc Receptor Type III (CD16) is included in the NK Receptor Complex Expressed by Human Natural Killer Cells;" Proc. Natl. Acad. Sci. USA, 87:2274–2278, 1990.

Anderson et al., "CD3–Negative Natural Killer Cells Express TCR as part of a Novel Molecule Complex;" Nature 341:159–162, 1989.

Aruffo et al., "Molecular Cloning of a CD28 cDNA by a High–Efficiency COS Cell Expression System;" Proc. Natl. Sci. USA 84:8573–8577, 1987.

Becker et al., "Messenger RNA in Cells Infected with Vaccinia Virus;" Biochemistry 51:577–585, 1964.

Becker et al., "Expression of a Hybrid Immunoglobulin–T Cell Receptor Protein in Transgenic Mice;" 58:911–921, 1989.

Berke et al., "T Lymphocyte–Mediated Cytolisys—A Comprehensive Theory I. The Mechanism of CTL–Mediated Cytolysis;" Mechanism of Cell Mediated Cytotoxicity 57–73, 1982.

Berke, "Cytotoxic T–Lymphocytes—How Do They Function?;" Immunological Rev. 72:5–42, 1983.

Berke, "Lymphocyte–Triggered Internal Target Disintegration;" Immunology Today 12:396–399, 1991.

Berkhout et al., "Transfection of Genes Encoding the T Cell Receptor–associated CD3 Complex into COS Cells Results in Assembly of the Macromolecular Structure;" The Journal of Biological Chemistry 263:8528–8536, 1988.

Blank et al., "Complete Structure and Expression in Transfected Cells of High Affinity IgE Receptor;" Nature 337:187–189, 1989.

Blumberg et al., "Antibody–Dependent Cell–Mediated Cytotoxicity Against Cells Infected with the Human Immunodeficiency Virus;" The Journal of Infectious Diseases 156:878–883, 1987.

Boyle et al., "A Dominant Selectable Marker for the Construction Recombinant Poxviruses;" Gene 65:123–128, 1988.

(List continued on next page.)

*Primary Examiner*—Robert D. Budens
(74) *Attorney, Agent, or Firm*—Clark & Elbing LLP

(57) ABSTRACT

Disclosed is a method of directing a cellular immune response against an HIV-infected cell in a mammal involving administering to the mammal an effective amount of therapeutic cells which express a membrane-bound, proteinaceous chimeric receptor comprising (a) an extracellular portion which includes a fragment of CD4 which is capable of specifically recognizing and binding the HIV-infected cell but which does not mediate HIV infection and (b) an intracellular portion which is capable of signalling the therapeutic cell to destroy the receptor-bound HIV-infected cell. Also disclosed are cells which express the chimeric receptors and DNA and vectors encoding the chimeric receptors.

13 Claims, 28 Drawing Sheets

OTHER PUBLICATIONS

Buonocore et al., "Prevention of HIV–1 Glycoprotein Transport by Soluble CD4 Retained in the Endoplasmic Reticulum;" Nature 345:625–628, 1990.

Byrn et al., "Biological Properties of a CD4 Immunoadhesin;" Nature 344:667–670, 1990.

Capon et al., "Designing CD4 Immunoadhesins for AIDS Therapy;" Nature 337:525–531, 1989.

Carr et al., "Protein and Carbohydrate Structural Analysis of a Recombinant Soluble CD4 Receptor by Mass Spectrometry;" The Journal of Biological Chemistry 264:21286–21295, 1989.

Chakrabarti et al., "Expression of HTLV–III Envelope Gene by a Recombinant Vaccinia Virus;" Nature 320:535–537, 1986.

Chaudhary et al., "Selective Killing of HIV–Infected Cells by Recombinant Human CD4–Pseudomonas Extoxin Hybrid Protein;" Nature 335:369–372, 1988.

Chan et al., "ZAP–70: A 70 kd Protein–Tyrosine Kinase that Associates with the TCR Chain;" Cell 71:649–662, 1992.

Clark et al., "T Lymphocyte–Mediated Cytolysis—A Comprehensive Theory II Lytic vs Nonlytic Interactions of T Lymphocytes;" 69–73.

Clayton et al., "Characterization of Thymus–derived Lymphocytes Expressing Tiα–βCD3δε– or Tiα–βCD3δε–1– Antigen Receptor Isoforms . . . ;" Rockefeller Univ. Press 172:1243–1253, 1990.

Cline, "Gene Therapy: Current Status and Future Directions;" Schweiz. Med. Wschr. 116:1459–1464, 1986.

Dalgleish et al., "The CD4 (T4) Antigen is an Essential Component of the Receptor for the AIDS Retrovirus;" Nature 312:763–767, 1984.

Deen et al., "A Soluble Form of CD4(T4) Protein Inhibits AIDS Virus Infection;" Nature 331:82–84, 1988.

Denny et al., "A Chromosome 14 Inversion in a T–Cell Lymphoma is caused by Site–Specific Recombination between Immunoglobulin and T–Cell Receptor Loci;" Nature 320:549–551, 1986.

Doyle et al., "Interaction between CD4 and Class II MHC Molecules Mediates Cell Adhesion;" Nature 330:256–259, 1987.

Earl et al., "Removal of Cryptic Poxvirus Transcription Termination Signals from the Human Immunodeficiency Virus Type 1 Envelope Gene Enhances Expression and Immunogenicity . . . ;" Journal of Virology 64:2448–2451, 1990.

Falkner et al., "*Escherichia coli* gpt Gene Provides Dominant Selection for Vaccinia Virus Open Reading Frame Expression Vectors;" Journal of Virology 62:1849–1854, 1988.

Fanger et al., "Cytotoxicity Mediated by Human Fc Receptors for IgG;" Elsevier Science Publishers Ltd. 92–99, 1989.

Fisher et al., "HIV Infection is Blocked in vitro by Recombinant Soluble CD4;" Nature 331:76–78, 1988.

Frank et al., "Structural Mutations of the T Cell Receptor Chain and its Role in T Cell Activation;" Science 249:174–177, 1990.

Friedman et al., "Expression of a truncated viral trans–activator selectively impedes lytic infection by its cognate virus;" Nature 335:452–454, 1988.

Grynkiewicz et al., "A New Generation of $Ca^{2+}$ Indicators with Greatly Improved Fluorescence Properties;" The Journal of Biological Chemistry 260:3440–3450, 1985.

Gauen et al., "$_p59^{fyn}$ Tyrosine Kinase Associates with Multiple T–Cell Receptor Subunits through its Unique Amino––Terminal Domain;" Molecular and Cellular Biology 12:5438–5446, 1992.

Gay et al., "Functional Interaction Between Human T–Cell Protein CD4 and the major Histocompatibility Complex HLA–DR Antigen;" Nature 328:626–629, 1987.

Goverman et al., "Chimeric Immunoglobulin–T Cell Receptor Proteins Form Functional Receptors: Implications for T Cell Receptor Complex Formation and Activation;" Cell 6:929–939, 1990.

Green et al., "Mutational Analysis of HIV–1 Tat Minimal Domain Peptides: Identification of Trans–Dominant Mutants that Suppress HIV–LTR–Driven Gene Expression;" Cell 58:215–223, 1989.

Gross et al., "Expression of Immunoglobulin in–T–Cell Receptor Chimeric Molecules as Functional Receptors with Antibody–Type Specificity;" Proc. Natl. Acad. Sci. USA 86:10024–10028, 1989.

Haynes, "Scientific and Social Issues of Human Immunodeficiency Virus Vaccine Development;" Science 260:1279–1293, 1993.

Hermanson et al., "B29: A Member of the Immunoglobulin Gene Superfamily Exclusively Expressed on B–Lineage Cells;" Proc. Natl. Acad. Sci. USA 85:6890–6894, 1988.

Hibbs et al., "Mechanisms for Regulating Expression of Membrane Isoforms of FcRIII (CD16);" Scnience 246:1608–1611, 1989.

Hildreth et al., "Involvement of a Leukocyte Adhesion Receptor (LFA–1) in HIV–Induced Synctium Formation;" Science 244:1075–1078, 1989.

Hoffenbach et al., "Unusually High Frequencies of HIV–Specific Cytotoxic T Lymphocytes in Humans;" The Journal of Immunology 452–462, 1989.

Hussey et al., "A Soluble CD4 Protein Selectively Inhibits HIV Replication and Syncytium Formation;" Nature 331:78–81, 1988.

Jenkins et al., "T–Cell Unresponsiveness in vivo and in vitro: Fine Specificity of Induction and Molecular Characterization of the Unresponsive State;" Immunological Reviews 95:113–135, 1987.

Jin et al., "Molecular Cloning of the CD3η Subunit Identifies a CD3–Related Product in Thymus Derived Cells;" Proc. Natl. Acad. Sci. USA 87:3319–3323, 1990.

Johnston et al., "Present Status and Future Prospects for HIV Therapies;" Science 260:1286–1293, 1993.

Klatzmann et al., "T–lymphocyte T4 Molecule Behaves as the Receptor for Human Retrovirus LAV;" Nature 312:767–768, 1984.

Kolanus et al., "T Cell Activation by Clustered Tyrosine Kinases;" Cell 74:1–20, 1993.

Krissansen et al., "Primary Structure of the T3 subunit of the T3/T Cell Antigen Receptor Complex Deduced from cDNA sequences: Evolution of the T3 and δ subunits;" The EMBO Journal 5:1799–1808, 1986.

Kurosaki et al., "A Single Amino Acid in the Glycosyl Phosphatidylinositol Attachment Domain Determines the Membrane Topology of FcRIII;" Nature 342:805–807, 1989.

Kuster et al., "Characterization and Expression of the Gene for the Human Fc Receptor Subunit;" The Journal of Biological Chemistry 265:6448–6452, 1990.

Kuwana et al., "Expression of Chimeric Receptor Composed of Immunoglobulin–Derived V Resions and T–Cell Receptor–Derived C Regions;" Biochemical and Biophysical Research Communications 149:960–968, 1987.

Lamarre et al., "The MHC–Binding and gp 120–Binding Functions of CD4 are Separable;" Science 245:743–746, 1989.

Lanier et al., "Co–association of CD3 with a receptor (CD16) for IgG Fc on Human Natural Killer Cells;" Nature 342:803–805, 1989.

Lawson et al., "Separate Genes Encode Functionally Equivalent ADP/ATP carrier Proteins in Saccharomyces Cerevisiae;" The Journal of Biological Chemistry 263:14812–14818, 1988.

Lifson et al., "Induction of CD4–Dependent Cell Fusion by the HTLV–III/LAV Envelope Glycoprotein;" Nature 323:725–728, 1986.

Lifson et al., "Synthetic CD4 Peptide Derivative that Inhibit HIV Infection and Cytopathicity;" Science 241:712–716, 1988.

Maddon et al., "The T4 Gene Encodes the AIDS Virus Receptor and is Expressed in the Immune System and the Brain;" Cell 47:333–348, 1986.

Malim et al., "Functional Dissection of the HIV–1 Rev Trans–Activator–Derivation of a Trans–Dominant Repressor of Rev Function;" Cell 58:205–214, 1989.

McDougal et al., "Binding of HTLV–III/LAV to T4$^+$ T Cells by a Complex of the 110K Viral Protein and the T4 Molecule;" Science 231:382–385, 1986.

Mercep et al., "T Cell CD3–η Heterodimer Expression and Coupling to Phosphoinositide Hydrolysis;" Science 242:571–574, 1988.

Mercep et al., "Activation–Driven Programmed Cell Death and T Cell Receptor η Expression;" Science 246:1162–1165, 1989.

Morley et al., "The Lysine Residue in the Membrane–Spanning Domain of the β Chain is Necessary for Cell Surface Expression of the T Cell Antigen Receptor;" Rockefeller Press 168:1971–1978, 1988.

Oettgen et al., "A T3–like Protein Complex Associated with the Antigen Receptor or Murine T Cell;" Nature 320:272–275, 1986.

Orloff et al., "Family of Disulphide–Linked Dimers Containing the and η Chains of the T–Cell Receptor and the Chain of Fc Receptors;" Nature 347:189–191, 1990.

Ohashi et al., "Reconstitution of an Active Surface T3/T–Cell Antigen Receptor by DNA Transfer;" Nature 36:606–609, 1985.

Ostergaard et al., "The Role of Ca$^{2+}$ in Activation of Mature Cytotoxic T Lymphocytes for Lysis;" The Journal of Immunology 139:3573–3579, 1987.

Perussia et al., "Murine Natural Killer Cells Express Functional Fc Receptor II Encoded by the FcRa Gene;" Rockefeller University Press 170:73–86, 1989.

Qiu et al., "Organization of the Human and Mouse Low–Affinity FcR Genes: Duplication and Recombination;" Science 248:732–735, 1990.

Ra et al., "Complete Structure of the Mouse Mast Cell Receptor for IgE (FcεRI) and Surface Expression of Chimeric Receptors (Rat–Mouse–Human) on Transfected Cells;" 264:15323–15327, 1989.

Ra et al., "A Macrophage Fc Receptor and the Mast Cell Receptor for IgE share an Identical Subunit;" Nature 341:752–754, 1989.

Rabinovitch et al., "Heterogeneity Among T Cells in Intracellular Free Calcium Responses After Mitogen Stimulation with PHA or ANTI–CD3. Simultaneous use . . . ;" The Journal of Immunology 137:952–961, 1986.

Ravetch et al., "Alternative Membrane Forms of FcRII-I(CD16) on Human Natural Killer Cells and Neutrophils;" Rockefeller University Press 170:481–497, 1989.

Reinherz et al., "Separation of Functional Subsets of Human T Cells by a Monoclonal Antibody;" Proc. Natl. Sci. USA 76:4061–4065, 1979.

Rice et al., "Vaccinia Virus Induces Cellular mRNA Degradation;" Journal of Virology 47:529–539, 1983.

Romeo et al., "Cellular Immunity to HIV Activated by CD4 Fused to T Cell or Fc Receptor Polypeptides;" Cell 64:1037–1046, 1991.

Romeo et al., "Activation of Immune System Effector Function by T–Cell or Fc Receptor Intracellular Domains;" Cold spring Harbor Symposia on Quantitative Biology, LVII:117–125, 1992.

Romeo et al., "Sequence Requirements for Induction of Cytolysis by the T Cell Antigen/Fc Receptor Chain;" Cell 68:889–897, 1992.

Rosenberg et al., "Gene Transfer into Humans–Immunotherapy of Patients with Advanced Melanoma, Using Infiltrating Lymphocytes . . . " The New England Journal of Medicine 323:570–578,1990.

Rosenberg, "Adoptive Immunotherapy for Cancer;" Scientific American 62–69, 1990.

Sakaguchi et al., "B Lymphocyte Lineage–Restricted Expression of mb–1, a Gene with CD3–like Structural Properties;" The EMBO Journal 7:3457–3464, 1988.

Sattentau et al., "The CD4 Antigen: Physiological Ligan and HIV Receptor;" Cell 52:631–633, 1988.

Schwartz et al., "A Cell Culture Model for T Lymphocyte Clonal Anergy;" Science 248:1349–1356, 1990.

Schwartz et al., Costimulation of T Lymphocytes: The Role of CD28, CTLA–4, and B7/BB1 in Interleukin –2 Production and Immunotherapy; Cell 71:1065–1068, 1992.

Sleckman et al., "Expression and Function of CD4 in a Murine T–Cell Hybridoma;" Nature 328:351–353, 1987.

Smith et al., "Blocking of HIV–1 Infectivity by a Soluble, Secreted Form of the CD4 Antigen;" Science 238:1704–1707, 1987.

Sodroski et al., "Role of the HTLV–III/LAV Envelope in Syncytium Formation and Cytopathicity;" Nature 322:470–477, 1986.

Sodroski et al., "A Second Post–Transcriptional Trans–Activator Gene Required for HTLV–III Replication;" Nature 321:412–417, 1986.

Sussman et al., "Failure to Synthesize the T Cell CD3–Chain: Structure and Function of a Partial T Cell Receptor Complex;" Cell 52:85–95, 1988.

Till et al., "HIV–Infected Cells are Killed by rCD4–Ricin A Chain;" Science 242:1166–1168, 1988.

Tirosh et al., "T–Lymphocyte–Mediated Cytolysis as an Excitatory Process of the Target;" Cellular Immunology 95:113–123, 1985.

Traunecker et al., "Soluble CD4 Molecules Neutralize Human Immunodeficiency Virus Type 1;" Nature 331:84–86, 1988.

Trenn et al., "Exocytosis of Cytolytic Granules and not be required for Target Cell Lysis by Cytotoxic T–Lymphocytes;" Nature 330:72–74, 1987.

Trono et al., "HIV–1 Gag Mutants can Dominantly Interfere with the replication of the Wild–Type Virus;" Cell 59:113–120, 1989.
Tunnacliffe et al., "Physical Linkage of Three CD3 Genes on Human Chromosome 11;" The EMBO Journal 6:2953–2957, 1987.
Van Den Elsen et al., "Exon/Intron Organization of the Genes Coding for the δ Chains of the Human and Murine T–Cell Receptor/T3 Complex;" Proc. Natl. Acad. Sci. USA 83:2944–2948, 1986.
Wacholtz et al., "Anti–CD3–Stimulated $Ca^{2+}$ Signal in Individual Human Peripheral T Cells;" The Journal of Immunology 150:5338–5349, 1993.
Watanabe et al., "Effect of Recombinant Soluble CD4 in Rhesus Monkeys Infected with Simian Immunodeficiency Virus of Macaques;" Nature 337:267–270, 1989.
Wegener et al., "The T Cell Receptor/CD3 Complex is Composed of at Least Two Autonomous Transduction Modules;" Cell 68:83–95, 1992.
Weiss et al., "Variable and Conserved Neutralization Antigens of Human Immunodeficiency Virus;" Nature 324:572–575, 1986.
Weiss et al., "Regulation of Protein Tyrosine Kinase Activation by the T–Cell Antigen Receptor on a Malignant Human T Cell Line;" Rockefeller University Press 160:1284–1299, 1984.
Weiss et al., "Requirement for the Coexpression of T3 and the T Cell Antigen Receptor on a Malignant Human T Cell Line;" Rockefeller University Press 160:1284–1299, 1984.
Weissman et al., "Molecular Cloning and Chromosomal Localization of the Human T–Cell Receptor Chain: Distinction from the Molecular CD3 Complex;" Proc. Natl. Acad. Sci. USA 85:9709–9713, 1988.
Weissman et al., "A New Subunit of the Human T–Cell Antigen Receptor Complex;" Nature 324:480–482, 1986.
Weissman et al., "Molecular Cloning of the Zeta chain of the T Cell Antigen Receptor;" Scnience 239:1018–1021, 1988.
Weissman et al., "Role of the Zeta Chain in the Expression of the T Cell Antigen Receptor: Genetic Reconstitution Studies;" The EMBO Journal 8:3651–3656, 1989.
Yague et al., "The T Cell Receptor: The α and β Chains Define Idiotype, and Antigen and MHC Specificity;" Cell 42:81–87, 1985.
Yoffe et al., "Fusion as a Mediator of Cytolysis is Mixtures of Uninfected $CD^{4+}$ Lymphocytes and Cells Infected by Human Immunodeficiency Virus;" Proc. Natl. Acad. Sci. USA 84:1429–1433, 1987.
Young et al., "A Calcium– and Perforin–Independent Pathway of Killing Mediated by Murine Cytolytic Lymphocytes;" Rockefeller University Press 166:1894–1899, 1987.
Zettlmeissl et al., "Expression and Characterization of Human Cd4: Immunoglobulin Fusion Proteins;" DNA and Cell Biology 9:347–353, 1990.
Accolla, J. Exp. Med. 157:1053–1058 (1983).
Aruffo and Seed, EMBO J. 6:3313 (1987).
Ashorn et al., J. Virol. 64:2149 (1990).
Baniyash et al., J. Biol. Chem. 263:9874–9878 (1988).
Bauer et al., Proc. Natl. Acad. Sci. USA 88:3842 (1991).
Blumberg et al., J. Biol. Chem. 265:14036 (1990).
Breitmeyer et al., J. Immunol. 138:726 (1987).
Clayton et al., Proc. Natl. Acad. Sci. USA 88:5202 (1991).
Fleit et al., Proc. Natl. Acad. Sci. USA 79:3275–3279 (1982).
Goldstein et al., Immunol. Rev. 68:5–42 (1982).
Gorny et al., Proc. Natl. Acad. Sci. USA 86:1624 (1989).
Green et al., Cell 58:215–223 (1989).
Irving and Weiss, Cell 64:891–901 (1991).
Kinet, Cell 57:351–354 (1989).
Kohler et al., Eur. J. Immunol. 6:511 (1976).
Kohler et al., Nature 256:495 (1975).
Kohler et al., Eur. J. Immunol. 6:292 (1976).
Lifson et al., Nature 323:725 (1986).
Littman et al., Cell 40:237–246 (1985).
Marasco et al., J. Clin. Invest. 90:1467 (1992).
McDougal, J.S. et al., Science 231:382 (1986).
Mellman, Curr. Opin. Immunol. 1:16–25 (1988).
Miettinen et al., Cell 58:317–327 (1989).
Orloff et al., J. Biol. Chem. 264:14812–14817 (1989).
Ohashi et al., Nature 316:606–609 (1985).
Potocnjak et al., Science 215:1637 (1982).
Ravetch and Kinet, Annu. Rev. Immunol. 9:457–492 (1991).
Reidel et al., Nature 324:68–70 (1986).
Reidel et al., EMBO J. 8:2943–2954 (1989).
Reinherz and Schlossman, Cell 19:821–827 (1980).
Reth, Nature 338:383 (1989).
Samelson et al., Cell 43:223–231 (1985).
Sancho et al., J. Biol. Chem. 264:20760 (1989).
Sharpira–Nahor et al., J. Immunol. 139:35–36 (1987).
Shen et al., Mol. Immunol. 26:959 (1989).
Unkeless et al., Annu. Rev. Immunol. 6:251–281 (1988).
Wands et al., Gastroenterology 80:225–232 (1981).
Watanabe et al., Nature 337:267–270 (1989).
Weiss et al., J. Immunol. 133:123–128 (1984).
Yong–Jiu, Proc. Natl. Acad. Sci. USA 87:3319–3321 (1990).
Alexander et al., "Kinases and Phosphatases in T–Cell Activation," Immunology Today 10:200–205 (1989).
Ashwell et al., "Genetic and Mutational Analysis of the T–Cell Antigen Receptor," Ann. Rev. Immunol. 8:139–167 (1990).
Bernard et al., "High–Affinity Interleukin 2 Binding by an Oncogenic Hybrid Interleukin 2–epidermal Growth Factor Receptor Molecule," Proc. Natl. Acad. Sci. USA 84:2125–2129 (1987).
Verhoeyen et al., "Reshaping Human Antibodies: Grafting an Antilysozyme Activity," Science 259:1534–1536 (1988).
Yarden et al., "Growth Factor Receptor Tyrosine Kinases," Ann. Rev. Biochem. 57:443–478 (1988).
Barclay et al., Leukocyte Antigen Facts Book pp. 27, 106–115, 146–147 (1992).
Stoddard et al., CSH Supp. Quant. Biol. 57:1–15 (1992).
Watson et al., G. Protein Lined Receptor Facts Book, pp. 361 (1994).
Maggio et al., Proc. Natl. Acad. Sci. 90:3103–3107 (1993).
Coghlan et al., New Scientist pp. 14–15 (1995).
Abraham and Veillette, Mol. Cell. Biol. 10:5197–5206 (1990).
Appleby et al., Cell 70:751–763 (1992).
Bachman et al., Current Biology 6:320–326 (1994).
Balk and Terhorst, Immunol. Ser. 45:411–416 (1989).
Bell et al., Mol. Cell Biol. 12:5548–5554 (1992).
Bolen et al., Adv. Cancer res. 57:103–149 (1991).
Burkhardt et al., Proc. Natl. Acad. Sci. USA 88:7410–7414 (1991).
Campbell and Sefton, Mol. Cell. Bio. 12:2315–2321 (1992).
Campbell and Sefton, EMBO J. 9:2125–2131 (1990).
Carter et al., Proc. Natl. Sci. USA 88:2745–2749 (1991).
Chan et al., Proc. Natl. Acad. Sci. USA 88:9166–9170 (1991).

Clark and Ledbetter, Adv. Cancer Res. 52:81–149 (1989).
Clark et al., Science 258:123–126 (1992).
Cooke et al., Cell 65:281–291 (1991).
Cooke and Perlmutter, New Biol. 1:66–74 (1989).
Davidson et al., J. Exp. Med. 175:1483–1492 (1992).
DeFranco, Eur J. Biochem. 210:381–388 (1992).
Eiseman and Bolen, Nature 355:78–80 (1992).
Gassman et al., Eur. J. Immuno. 22:283–286 (1992).
Glaichenhaus et al., Cell 64:511–520 (1991).
Gold et al., Nature 345:810–813 (1990).
Goldsmith and Weiss 84:6879–6883 (1987).
Grant et al., Science 258:1903–1910 (1992).
Hatakeyama et al., Science 252:1523–1528 (1991).
Huang et al., J. Biol. Chem. 267:5467–5473 (1992).
Hutchcroft et al., Proc. Natl. Acad. Sci. USA 89:9107–9111 (1992).
Hutchcroft et al., J. Biol. Chem. 266:14846–14849 (1991).
Hutchcroft et al., J. Biol. Chem. 267:8613–8619 (1992).
Irving et al., J. Exp. Med. 177:1093–1103 (1993).
June et al., J. Immunol. 144:1591–1599 (1990).
June et al., Proc. Natl. Acad. Sci. USA 87:7722–7726 (1990).
Karnitz et al., Mol. Cell. Biol. 12:4521–4530 (1992).
Koga et al., Eur. J. Immunol. 16:1643–1646 (1986).
Kolanus et al., EMBO J. 11:4861–4868 (1992).
Kroczek et al., Nature 322:181–184 (1986).
Lane et al., J. Immunol. 146:715–722 (1991).
Letourneur and Klausner, Science 255:79–82 (1992).
Letourneur and Klausner, Proc. Natl. Acad. Sci. USA 88:8905–8909 (1991).
Li et al., Mol. Cell. Biol. 12:3176–3182 (1992).
Luo and Sefton, Mol. Cell. Biol. 12:4724–4732 (1992).
Muller et al., Mol. Cell. Biol. 12:5087–5093 (1992).
Mustelin et al. Science 247:1584–1587 (1990).
Nishibe et al., Science 250:1253–1256 (1990).
Park et al., J. Biol. Chem. 266:24237–24240 (1991).
Park et al., Proc. Natl. Acad. Sci. USA 88:5453–5456 (1991).
Pendergast et al., Cell 66:161–171 (1991).
Rudd et al., Proc. Natl. Acad. Sci. USA 85:5190–5194 (1988).
Samelson et al., Proc. Natl. Acad. Sci. USA 87:4358–4362 (1990).
Secrist et al., J. Biol. Chem. 268:5886–5893 (1993).
Secrist et al., J. Biol. Chem. 266:12135–12139 (1991).
Stanley et al., J. Immunol. 145:2189–2198 (1990).
Stefanova et al., Science 254:1016–1019 (1991).
Shaw et al., Cell 59:627–636 (1989).
Stein et al., Cell 70:741–750 (1992).
Straus and Weiss, Cell 70:585–593 (1992).
Sugie et al., Proc. Natl. Acad. Sci. USA 88:9132–9135 (1991).
Taniguchi et al., J. Biol. Chem. 266:15790–15796 (1991).
Thomas and Samelson, J. Biol. Chem. 267:1231–1232 (1992).
Tsygankov et al., J. Biol. Chem. 267:18259–18262 (1992).
Turner et al., Cell 60:755–765 (1990).
Veillette et al., Cell 55:301–308 (1988).
Wange et al., J. Biol. Chem. 267:11685–11688 (1992).
Webb et al., Science 249:1295–1297 (1990).
Weiss et al., Annu. Rev. Genet. 25:487–510 (1991).
Wong et al., Oncogene 7:2401–2415 (1992).
Yamanashi et al., Science 251:192–194 (1991).
Yeh et al., J. Immunol. 138:91–97 (1987).

Yokoyama and Shevach, Year Immunol. 4:110–146 (1989).
Zioncheck et al., J. Biol. Chem. 263:19195–19202 (1988).
Zioncheck et al., J. Biol. Chem. 261:15637–15643 (1986).
Al–Jaufy et al., Infection and Immunity 62:956–960 (1994).
Aullo et al., EMBO J. 11:575–583 (1992).
Chao et al., J. Biol. Chem. 264:5812–5817 (1989).
Lin et al., FASEB J. 7:1070–1080 (1993).
Moebius et al., J. Exp. Med. 176:507–517 (1992).
Sekigawa et al., J. Virol. 64:5194–5198 (1990).
Marshall, Science, 269:1050–1055 (1995).
Brown, Washington Post, A1 and A22 (1995).
Jones et al., Nature, 323:346–349 (1986).
Suda et al., Blood, 79(9):2288–2295 (1992).
He et al., Blood, 79(9):2296–2302 (1992).
Nakumara et al., 21:236–242 (1993).
Alberola–lla et al., J. Immunology, 151(9):4423–4430 (1993).
Stancovski et al., "Targeting of T Lymphocytes to Neu/HER2–Expressing Cells Using Chimeric Single Chain Fv Receptors" *The Journal of Immunology* 151:6577–6582 (1993).
Weiss et al., "Regulation of Protein Tyrosine Kinase Activation by the T–cell Antigen Receptor ζ Chain" *Cold Spring Harbor Symposia on Quantitative Biology* LVII:107–115 (1992).
Clayton, *J. Exp. Med.,* 172: 1243–1253 (1990).
Fanger, *Imm. Today,* 10: 92–99 (1989).
Governman, *Cell,* 60: 929–939 (1990).
Hoffenbach et al., *J. Immunol.,* 142: 452–462 (1989).
Morley, *J. Exp. Med.,* 168: 1971–1978 (1988).
Nakamura, *Exp. Hematal,* 21: 236–242 (1993).
Perussia, *J. Exp. Med.* 170: 73–86 (1987).
Ra, *J. Biol. Chem.,* 264: 15323–15327 (1989).
Ravetch, *J. Exp. Med.* 170: 481–497 (1989).
Traunecker et al., *Nature,* 339: 68–70 (1989).
Valentin et al., *J. Immunol.,* 144: 934–937 (1990).
Weiss, *J. Exp. Med.,* 160: 1284–1299 (1984).
Young et al., *J. Exp. Med.,* 166: 1884–1889 (1987).
Fahey et al., *Clin. Exp. Immunol.* 88:1–5, 1992.*
Fox, J.L., *Bio/Technology* 12:128, Feb. 1994.*
Haynes et al., *Ann. Med.* 28:39–41, 1996.*

* cited by examiner (Seq. ID No: 24)

```
1    MEHSTFLSGL  VLATLLSQVS  PFKIPIEELE  DRVFVNCNTS  ITWVEGTVGT
51   LLSDITRLDL  GKRILDPRGI  YRCNGTDIYK  DKESTVQVHY  RMCQSCVEID
101  PATVAGIIVT  DVIATLLLAL  GVFCFAGHET  GRLSGAADTQ  ALLRNDQVYQ
151  PLRDRDDAQY  SHLGGNWARN  K*
```

Fig. 16

(Seq ID NO: 25)

```
1    MEQGKGLAVL  ILAIILLQGT  LAQSIKGNHL  VKVYDYQEDG  SVLLTCDAEA
51   KNITWFKDGK  MIGFLTEDKK  KWNLGSNAKD  PRGMYQCKGS  QNKSKPLQVY
101  YRMCQNCIEL  NAATISGFLF  AEIVSIFVLA  VGVYFIAGQD  GVRQSRASDK
151  QTLLPNDQLY  QPLKDREDDQ  YSHLQGNQLR  RN*
```

Fig. 17

(Seq ID No: 26)

```
1    MPGGLEALRA  LPLLLFLSYA  CLGPGCQALR  VEGGPPSLTV  NLGEEARLTC
51   ENNGRNPNIT  WWFSLQSNIT  WPPVPLGPGQ  GTTGQLFFPE  VNKNTGACTG
101  CQVIENNILK  RSCGTYLRVR  NPVPRPFLDM  GEGTKNRIIT  AEGIILLFCA
151  VVPGTLLLFR  KRWQNEKFGV  DMPDDYEDEN  LYEGLNLDDC  SMYEDISRGL
201  QGTYQDVGNL  HIGDAQLEKP  *
```

Fig. 18

(Seq ID No: 27)

```
1    MATLVLSSMP  CHWLLFLLLL  FSGEPVPAMT  SSDLPLNFQG  SPCSQIWQHP
51   RFAAKKRSSM  VKFHCYTNHS  GALTWFRKRG  SQQPQELVSE  EGRIVQTQNG
101  SVYTLTIQNI  QYEDNGIYFC  KQKCDSANHN  VTDSCGTELL  VLGFSTLDQL
151  KRRNTLKDGI  ILIQTLLIIL  FIIVPIFLLL  DKDDGKAGME  EDHTYEGLNI
201  DQTATYEDIV  TLRTGEVKWS  VGEHPGQE*
```

Fig. 19

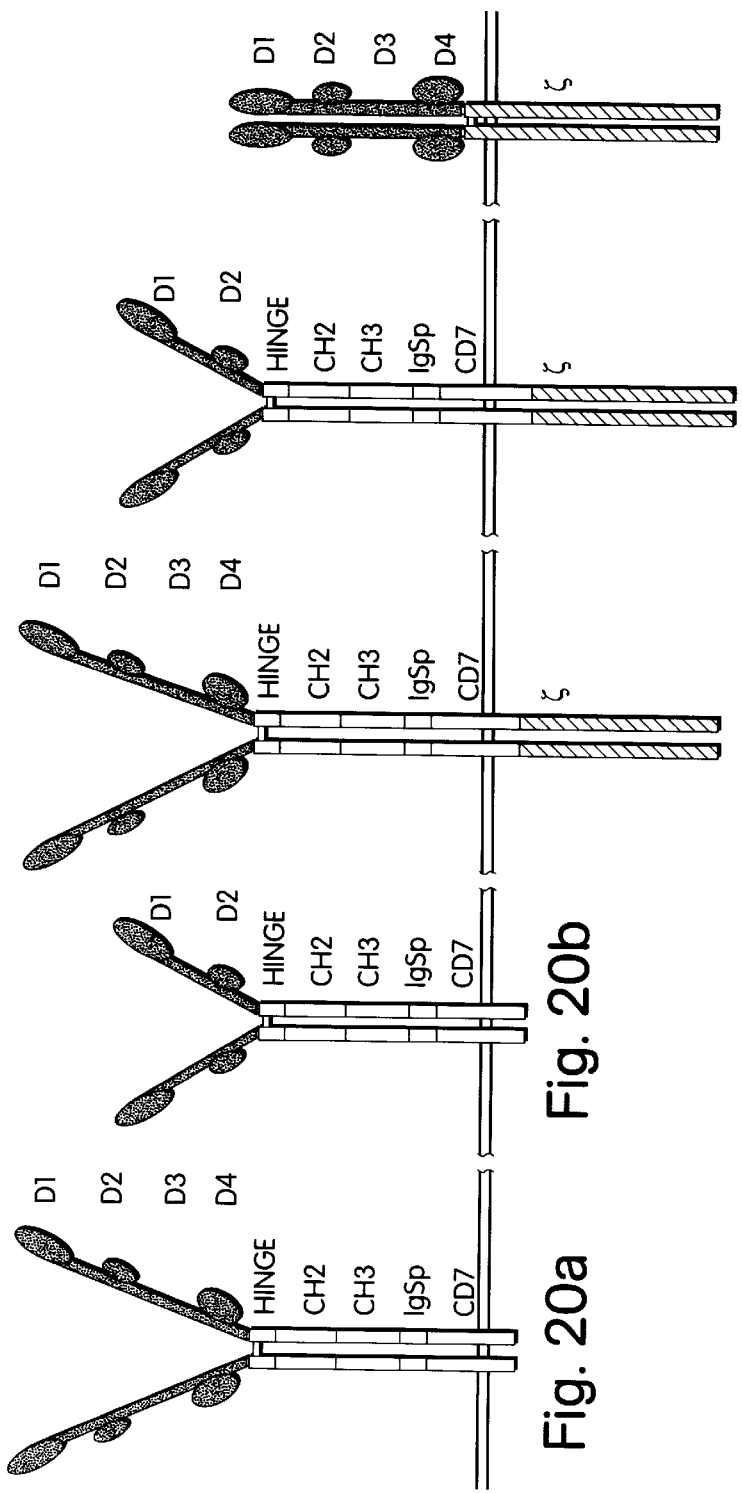

D1 - D4 of CD4

Nucleic Acid Sequence

```
GCCTGTTTGA GAAGCAGCGG GCAAGAAAGA CGCAAGCCCA GAGGCCCTGC   51
CATTTCTGTG GGCTCAGGTC CCTACTGGCT CAGGCCCCTG CCTCCCTCGG  101
CAAGGCCACA ATGAACCGGG GAGTCCCTTT TAGGCACTTG CTTCTGGTGC  151
TGCAACTGGC GCTCCTCCCA GCAGCCACTC AGGGAAACAA AGTGGTGCTG  201
GGCAAAAAAG GGGATACAGT GGAACTGACC TGTACAGCTT CCCAGAAGAA  251
GAGCATACAA TTCCACTGGA AAAACTCCAA CCAGATAAAG ATTCTGGGAA  301
ATCAGGGCTC CTTCTTAACT AAAGGTCCAT CCAAGCTGAA TGATCGCGCT  351
GACTCAAGAA GAAGCCTTTG GGACCAAGGA AACTTCCCCC TGATCATCAA  401
GAATCTTAAG ATAGAAGACT CAGATACTTA CATCTGTGAA GTGGAGGACC  451
AGAAGGAGGA GGTGCAATTG CTAGTGTTCG GATTGACTGC CAACTCTGAC  501
ACCCACCTGC TTCAGGGGCA GAGCCTGACC CTGACCTTGG AGAGCCCCCC  551
TGGTAGTAGC CCCTCAGTGC AATGTAGGAG TCCAAGGGGT AAAAACATAC  601
AGGGGGGGAA GACCCTCTCC GTGTCTCAGC TGGAGCTCCA GGATAGTGGC  651
ACCTGGACAT GCACTGTCTT GCAGAACCAG AAGAAGGTGG AGTTCAAAAT  701
AGACATCGTG GTGCTAGCTT TCCAGAAGGC CTCCAGCATA GTCTATAAGA  751
AAGAGGGGGA ACAGGTGGAG TTCTCCTTCC CACTCGCCTT TACAGTTGAA  801
AAGCTGACGG GCAGTGGCGA GCTGTGGTGG CAGGCGGAGA GGGCTTCCTC  851
CTCCAAGTCT TGGATCACCT TTGACCTGAA GAACAAGGAA GTGTCTGTAA  901
AACGGGTTAC CCAGGACCCT AAGCTCCAGA TGGGCAAGAA GCTCCCGCTC  951
CACCTCACCC TGCCCCAGGC CTTGCCTCAG TATGCTGGCT CTGGAAACCT 1001
CACCCTGGCC CTTGAAGCGA AAACAGGAAA GTTGCATCAG GAAGTGAACC 1051
TGGTGGTGAT GAGAGCCACT CAGCTCCAGA AAAATTTGAC CTGTGAGGTG 1101
TGGGGACCCA CCTCCCCTAA GCTGATGCTG AGCTTGAAAC TGGAGAACAA 1151
GGAGGCAAAG GTCTCGAAGC GGGAGAAGCC GGTGTGGGTG CTGAACCCTG 1201
AGGCGGGGAT GTGGCAGTGT CTGCTGAGTG ACTCGGGACA GGTCCTGCTG 1251
GAATCCAACA TCAAGGTTCT GCCCACATGG TCCACCCCGG TGCACGCGGA 1301
TCCC (SEQ ID NO: 28)
```

Amino Acid Sequence

```
MNRGVPFRHL LLVLQLALLP AATQGNKVVL GKKGDTVELT CTASQKKSIQ   51
FHWKNSNQIK ILGNQGSFLT KGPSKLNDRA DSRRSLWDQG NFPLIIKNLK  101
IEDSDTYICE VDQKEEVQL LVFGLTANSD THLLQGQSLT LTLESPPGSS  151
PSVQCRSPRG KNIQGGKTLS VSQLELQDSG TWTCTVLQNQ KKVEFKIDIV  201
VLAFQKASSI VYKKEGEQVE FSFPLAFTVE KLTGSGELWW QAERASSSKS  251
WITFDLKNKE VSVKRVTQDP KLQMGKYLPL HLTLPQALPQ YAGSGNLTLA  301
LEAKTGKLHQ EVNLVVMRAT QLQKNLTCEV WGPTSPKLML SLKLENKEAK  351
VSKREKPVWV LNPEAGMWQC LLSDSGQVLL ESNIKVLPTW STPVHADP
(SEQ ID NO: 29)
```

Nucleic Acid Sequence

```
GCCTGTTTGA GAAGCAGCGG GCAAGAAAGA CGCAAGCCCA GAGGCCCTGC  51
CATTTCTGTG GGCTCAGGTC CCTACTGGCT CAGGCCCCTG CCTCCCTCGG 101
CAAGGCCACA ATGAACCGGG GAGTCCCTTT TAGGCACTTG CTTCTGGTGC 151
TGCAACTGGC GCTCCTCCCA GCAGCCACTC AGGGAAACAA AGTGGTGCTG 201
GGCAAAAAAG GGGATACAGT GGAACTGACC TGTACAGCTT CCCAGAAGAA 251
GAGCATACAA TTCCACTGGA AAAACTCCAA CCAGATAAAG ATTCTGGGAA 301
ATCAGGGCTC CTTCTTAACT AAAGGTCCAT CCAAGCTGAA TGATCGCGCT 351
GACTCAAGAA GAAGCCTTTG GACCAAGGA AACTTCCCCC TGATCATCAA 401
GAATCTTAAG ATAGAAGACT CAGATACTTA CATCTGTGAA GTGGAGGACC 451
AGAAGGAGGA GGTGCAATTG CTAGTGTTCG GATTGACTGC CAACTCTGAC 501
ACCCACCTGC TTCAGGGGCA GAGCCTGACC CTGACCTTGG AGAGCCCCCC 551
TGGTAGTAGC CCCTCAGTGC AATGTAGGAG TCCAAGGGGT AAAAACATAC 601
AGGGGGGGAA GACCCTCTCC GTGTCTCAGC TGGAGCTCCA GGATAGTGGC 651
ACCTGGACAT GCACTGTCTT GCAGAACCAG AAGAAGGTGG AGTTCAAAAT 701
AGACATCGTG GTGCTAGCT (SEQ ID NO: 30)
```

Amino Acid Sequence

```
MNRGVPFRHL LLVLQLALLP AATQGNKVVL GKKGDTVELT CTASQKKSIQ  51
FHWKNSNQIK ILGNQGSFLT KGPSKLNDRA DSRRSLWDQG NFPLIIKNLK 101
IEDSDTYICE VEDQKEEVQL LVFGLTANSD THLLQGQSLT LTLESPPGSS 151
PSVQCRSPRG KNIQGGKTLS VSQLELQDSG TWTCTVLQNQ KKVEFKIDIV 201
VLA (SEQ ID NO: 31)
```

Fig. 24

Hinge, CH2, and CH3 Domains of Human IgG1

Nucleic Acid Sequence

```
GCTAGCAGAG CCCAAATCTT GTGACAAAAC TCACACATGC CCACCGTGCC  51
CAGCACCTGA ACTCCTGGGG GGACCGTCAG TCTTCCTCTT CCCCCCAAAA 101
CCCAAGGACA CCCTCATGAT CTCCCGGACC CCTGAGGTCA CATGCGTGGT 151
GGTGGACGTG AGCCACGAAG ACCCTGAGGT CAAGTTCAAC TGGTACGTGG 201
ACGGCGTGGA GGTGCATAAT GCCAAGACAA AGCCGCGGGA GGAGCAGTAC 251
AACAGCACGT ACCGGGTGGT CAGCGTCCTC ACCGTCCTGC ACCAGGACTG 301
GCTGAATGGC AAGGAGTACA AGTGCAAGGT CTCCAACAAA GCCCTCCCAG 351
CCCCCATCGA GAAAACCATC TCCAAAGCCA AAGGGCAGCC CCGAGAACCA 401
CAGGTGTACA CCCTGCCCCC ATCCCGGGAT GAGCTGACCA AGAACCAGGT 451
CAGCCTGACC TGCCTGGTCA AAGGCTTCTA TCCCAGCGAC ATCGCCGTGG 501
AGTGGGAGAG CAATGGGCAG CCGGAGAACA ACTACAAGAC CACGCCTCCC 551
GTGCTGGACT CCGACGGCTC CTTCTTCCTC TACAGCAAGC TCACCGTGGA 601
CAAGAGCAGG TGGCAGCAGG GGAACGTCTT CTCATGCTCC GTGATGCATG 651
AGGCTCTGCA CAACCACTAC ACGCAGAAGA GCCTCTCCCT GTCTCCGGGG 701
CTGCAACTGG ACGAGACCTG TGCTGAGGCC CAGGACGGGG AGCTGGACGG 751
GCTCTGGACG ACGGATCC  (SEQ ID NO: 32)
```

Amino Acid Sequence

```
EPKSCDKTHT CPPCPAPELL GGPSVFLFPP KPKDTLMISR TPEVTCVVVD  51
VSHEDPEVKF NWYVDGVEVH NAKTKPREEQ YNSTYRVVSV LTVLHQDWLN 101
GKEYKCKVSN KALPAPIEKT ISKAKGQPRE PQVYTLPPSR DELTKNQVSL 151
TCLVKGFYPS DIAVEWESNG QPENNYKTTP PVLDSDGSFF LYSKLTVDKS 201
RWQQGNVFSC SVMHEALHNH YTQKSLSLSP GLQLDETCAE AQDGELDGLW 251
TTDP  (SEQ ID NO: 33)
```

Fig. 25

CD7 Transmembrane Domain

Nucleic Acid Sequence

```
CCAAGGGCCT CTGCCCTCCC TGCCCCACCG ACAGGCTCCG CCCTCCCTGA 51
CCCGCAGACA GCCTCTGCCC TCCCTGACCC GCCAGCAGCC TCTGCCCTCC 101
CTGCGGCCCT GGCGGTGATC TCCTTCCTCC TCGGGCTGGG CCTGGGGGTG 151
GCGTGTGTGC TGGCGAGGAC GCGT (SEQ ID NO: 34)
```

Amino Acid Sequence

```
PRASALPAPP TGSALPDPQT ASALPDPPAA SALPAALAVI SFLLGLGLGV 51
ACVLARTR (SEQ.ID NO: 35)
```

Fig. 26

Zeta Intracellular Domain

Nucleic Acid Sequence

```
ACGCGTTTCA GCAGGAGCGC AGAGCCCCCC GCGTACCAGC AGGGCCAGAA 51
CCAGCTCTAT AACGAGCTCA ATCTAGGACG AAGAGAGGAG TACGATGTTT 101
TGGACAAGAG ACGTGGCCGG GACCCTGAGA TGGGGGGAAA GCCGAGAAGG 151
AAGAACCCTC AGGAAGGCCT GTACAATGAA CTGCAGAAAG ATAAGATGGC 201
GGAGGCCTAC AGTGAGATTG GGATGAAAGG CGAGCGCCGG AGGGGCAAGG 251
GGCACGATGG CCTTTACCAG GGTCTCAGTA CAGCCACCAA GGACACCTAC 301
GACGCCCTTC ACATGCAGGC CCTGCCCCCT CGCTAAAGCG GCCGC
(SEQ ID NO: 36)
```

Amino Acid Sequence

```
TRFSRSAEPP AYQQGQNQLY NELNLGRREE YDVLDKRRGR DPEMGGKPRR 51
KNPQEGLYNE LQKDKMAEAY SEIGMYGERR RGKGHDGLYQ GLSTATKDTY 101
DALHMQALPP R (SEQ ID NO: 37)
```

Fig. 27

TARGETED CYTOLYSIS OF HIV-INFECTED CELLS BY CHIMERIC CD4 RECEPTOR-BEARING CELLS

This application is a divisional of application, Seed et al., U.S. Ser. No. 08/284,391, filed Aug. 2, 1994, now U.S. Pat. No. 5,851,828 which is a continuation-in-part of Seed et al., U.S. Ser. No. 08/195,395, filed Feb. 14, 1994, now abandoned, which is a continuation-in-part of Seed et al., U.S. Ser. No. 07/847,566, filed Mar. 6, 1992, now abandoned, which is a continuation-in-part of Seed et al., U.S. Ser. No. 07/665,961, filed Mar. 7, 1991, now abandoned.

This invention was made with Government support under Contract #AI 27849 awarded by the National Institutes of Health. The Government has certain rights in this invention.

FIELD OF THE INVENTION

The invention concerns functional chimeras between CD4 fragments and immune cell receptors which are capable of directing immune cells to lyse HIV-infected cells, but which do not render the immune cells susceptible to HIV infection. The invention therefore provides a novel and effective HIV therapeutic.

BACKGROUND OF THE INVENTION

T cell recognition of antigen through the T cell receptor is the basis of a range of immunological phenomena. The T cells direct what is called cell-mediated immunity. This involves the destruction by cells of the immune system of foreign tissues or infected cells. A variety of T cells exist, including "helper" and "suppressor" cells, which modulate the immune response, and cytotoxic (or "killer") cells, which can kill abnormal cells directly.

A T cell that recognizes and binds a unique antigen displayed on the sur ace of another cell becomes activated; it can then multiply, and if it is a cytotoxic cell, it can kill the bound cell.

HIV and Immunopathogenesis

In 1984 HIV was shown to be the etiologic agent of AIDS. Since that time the definition of AIDS has been revised a number of times with regard to what criteria should be included in the diagnosis. However, despite the fluctuation in diagnostic parameters, the simple common denominator of AIDS is the infection with HIV and subsequent development of persistent constitutional symptoms and AIDS-defining diseases such as a secondary infections, neoplasms, and neurologic disease. *Harrison's Principles of Internal Medicine,* 12th ed., McGraw Hill (1991).

HIV is a human retrovirus of the lentivirus group. The four recognized human retroviruses belong to two distinct groups: the human T lymphotropic (or leukemia) retroviruses, HTLV-1 and HTLV-2, and the human immunodeficiency viruses, HIV-1 and HIV-2. The former are transforming viruses whereas the latter are cytopathic viruses.

HIV-1 has been identified as the most common cause of AIDS throughout the world. Sequence homology between HIV-2 and HIV-1 is about 40% with HIV-2 being more closely related to some members of a group of simian immunodeficiency viruses (SIV). See Curran, J. et al., *Science,* 329:1357–1359 (1985); Weiss, R. et al., *Nature,* 324:572–575 (1986).

HIV has the usual retroviral genes (env, gag, and pol) as well as six extra genes involved in the replication and other biologic activities of the virus. As stated previously, the common denominator of AIDS is a profound immunosuppression, predominantly of cell-mediated immunity. This immune suppression leads to a variety of opportunistic diseases, particularly certain infections and neoplasms.

The main cause of the immune defect in AIDS has been identified as a quantitative and qualitative deficiency in the subset of thymus-derived (T) lymphocytes, the T4 population. This subset of cells is defined phenotypically by the presence of the CD4 surface molecule, which has been demonstrated to be the cellular receptor for HIV. Dalgleish et al., *Nature* 312:763 (1984). Although the T4 cell is the major cell type infected with HIV, essentially any human cell that expresses the CD4 molecule on its-surface is capable of binding to and being infected with HIV.

Traditionally, CD4$^+$ T cells have been assigned the role of helper/inducer, indicating their function in providing an activating signal to B cells, or inducing T lymphocytes bearing the reciprocal CD8 marker to become cytotoxic/suppressor cells. Reinherz and Schlossman, *Cell* 19:821–827 (1980); Goldstein et al., *Immunol. Rev.* 68:5–42 (1982).

HIV binds specifically and with high affinity, via a stretch of amino acids in the viral envelope (gp120), to a portion of the V1 region of the CD4 molecule located near its N-terminus. Following binding, the virus fuses with the target cell membrane and is internalized. Once internalized it uses the enzyme reverse transcriptase to transcribe its genomic RNA to DNA, which is integrated into the cellular DNA where it exists for the life of the cell as a "provirus."

The provirus may remain latent or be activated to transcribe mRNA and genomic RNA, leading to protein synthesis, assembly, new virion formation, and budding of virus from the cell surface. Although the precise mechanism by which the virus induces cell death has not been established, it is believed that the major mechanism is massive viral budding from the cell surface, leading to disruption of the plasma membrane and resulting osmotic disequilibrium.

During the course of the infection, the host organism develops antibodies against viral proteins, including the major envelope glycoproteins gp120 and gp41. Despite this humoral immunity, the disease progresses, resulting in a lethal immunosuppression characterized by multiple opportunistic infections, parasitemia, dementia, and death. The failure of the host anti-viral antibodies to arrest the progression of the disease represents one of the most vexing and alarming aspects of the infection, and augurs poorly for vaccination efforts based upon conventional approaches.

Two factors may play a role in the efficacy of the humoral response to immunodeficiency viruses. First, like other RNA viruses (and like retroviruses in particular), the immunodeficiency viruses show a high mutation rate in response to host immune surveillance. Second, the envelope glycoproteins themselves are heavily glycosylated molecules presenting few epitopes suitable for high affinity antibody binding. The poorly antigenic target which the viral envelope presents allows the host little opportunity for restricting viral infection by specific antibody production.

Cells infected by the HIV virus express the gp120 glycoprotein on their surface. Gp120 mediates fusion events among CD4$^+$ cells via a reaction similar to that by which the virus enters the uninfected cells, leading to the formation of short-lived multinucleated giant cells. Syncytium formation is dependent on a direct interaction of the gp120 envelope glycoprotein with the CD4 protein. Dalgleish et al., supra;

Klatzman, D. et al., *Nature* 312:763 (1984); McDougal, J. S. et al., *Science* 231:382 (1986); Sodroski, J. et al., *Nature* 322:470 (1986); Lifson, J. D. et al., *Nature* 323:725 (1986); Sodroski, J. et al., *Nature* 321:412 (1986).

Evidence that the CD4-gp120 binding is responsible for viral infection of cells bearing the CD4 antigen includes the finding that a specific complex is formed between gp120 and CD4. McDougal et al., supra. Other investigators have shown that the cell lines, which were noninfective for HIV, were converted to infectable cell lines following transfection and expression-of the human CD4 cDNA gene. Maddon et al., *Cell* 46:333–348 (1986).

Therapeutic programs based on soluble CD4 as a passive agent to interfere with viral adsorption and syncytium-mediated cellular transmission have been proposed and successfully demonstrated in vitro by a number of groups (Deen et al., *Nature* 331:82–84 (1988); Fisher et al., *Nature* 331:76–78 (1988); Hussey et al., *Nature* 331:78–81 (1988); Smith et al., *Science* 238:1704–1707 (1987); Traunecker et al., *Nature* 331:84–86 (1988)); and CD4 immunoglobulin fusion proteins with extended halflives and modest biological activity have subsequently been developed (Capon et al., *Nature* 337:525–531 (1989); Traunecker et al. *Nature* 339, 68–70 (1989); Byrn et al., *Nature* 344:667–670 (1990); Zettlmeissl et al., *DNA Cell Biol.* 9:347–353 (1990)). Although CD4 immunotoxin conjugates or fusion proteins show potent cytotoxicity for infected cells in vitro (Chaudhary et al., *Nature* 335:369–372 (1988); Till et al., *Science* 242:1166–1168 (1988)), the latency of the immunodeficiency syndrome makes it unlikely that any single-treatment therapy will be effective in eliminating viral burden, and the antigenicity of foreign fusion proteins is likely to limit their acceptability in treatments requiring repetitive dosing. Trials with monkeys affected with SIV have shown that soluble CD4, if administered to animals without marked CD4 cytopenia, can reduce SIV titer and improve in vitro measures of myeloid potential (Watanabe et al., *Nature* 337:267–270 (1989)). However a prompt viral reemergence was observed after treatment was discontinued, suggesting that lifelong administration might be necessary to prevent progressive immune system debilitation.

T Cell and Fc Receptors

Cell surface expression of the most abundant form of the T cell antigen receptor (TCR) requires the coexpression of at least 6 distinct polypeptide chains (Weiss et al., *J. Exp. Med.* 160:1284–1299 (1984); Orloffhashi et al., *Nature* 316:606–609 (1985); Berkhout et al., *J. Biol. Chem.* 263:8528–8536 (1988); Sussman et al., *Cell* 52:85–95 (1988)), the α/β antigen binding chains, the three polypeptides of the CD3 complex, and ζ. If any of the chains are absent, stable expression of the remaining members of the complex does not ensue. ζ is the limiting polypeptide for surface expression of the complete complex (Sussman et al., *Cell* 52:85–95 (1988)) and is thought to mediate at least a fraction of the cellular activation programs triggered by receptor recognition of ligand (Weissman et al., *EMBO J.* 8:3651–3656 (1989); Frank et al., *Science* 249:174–177 (1990)). A 32 kDa type I integral membrane homodimer, ζ (zeta) has a 9 residue extracellular domain with no sites for N-linked glycan addition, and a 112 residue (mouse) or 113 residue (human) intracellular domain (Weissman et al., *Science* 238:1018–1020 (1988); Weissman et al., *Proc. Natl. Acad. Sci. USA* 85:9709–9713 (1988)). An isoform of ζ called η (eta) (Baniyash et al., *J. Biol. Chem.* 263:9874–9878 (1988); Orloff et al., *J. Biol. Chem.* 264:14812–14817 (1989)), which arises from an alternate mRNA splicing pathway (Jin et al., *Proc. Natl. Acad. Sci. USA* 87:3319–3233 (1990)), is present in reduced amounts in cells expressing the antigen receptor. ζ-η heterodimers are thought to mediate the formation of inositol phosphates, as well as the receptor-initiated programmed cell death called apoptosis (Mercep et al., *Science* 242:571–574 (1988); Mercep et al., *Science* 246:1162–1165 (1989)).

Like ζ and η, the Fc receptor-associated γ chain is expressed in cell surface complexes with additional polypeptides, some of which mediate ligand recognition, and others of which have undefined function. γ (gamma) bears a homodimeric structure and overall organization very similar to that of ζ and is a component of both the mast cell/basophil high affinity IgE receptor, FcεRI, which consists of at least three distinct polypeptide chains (Blank et al., *Nature* 337:187–189 (1989); Ra et al., *Nature* 241:752–754 (1989)), and one of the low affinity receptors for IgG, represented in mice by FcγRIIα (Ra et al., *J. Biol. Chem.* 264:15323–15327 (1989)), and in humans by the CD16 subtype expression by macrophages and natural killer cells, $CD16_{TM}$ (CD16 transmembrane) (Lanier et al., *Nature* 342:803–805 (1989); Anderson et al., *Proc. Natl. Acad. Sci. USA* 87:2274–2278 (1990)) and with a polypeptide of unidentified function (Anderson et al., *Proc. Natl. Acad. Sci. USA* 87:2274–2278 (1990)). Recently it has been reported that γ is expressed by a mouse T cell line, CTL, in which it forms homodimers as well as γ-ζ and γ-η heterodimers (Orloff et al., *Nature* 347:189–191 (1990)).

The Fc receptors mediate phagocytosis of immune complexes, transcytosis, and antibody dependent cellular cytotoxicity (ADCC) (Ravetch and Kinet, *Annu. Rev. Immunol.* 9:457–492 (1991); Unkeless et al., *Annu. Rev. Immunol* 6:251–281 (1988); and Mellman, *Curr. Opin. Immunol.* 1:16–25 (1988)). Recently it has been shown that one of the murine low affinity Fc receptor isoforms, FcRγIIIB1, mediates internalization of Ig-coated targets into clathrin coated pits, and that another low affinity receptor, FcrγIIIA mediates ADCC through its association with one or more members of a small family of 'trigger molecules' (Miettinen et al., *Cell* 58:317–327 (1989); and Hunziker and Mellman, *J. Cell Biol.* 109:3291–3302 (1989)). These trigger molecules, T cell receptor (TCR) ζ chain, TCR η chain, and Fc receptor γ chain interact with ligand recognition domains of different immune system receptors and can autonomously initiate cellular effector programs, including cytolysis, following aggregation (Samelson et al., *Cell* 43:223–231 (1985); Weissman et al., *Science* 239:1018–1020 (1988); Jin et al., *Proc. Natl. Acad. Sci. USA* 87:3319–3323 (1990); Blank et al., *Nature* 337:187–189 (1989); Lanier et al., *Nature* 342:803–805 (1989); Kurosaki and Ravetch, *Nature* 342:805–807 (1989); Hibbs et al., *Science* 246:1608–1611 (1989); Anderson et al., *Proc. Natl. Acad. Sci USA* 87:2274–2278 (1990); and Irving and Weiss, *Cell* 64:891–901 (1991)).

In drawing parallels between the murine and human low affinity Fc receptor families, however, it has become clear that the human FcRγIIA and C isoforms have no murine counterpart. In part because of this, their function has yet to be defined.

Because humoral agents based on CD4 alone may have limited utility in vivo, previous work explored the possibility of augmenting cellular immunity to HIV. Preparations of protein chimeras in which the extracellular domain of CD4 is fused to the transmembrane and/or intracellular domains of T cell receptor, IgG Fc receptor, or B cell receptor signal transducing elements have been identified (U.S. Ser. Nos. 07/847,566 and 07/665,961, hereby incorporated by reference). Cytolytic T cells expressing chimeras which include an extracellular CD4 domain show potent MHC-independent destruction of cellular targets expressing HIV envelope proteins. An extremely important and novel component of this approach has been the identification of single T cell receptor, Fc receptor, and B cell receptor chains whose aggregation suffices to initiate the cellular response. One particularly useful application of this approach has been the invention of chimeras between CD4 and ζ, η, or γ that direct cytolytic T lymphocytes to recognize and kill cells expressing HIV gp120 (U.S. Ser. Nos. 07/847,566 and 07/665,961, hereby incorporated by reference).

SUMMARY OF THE INVENTION

In general, the invention features a method of directing a cellular immune response against an HIV-infected cell in a mammal. The method involves administering to the mammal an effective amount of therapeutic cells, the therapeutic cells expressing a membrane-bound, proteinaceous chimeric receptor comprising (a) an extracellular portion which includes a fragment of CD4 which is capable of specifically recognizing and binding the HIV-infected cell but which does not mediate HIV infection and (b) an intracellular portion which is capable of signalling the therapeutic cell to destroy the receptor-bound HIV-infected cell.

In a second aspect, the invention features a cell which expresses a proteinaceous membrane-bound chimeric receptor which comprises (a) an extracellular portion which includes a fragment of CD4 which is capable of specifically recognizing and binding the HIV-infected cell but which does not mediate HIV infection and (b) an intracellular portion which is capable of signalling the therapeutic cell to destroy the receptor-bound HIV-infected cell.

In preferred embodiments of both aspects, the CD4 fragment is amino acids 1–394 of CD4 or is amino acids 1–200 of CD4; the CD4 fragment is separated from the intracellular portion by the CD7 transmembrane domain shown in FIG. 26 or by the hinge, CH2, and CH3 domains of the human IgG1 molecule shown in FIG. 25; the intracellular portion is the signal-transducing portion of a T cell receptor protein (for example, ζ), a B cell receptor protein, or an Fc receptor protein; and the therapeutic cells are selected from the group consisting of: (a) T lymphocytes; (b) cytotoxic T lymphocytes; (c) natural killer cells; (d) neutrophils; (e) granulocytes; (f) macrophages; (g) mast cells; (h) HeLa cells; and (i) embryonic stem cells (ES).

In other aspects, the invention features DNA encoding a chimeric receptor of the invention; and a vector including that chimeric receptor DNA.

Although the specific embodiment of the present invention is a chimera between CD4 and zeta, any receptor chain having a similar function to these molecules, e.g., in granulocytes or B lymphocytes, could be used for the purposes disclosed here. The distinguishing features of a desirable immune cell trigger molecule comprises the ability to be expressed autonomously (i.e., as a single chain), the ability to be fused to an extracellular CD4 domain such that the resultant chimera is present on the surface of a therapeutic cell, and the ability to initiate cellular effector programs upon aggregation secondary to encounter with a target ligand.

At present the most convenient method for delivery of the chimeras to immune system cells is through some form of genetic therapy. However reconstituting immune system cells with chimeric receptors by mixture of the cells with suitably solubilized purified chimeric protein would also result in the formation of an engineered cell population capable of responding to HIV-infected targets. Similar approaches have been used, for example, to introduce the CD4 molecule into erythrocytes for therapeutic purposes. In this case the engineered cell population would not be capable of self renewal.

The present invention relates to functional and simplified chimeras between CD4 fragments and T cell receptor, B cell receptor, and Fc receptor subunits which are capable of directing immune cells to recognize and lyse HIV-infected cells. The method for directing the cellular response in a mammal comprises administering an effective amount of therapeutic cells (for example, cytotoxic T lymphocytes) to the mammal, the cells being capable of recognizing and destroying the HIV-infected cell.

The invention also includes the chimeric receptor proteins which direct the cytotoxic T lymphocytes to recognize and lyse HIV-infected cells, the host cells transformed with a vector comprising the chimeric receptors, and antibodies directed against the chimeric receptors.

These and other non-limiting embodiments of the present invention will be apparent to those of skill from the following detailed description of the invention.

In the following detailed description, reference will be made to various methodologies known to those of skill in the art of molecular biology and immunology. Publications and other materials setting forth such known methodologies to which reference is made are incorporated herein by reference in their entireties as though set forth in full.

Standard reference works setting forth the general principles of recombinant DNA technology include Watson et al., *Molecular Biology of the Gene*, Volumes I and II, the Benjamin/Cummings Publishing Company, Inc., publisher, Menlo Park, Calif. (1987); Darnell et al., *Molecular Cell Biology*, Scientific American Books, Inc., Publisher, New York, N.Y. (1986); Lewin, *Genes II*, John Wiley & Sons, publishers, New York, N.Y. (1985); Old et al., *Principles of Gene Manipulation: An Introduction to Genetic Engineering*, 2d edition, University of California Press, publisher, Berkeley, Calif. (1981); Maniatis et al., *Molecular Cloning: A Laboratory Manual*, 2nd Ed. Cold Spring Harbor Laboratory, publisher, Cold Spring Harbor, N.Y. (1989); and Ausubel et al., *Current Protocols in Molecular Biology*, Wiley Press, New York, N.Y. (1989).

Definitions

By "cloning" is meant the use of in vitro recombination techniques to insert a particular gene or other DNA sequence into a vector molecule.

By "cDNA" is meant complementary or copy DNA produced from an RNA template by the action of RNA-dependent DNA polymerase (reverse transcriptase). Thus a "cDNA clone" means a duplex DNA sequence complementary to an RNA molecule of interest, carried in a cloning vector.

By "cDNA library" is meant a collection of recombinant DNA molecules containing cDNA inserts which comprise DNA copies of mRNA being expressed by the cell at the time the cDNA library was made. Such a cDNA library may be prepared by methods known to those of skill, and described, for example, in Ausubel et al., supra and Maniatis et al., supra. Generally, RNA is first isolated from the cells of an organism from whose genome it is desired to clone a particular gene. Preferred for the purpose of the present invention are mammalian, and particularly human, lymphocytic cell lines. A presently preferred vector for this purpose is the vaccinia virus WR strain.

By "vector" is meant a DNA molecule, derived, e.g., from a plasmid, bacteriophage, or mammalian or insect virus, into which fragments of DNA may be inserted or cloned. A vector will contain one or more unique restriction sites and may be capable of autonomous replication in a defined host or vehicle organism such that the cloned sequence is reproducible. Thus, by "DNA expression vector" is meant any autonomous element capable of directing the synthesis of a recombinant peptide. Such DNA expression vectors include bacterial plasmids and phages and mammalian and insect plasmids and viruses.

By "substantially pure" is meant a compound, e.g., a protein, a polypeptide, or an antibody, that is substantially free of the components that naturally accompany it. Generally, a compound is substantially pure when at least 60%, more preferably at least 75%, and most preferably at least 90% of the total material in a sample is the compound of interest. Purity can be measured by any appropriate method, e.g., column chromatography, polyacrylamide gel electrophoresis, or HPLC analysis. In the context of a nucleic acid, "substantially pure" means a nucleic acid sequence, segment, or fragment that is not immediately contiguous with (i.e., covalently linked to) both of the coding sequences with which it is immediately contiguous (i.e., one at the 5' end and one at the 3' end) in the naturally occurring genome of the organism from which the DNA of the invent on is derived.

A "fragment" of a molecule, such as any of the cDNA sequences of the present invention, is meant to refer to any contiguous nucleotide subset of the molecule. An "analog" of a molecule is meant to refer to a non-natural molecule substantially similar to either the entire molecule or a fragment thereof. A molecule is said to be "substantially similar" to another molecule if the sequence of amino acids in both molecules is substantially the same. Substantially similar amino acid molecules will possess a similar biological activity. As used herein, a molecule is said to be a "chemical derivative" of another molecule when it contains chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed, for example, in *Remington's Pharmaceutical Sciences,* 16th ed., Mack Publishing Co., Easton, Pa. (1980).

A "functional derivative" of a receptor chimera gene of the present invention is meant to include "fragments" or "analogues" of the gene, which are "substantially similar" in nucleotide sequence, and which encode a molecule possessing similar activity to, for example, a T cell, B cell, or Fc receptor chimera. Most preferably, the derivative possesses 90%, more preferably, 70%, and preferably 40% of the wild-type receptor chimera's activity. The activity of a functional chimeric receptor derivative includes specific binding (with its extracellular CD4 portion) to an HIV-infected cell and resultant destruction of that cell; in addition, the chimeric receptor does not render the receptor-bearing cell susceptible to HIV infection. Chimeric receptor activity may be tested using, e.g., any of the assays described herein.

A DNA sequence encoding the CD4 receptor chimera of the present invention, or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Maniatis, T., et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a CD4-receptor chimera encoding sequence) are said to be operably linked if the nature of -the linkage between the two DNA sequences does not (1) result in the introduction of a frame-shift mutation, (2) interfere with the ability of the promoter region sequence to direct the transcription of the receptor chimera gene sequence, or (3) interfere with the ability of the receptor chimera gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

The present invention encompasses the expression of a CD4-receptor chimera protein (or a functional derivative thereof) in either procaryotic or eukaryotic cells, although eukaryotic (and, particularly, human lymphocyte) expression is preferred.

Antibodies according to the present invention may be prepared by any of a variety of methods. For example, cells expressing the CD4-receptor chimera protein, or a functional derivative thereof, can be administered to an animal in order to induce the production of sera containing polyclonal antibodies that are capable of binding the chimera.

In a preferred method, antibodies according to the present invention are monoclonal antibodies. Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas,* Elsevier, N.Y., pp. 563–684 (1981)). In general, such procedures involve immunizing an animal with the CD4-receptor chimera antigen. The splenocytes of such animals are extracted and fused with a suitable myeloma cell line. Any suitable myeloma cell line may be employed in accordance with the present invention. After fusion, the resulting hybridoma cells are selectively maintained in HAT medium, and then cloned by limiting dilution as described by Wands et al. (*Gastroenterology* 80:225–232 (1981). The hybridoma cells obtained through such a selection are then assayed to identify clones which secrete antibodies capable of binding the chimera.

Antibodies according to the present invention also may be polyclonal, or, preferably, region specific polyclonal antibodies.

Antibodies against the CD4-receptor chimera according to the present invention may be used to monitor the amount of chimeric receptor (or chimeric receptor-bearing cells) in a patient. Such antibodies are well suited for use in standard immunodiagnostic assay known in the art, including such immunometric or "sandwich" assays as the forward sandwich, reverse sandwich, and simultaneous sandwich assays. The antibodies may be used in any number of combinations as may be determined by those of skill without undue experimentation to effect immunoassays of acceptable specificity, sensitivity, and accuracy.

Standard reference works setting forth general principles of immunology include Roitt, *Essential Immunology*, 6th ed., Blackwell Scientific Publications, Publisher, Oxford (1988); Kimball, *Introduction to Immunology*, 2d ed., Macmillan Publishing Co., Publisher, New York (1986); Roitt et al., *Immunology*, Gower Medical Publishing Ltd., Publisher, London, (1985); Campbell, "Monoclonal Antibody Technology," in Burdon et al., eds., *Laboratory Techniques in Biochemistry and Molecular Biology*, Volume 13, Elsevier, Publisher, Amsterdam (1984); Klein, *Immunology: The Science of Self-Nonself Discrimination*, John Wiley & Sons, Publisher, New York (1982); and Kennett et al., eds., *Monoclonal Antibodies. Hybridoma: A New Dimension In Biological Analyses*, Plenum Press, Publisher, New York (1980).

By "detecting" it is intended to include determining the presence or absence of a substance or quantifying the amount of a substance. The term thus refers to the use of the materials, compositions, and methods of the present invention for qualitative and quantitative determinations.

The antibodies and substantially purified antigen of the present invention are ideally suited for the preparation of a kit. Such a kit may comprise a carrier means being compartmentalized to receive in close confinement therewith one or more container means such as vials, tubes and the like, each of said container means comprising the separate elements of the assay to be used.

The types of assays which can be incorporated in kit form are many, and include, for example, competitive and non-competitive assays. Typical examples of assays which can utilize the antibodies of the invention are radioimmunoassays (RIA), enzyme immunoassays (EIA), enzyme-linked immunoadsorbent assays (ELISA), and immunometric, or sandwich, immunoassays.

By the term "immunometric assay" or "sandwich immunoassay," it is meant to include simultaneous sandwich, forward sandwich, and reverse sandwich immunoassays. These terms are well understood by those skilled in the art. Those of skill will also appreciate that antibodies according to the present invention will be useful in other variations and forms of assays which are presently known or which may be developed in the future. These are intended to be included within the scope of the present invention.

By "specifically recognizes and binds" is meant that the antibody recognizes and binds the chimeric receptor polypeptide but does not substantially recognize and bind other unrelated molecules in a sample, e.g., a biological sample.

By "therapeutic cell" is meant a cell which has been transformed by a CD4-receptor chimera of the invention so that it is capable of recognizing and destroying an HIV-infected cell; preferably such therapeutic cells are cells of the hematopoietic system.

By "extracellular" is meant having at least a portion of the molecule exposed at the cell surface. By "intracellular" is meant having at least a portion of the molecule exposed to the therapeutic cell's cytoplasm. By "transmembrane" is meant having at least a portion of the molecule spanning the plasma membrane. An "extracellular portion", an "intracellular portion" and a "transmembrane portion", as used herein, may include flanking amino acid sequences which extend into adjoining cellular compartments.

By "oligomerize" is meant to complex with other proteins to form dimers, trimers, tetramers, or other higher order oligomers. Such oligomers may be homo-oligomers or hetero-oligomers. An "oligomerizing portion" is that region of a molecule which directs complex (i.e., oligomer) formation.

By "cytolytic" is meant to be capable of destroying a cell (e.g., an HIV-infected cell) or to be capable of destroying an infective agent (e.g., an HIV virus).

By "immunodeficiency virus" is meant a retrovirus that, in wild-type form, is capable of infecting T4 cells of a primate host and possesses a viral morphogenesis and morphology characteristic of the lentivirus subfamily. The term includes, without limitation, all variants of HIV and SIV, including HIV-1, HIV-2, SIVmac, SIVagm, SIVmnd, SIVsmm, SIVman, SIVmand, and SIVcpz.

By "MHC-independent" is meant that the cellular cytolytic response does not require the presence of an MHC class II antigen on the surface of the targeted cell.

By a "functional cytolytic signal-transducing derivative" is meant a functional derivative (as defined above) which is capable of directing at least 40%, more preferably 70%, or most preferably at least 90% of the biological activity of the wild type molecule. As used herein, a "functional cytolytic signal-transducing derivative" may act by directly signaling the therapeutic cell to destroy a receptor-bound agent or cell (e.g., in the case of an intracellular chimeric receptor portion) or may act indirectly by promoting oligomerization with cytolytic signal transducing proteins of the therapeutic cell (e.g., in the case of a transmembrane domain). Such derivatives may be tested for efficacy, e.g., using the in vitro assays described herein.

By a "functional HIV envelope-binding derivative" is meant a functional derivative (as defined above) which is capable of binding any HIV envelope protein. Functional derivatives may be identified using, e.g., the in vitro assays described herein.

Therapeutic Administration

The transformed cells of the present invention are used for immunodeficiency virus therapy. Current methods of administering such transformed cells involve adoptive immunotherapy or cell-transfer therapy. These methods allow the return of the transformed immune-system cells to the bloodstream. Rosenberg, *Scientific American* 62 (May 1990); Rosenberg et al., *The New England Journal of Medicine* 323(9):570 (1990).

The pharmaceutical compositions of the invention may be administered to any animal which may experience the beneficial effects of the compounds of the invention. Foremost among such animals are humans, although the invention is not intended to be so limited.

DETAILED DESCRIPTION

The drawings will first be described.

BRIEF DESCRIPTION OF THE DRAWINGS

FIG. 4A and FIG. 4B sow Jurkat cells expressing CD4:ζ (solid line) or CD16:ζ (dashed line) which were exposed to anti-CD4 MAb Leu3a (phycoerythrin conjugate), followed by crosslinking with goat antibody to mouse IgG. The dotted line shows the response of uninfected cells to anti-CD3 MAb OKT3. FIGS. 4C and 4D show Jurkat cells expressing CD4:ζD15G (solid line); CD4:ζCD11G/D15G (dashes); or CD4:ζC11G (dots) which were treated and analyzed as in FIGS. 4A and 4B.

FIG. 5A: solid circles, CTL expressing CD4:ζ incubated with HeLa cells expressing gp120/41; open circles, CTL expressing CD4:ζ incubated with uninfected HeLa cells; solid squares, uninfected CTL incubated with HeLa cells expressing gp120/41; open squares, uninfected CTL incubated with uninfected HeLa cells. FIG. 5B: solid circles, CTL expressing CD4:η incubated with HeLa cells expressing gp120/41; open circles, CTL expressing CD4:γ incubated with HeLa cells expressing gp120/41; open squares, CTL expressing the C11G/D15G double mutant CD4:ζ chimera incubated with HeLa cells expressing gp120/41. FIG. 5C: Flow cytometric analysis of CD4 expression by the CTL used in FIG. 5B. To correct the target to effector ratios the percent of cells expressing CD4 chimera was determined by subtracting the scaled negative (uninfected) population by histogram superposition; for comparative purposes in this figure the uninfected cells were assigned an arbitrary threshold which gives roughly the same fraction positive for the other cell populations as would histogram subtraction.

FIG. 6A: solid circles, CTL expressing CD4:ζ incubated with HeLa cells expressing $CD16_{PI}$; open circles, CTL expressing CD4 incubated with HeLa cells expressing gp120; solid squares, CTL expressing CD16:ζ incubated with HeLa cells expressing gp120/41; open squares, CTL expressing $CD16_{PI}$ incubated with HeLa cells expressing gp120/41. FIG. 6B: solid circles, CTL expressing CD4:ζ incubated with Raji (MHC class II$^+$) cells; open circles, uninfected CTL cells incubated with RJ2.2.5 (MHC class II$^-$ Raji mutant) cells; solid squares, uninfected CTL incubated with Raji (MHC class II$^+$) cells; open squares, CTL expressing CD4:ζ incubated with RJ2.2.5 (MHC class II$^-$) cells. The ordinate scale is expanded.

FIG. 7A is a schematic diagram of the CD16:ζ fusion protein. The extracellular portion of the phosphatidylinositol-linked form of monomeric CD16 was joined to dimeric ζ just external to the transmembrane domain. The protein sequence at the fusion junction is shown at the bottom (SEQ ID NOS: 42, 43). FIG. 7B shows a flow cytometric analysis of calcium mobilization following crosslinking of the CD16:ζ chimera in either a TCR positive or TCR negative cell line. The mean ratio of violet to blue fluorescence (a measure of relative calcium ion concentration) among cell populations treated with antibodies at time 0 is shown. Solid squares, the response of Jurkat cells to anti-CD3 MAb OKT3; solid triangles, the response of CD16:ζ to anti-CD16 MAb 3G8 crosslinking in the REX33A TCR$^-$ mutant; open squares, the response to CD16:ζ crosslinking in the Jurkat TCR$^-$ mutant line JRT3.T3.5; open triangles, the response to CD16:ζ crosslinking in Jurkat cells; crosses, the response to nonchimeric CD16 in Jurkat cells; and dots, the response to nonchimeric CD16 in the REX33A TCR$^-$ cell line.

FIG. 8A shows the locations of the ζ deletion endpoints. Here as elsewhere mutations in ζ are represented by the original residue-location-mutant residue convention, so that D66*, for example, denotes replacement of Asp-66 by a termination codon. FIG. 8B shows cytolysis assay results of undeleted CD16:ζ and salient ζ deletions. Hybridoma cells expressing surface antibody to CD16 were loaded with $^{51}$Cr and incubated with increasing numbers of human cytolytic lymphocytes (CTL) infected with vaccinia recombinants expressing CD16:ζ chimeras. The percent of $^{51}$Cr released is plotted as a function of the effector (CTL) to target (hybridoma) cell ratio (e/t). Solid circles, cytolysis mediated by cells expressing CD16:ζ (mfi 18.7); solid squares, cytolysis mediated by cells expressing CD16:ζ Asp66* (mfi 940.2); open squares, cytolysis mediated by cells expressing CD16:ζGlu60* (mfi 16.0); open circles, cytolysis mediated by cells expressing CD16:ζTyr51* (mfi 17.4); solid triangles, cytolysis mediated by cells expressing CD16:ζPhe34* (mfi 17.8); and open triangles, cytolysis mediated by cells expressing nonchimeric CD16 (mfi 591). Although in this experiment the expression of CD16:ζAsp66* was not matched to that of the other fusion proteins, cytolysis by cells expressing CD16:ζ at equivalent levels in the same experiment gave results essentially identical to those shown by cells expressing CD16:ζAsp66.

FIG. 9A is a schematic diagram of the monomeric bipartite and tripartite chimeras. At the top is the CD16:ζ construct truncated at residue 65 and lacking transmembrane Cys and Asp residues. Below are the CD16:CD5:ζ and CD16:CD7:ζ constructs and related controls. The peptide sequences of the intracellular domains are shown below (SEQ ID NOS: 45–47). FIG. 9B shows the cytolytic activity of monomeric chimera deletion mutants. The cytolytic activity of cells expressing CD16:ζ (solid circles; mfi 495) was compared to that of cells expressing CD16:ζAsp66* (solid squares; mfi 527) or the mutants CD16:ζCys11Gly/Asp25Gly/Asp66*, (open squares; mfi 338) and CD16:δCys11Gly/Asp15Gly/Glu66* (filled triangles; mfi 259). FIG. 9C shows the cytolytic activity mediated by tripartite fusion proteins. Solid triangles, CD16:ζAsp66*; open squares, CD16:5:ζ(48–65); solid squares CD16:7:ζ(48–65); open triangles, CD16:7:ζ (48–59); open circles, CD16:5; solid circles, CD16:7. FIG. 9D shows calcium mobilization by mutant and tripartite chimeras in the TCR negative Jurkat JRT3.T3.5 mutant cell line. Open circles, response of cells expressing dimeric CD16:ζAsp66*; solid squares, response of cells expressing CD16:ζCys11Gly/Asp15Gly/Asp66*; open squares, response of cells expressing CD16:δCys11Gly/Asp15Gly/Glu60*; solid triangles, response of cells expressing CD16:7:δ(48–65); and open triangles, response of cells expressing CD16:ζ(48–59).

FIGS. 10A and 10B show cytolytic activity and FIG. 10C shows calcium ion mobilization mediated by chimeras-bearing point mutations near the carboxyl terminal tyrosine (Y62). FIGS. 10A and 10D represent data collected on cells expressing low and high amounts, respectively, of the CD16:ζ fusion proteins. Identical symbols are used for the calcium mobilization and cytolysis assays, and are shown in one letter code at right. Solid circles, cells expressing CD16:ζ (mfi in A, 21; B, 376); solid squares, cells expressing CD16:7:ζ(48–65) (mfi A, 31; B, 82); open squares, CD16:7:ζ(48–65)Glu60Gln (mfi A, 33; B, 92), crosses, CD16:7:ζ(48–65)Asp63Asn (mfi A, 30; B, 74); solid triangles, CD16:7:ζ(48–65)Tyr62Phe (mfi A, 24; B, 88); open circles, CD16:7:ζ(48–65)Glu61Gln (mfi A, 20; B, 62); and open triangles, CD16:7:ζ(48–65)Tyr62Ser (mfi B, 64). FIGS. 10D and 10E show cytolytic activity and FIG. 10F shows calcium ion mobilization by chimeras bearing point mutations near the amino terminal tyrosine (Y51). Identical symbols are used for the calcium mobilization and cytolysis assays and are shown at right. Solid circles, cells expressing CD16:ζ (mfi in D, 21.2; in E, 672); solid squares, cells expressing CD16:7:ζ(48–65) (mfi D, 31.3; E, 179); solid triangles, CD16:7:ζ(48–65)Asn48Ser (mfi D, 22.4; E, 209); open squares, CD16:7:ζ(48–65) Leu50Ser (mfi D, 25.0; E, 142); and open triangles, CD16:7:ζ(48–65)Tyr51Phe (mfi D, 32.3; E, 294).

FIG. 11A is a schematic diagram of chimeras formed by dividing the ζ intracellular domain into thirds and appending them to the transmembrane domain of a CD16:7 chimera. The sequences of the intracellular domains are shown below (SEQ ID NOS: 48–50), with shared residues boxed, and related residues denoted by asterisks. FIG. 11B shows the cytolytic potency of the three ζ subdomains. Solid circles, cells expressing CD16:ζ (mfi 476); solid squares, CD16:7:ζ (33–65) (mfi 68); open squares, CD16:7:ζ(71–104) (mfi 114); and solid triangles, CD16:7:ζ(104–138) (mfi 104).

FIG. 13A shows the ratio of violet to blue fluorescence emitted by cells loaded with the calcium sensitive fluorophore Indo-1 shown as a function of time following crosslinking of the CD16 extracellular domain with antibodies. FIG. 13B shows a similar analysis of the increase in ratio of violet to blue fluorescence of cells bearing CD4:FcRγII chimeras, following crosslinking with antibodies.

FIG. 14A shows the percent of $^{51}$Cr released from anti-CD16 hybridoma (target) cells when the cells are exposed to increasing numbers of cytotoxic T lymphocytes expressing CD16:FcRγII chimeras (effector cells). FIG. 14B shows a similar analysis of cytotoxicity mediated by CD4:FcRγII chimeras against target cells expressing HIV envelope glycoproteins.

FIG. 15A is a schematic diagram of the deletion constructs. FIGS. 15B and 15C shows calcium mobilization and cytolysis by carboxyl-terminal deletion variants of CD16:FcRγII A. FIGS. 15D and 15E show calcium mobilization and cytolysis by tripartite chimeras bearing progressively less of the amino terminus of the intracellular tail of CD16:FcRγII A.

FIG. 16 (SEQ ID NO: 24) shows the amino acid sequence of the CD3 delta receptor protein; the boxed sequence represents a preferred cytolytic signal transducing portion.

FIG. 17 (SEQ ID NO: 25) shows the amino acid sequence of the T3 gamma receptor protein; the boxed sequence represents a preferred cytolytic signal transducing portion.

FIG. 18 (SEQ ID NO: 26) shows the amino acid sequence of the mb1 receptor protein; the boxed sequence represents a preferred cytolytic signal transducing portion.

FIG. 19 (SEQ ID NO: 27) shows the amino acid sequence of the B29 receptor protein; the boxed sequence represents a preferred cytolytic signal transducing portion.

FIG. 20 shows a schematic diagram of the CD4 chimeras. Molecule "A" is CD4(D1–D4):Ig:CD7; molecule "B" is CD4(D1,D2):Ig:CD7; molecule "C" is CD4(D1–D4):Ig:CD7:ζ; molecule "D" is CD4(D1,D2):Ig:CD7:ζ; and molecule "E" is CD4:ζ. The extracellular domain of the human CD4 molecule corresponding to amino acids 1–394 of the precursor was joined by a BamHI site to the hinge, CH1, and CH2 domains of human IgG1 as described previously (Zettlmeissl et al., *DNA Cell Biol.* 9:347 (1990)) except that a cDNA version of the human Ig sequences was used to allow expression in vaccinia virus recombinants. The two-domain version of the CD4 chimeras were created by insertion of a BamHI adaptor at the unique NheI site (corresponding to amino acid 200) in the CD4 precursor cDNA. The membrane attachment sequences consisted of 22 residues from the first exon of human membrane-bound IgG1 followed by CD7 residues 146–203. Amino acids 55 through 163 of ζ served as the trigger motif of the tetrapartite constructs (C and D). In tetrapartite constructs containing the ζ chain, intracellular expression of ζ was documented with a commercially available antibody against the intracellular domain (Coulter).

Figure 21:
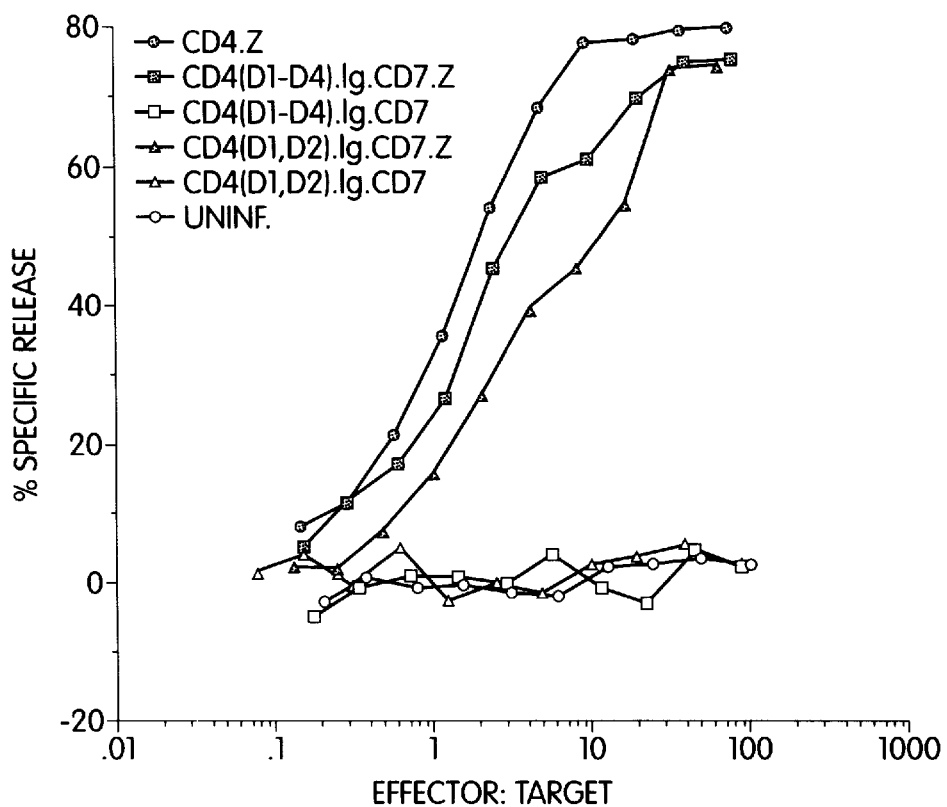

FIG. 21 shows cytolysis of target cells expressing the HIV-1 envelope glycoprotein mediated by the cytotoxic T-cell clone, WH3, expressing various CD4-derived chimeras as effector molecules. For cytotoxicity assays, the human CD8+ CD4− HLA B44 restricted T cell line, WH3, was maintained in IMDM supplemented with 10% human serum as previously described herein. The cells were stimulated with gamma-irradiated (3000 rad) B44-bearing mononuclear cells and phytohemagglutinin (PHA) at 1 μg/ml. After one day of stimulation, the PHA was diluted to 0.5 μg/ml by addition of fresh medium; after 3 days the medium was changed completely. Cells were grown for at least 10 days before use in cytotoxicity assays. Cells were infected with the appropriate recombinant vaccinia viruses as described herein for vPE16. Infections were allowed to proceed for an additional 3–4 hours in complete medium after which cells were harvested by centrifugation and resuspended at a density of 1×10$^7$/ml. 100 μl were added to each well of a U-bottom microtiter plate containing 100 μl per well of complete medium and diluted in 2-fold serial steps. Two wells for each sample did not contain lymphocytes, to allow spontaneous chromium release and total chromium uptake to be measured. The target cells, HeLa subline S3 (HeLa-S3, ATCC) were infected as above in 10 cm dishes with vPE16. 10$^6$ infected cells were detached with PBS and 1 mM EDTA, centrifuged and resuspended in 100 μl of $^{51}$Cr sodium chromate (1 mCi/ml in PBS) for 1 hour at 37° C. and then washed three times with PBS. 100 μl of labelled target cells were added to each well. The microtiter plate was spun at 750×g for 1 minute and incubated for 4 hours at 37° C. At the end of the incubation period, the cells in each well were resuspended by gentle pipetting, a sample removed to determine the total counts incorporated and the microtiter plate was spun at 750×g for 1 min. Aliquots (100 μl) of the supernatant were removed and counted in a gamma ray scintillation counter. The effector:target ratio was corrected for the percent of cells infected as measured by flow cytometry.

Figure 22:
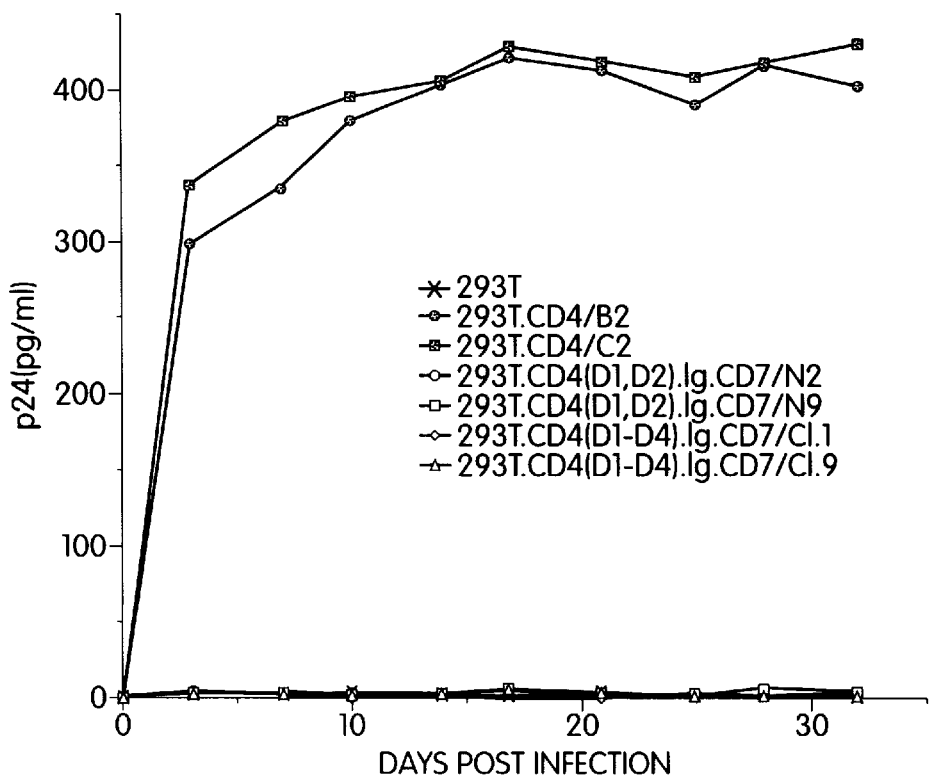

FIG. 22 shows replication of HIV-1 in transfectant cell lines. Cell lines stably expressing wild type CD4 and various recombinant chimeras were established in a subline of the human embryonal kidney cell line 293. A virus stock of the HIV-1 IIIB isolate was prepared with a titer of ≈10$^6$ infectious particles/ml as measured by end-point dilution analysis using the human T-cell line C8166 as an indicator. Infections were carried out at an approximate MOI of 1 for a period of 8–12 hours at 37° C. On the following day the cells were washed with PBS three times, trypsinized, replated in new dishes and the culture supernatant sampled for p24 titer (designated day 0). At 3–4 day intervals thereafter, cell culture supernatants were collected and retained for p24 analysis. The cells were resupplied with fresh medium containing hygromycin B at a concentration of 100 μg/ml. Analysis of culture supernatants was carried out using a commercial ELISA-based HIV-1 p24 antigen assay kit (Coulter) according to the instructions supplied by the manufacturer. Results are representative of two independent experiments of similar duration.

FIG. 23 shows the nucleic acid (SEQ ID NO: 29) and amino acid sequence of the D1–D4 domains of CD4 (CD4 Ban).

FIG. 24 shows the nucleic acid (SEQ ID NO: 30) and amino acid (SEQ ID NO: 31) sequence of the D1–D2 domains of CD4 (CD4 Nhe).

FIG. 25 shows the nucleic acid (SEQ ID NO: 32) and amino acid (SEQ ID NO: 33) sequence of the hinge, CH2, and CH3 domains of human IgG1 (Igh23 Ban).

FIG. 26 shows the nucleic acid (SEQ ID NO: 34) and amino acid (SEQ ID NO: 35) sequence of the transmembrane domain of CD7 (TM7 Bam Mlu).

FIG. 27 shows the nucleic acid (SEQ ID NO: 36) and amino acid (SEQ ID NO: 37) sequence of the intracellular domain of zeta (Zeta Mlu Not).

FIG. 28 shows the DNA sequence (SEQ ID NO: 51) and primary amino acid sequence (SEQ ID NO: 52) of a synthetic alpha helix.

EXAMPLE I

Construction of Human IgG1:Receptor Chimeras

Human IgG1 heavy chain sequences were prepared by joining sequences in the $C_H3$ domain to a cDNA fragment derived from the 3' end of the transmembrane form of the antibody mRNA. The 3' end fragment was obtained by polymerase chain reaction using a tonsil cDNA library as substrate, and oligonucleotides having the sequences:

CGC GGG GTG ACC GTG CCC TCC AGC AGC TTG GGC (SEQ ID NO: 7) and

CGC GGG GAT CCG TCG TCC AGA GCC CGT CCA GCT CCC CGT CCT GGG CCT CA (SEQ ID NO: 8), corresponding to the 5' and 3' ends of the desired DNA fragments respectively. The 5' oligo is complementary to a site in the $C_H1$ domain of human IgG1, and the 3' oligo is complementary to a site just 5' of the sequences encoding the membrane spanning domain. The PCR product was digested with BstXI and BamHI and ligated between BstXI and BamHI sites of a semisynthetic IgG1 antibody gene bearing variable and constant regions. Following the insertion of the BstXI to BamHI fragment, the amplified portions of the construct were replaced up to the SmaI site in $C_H3$ by restriction fragment interchange, so that only the portion between the SmaI site and the 3' oligo was derived from the PCR reaction.

To create a human IgG1:ζ chimeric receptor, the heavy chain gene ending in a BamHI site was joined to the BamHI site of the ζ chimera described below, so that the antibody sequences farmed the extracellular portion. Flow cytometry of COS cells transfected with a plasmid encoding the chimera showed high level expression of antibody determinants when an expression plasmid encoding a light chain cDNA was cotransfected, and modest expression of antibody determinants when the light chain expression plasmid was absent.

Similar chimeras including human IgG1 fused to η or γ (see below), or any signal-transducing portion of a T cell receptor or Fc receptor protein may be constructed generally as described above using standard techniques of molecular biology.

To create a single transcription unit which would allow both heavy end light chains to be expressed from a single promoter, a plasmid encoding a bicistronic mRNA was created from heavy and light chain coding sequences, and the 5' untranslated portion of the mRNA encoding the 78 kD glucose regulated protein, otherwise known as grp78, or BiP. grp78 sequences were obtained by PCR of human genomic DNA using primers having the sequences:

CGC GGG CGG CCG CGA CGC CGG CCA AGA CAG CAC (SEQ ID NO: 9) and

CGC GTT GAC GAG CAG CCA GTT GGG CAG CAG CAG (SEQ ID NO: 10)

at the 5' and 3' ends respectively. Polymerase chain reactions with these oligos were performed in the presence of 10% dimethyl sulfoxide. The fragment obtained by PCR was digested with NotI and HincII and inserted between NotI and HpaI sites downstream from human IgG1 coding sequences. Sequences encoding a human IgG kappa light chain cDNA were then inserted downstream from the grp78 leader, using the HincII site and another site in the vector. The expression plasmid resulting from these manipulations consisted of the semisynthetic heavy chain gene, followed by the grp78 leader sequences, followed by the kappa light chain cDNA sequences, followed by polyadenylation signals derived from an SV40 DNA fragment. Transfection of COS cells with the expression plasmid gave markedly improved expression of heavy chain determinants, compared to transfection of plasmid encoding heavy chain determinants alone.

To create a bicistronic gene comprising a heavy chain/receptor chimera and a light chain, the upstream heavy chain sequences can be replaced by any chimeric heavy chain/receptor gene described herein.

EXAMPLE II
Construction of CD4 Receptor Chimeras

Figure 1A:
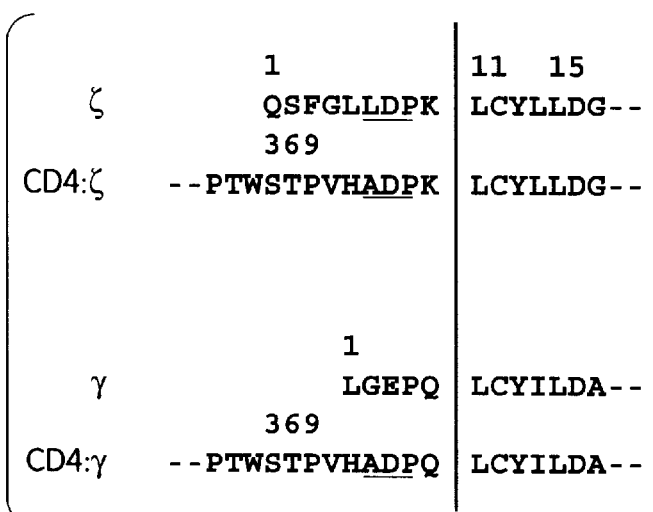
FIG. 1A presents the amino acid sequence about the site of fusion between CD4 (residues 1–369) and different receptor chains (SEQ ID NOS: 38–41). The underlined sequence shows the position of the amino acids encoded within the BamHI site used for fusion construction. The beginning of the transmembrane domain is marked with a vertical bar. The η sequence is identical to the ζ sequence at the amino terminus, but diverges at the carboxyl terminus (Jin et al., *Proc. Natl. Acad. Sci. USA* 87:3319–3323 (1990)).
Figure 1B:
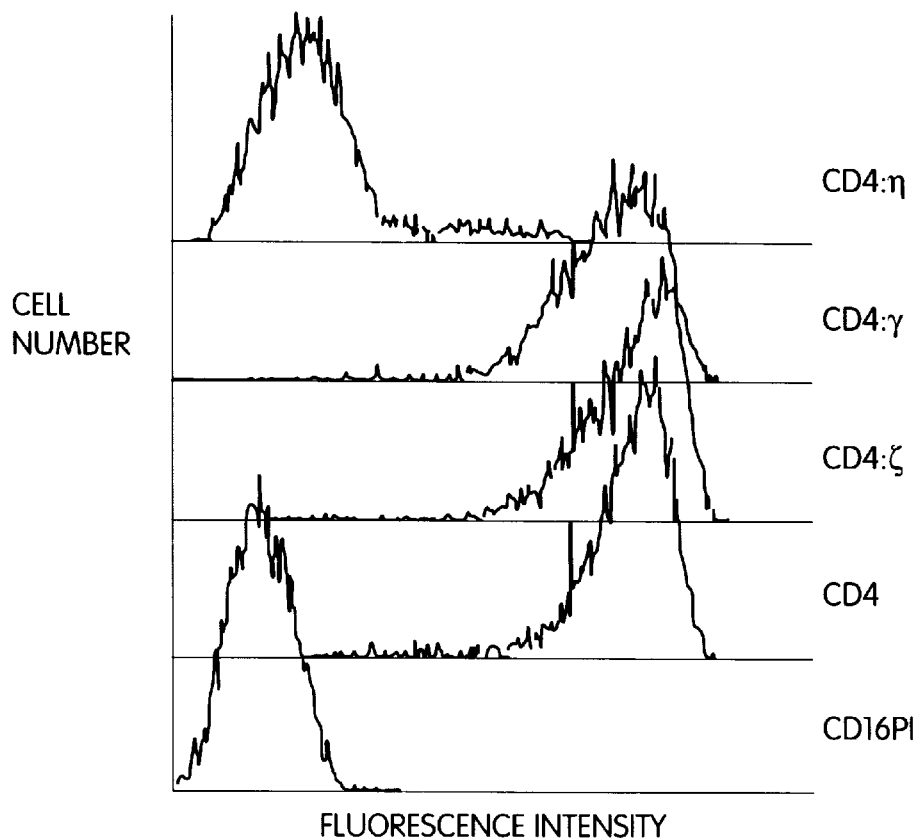
FIG. 1B presents flow cytometric analysis of surface expression of CD4, CD4:ζ, CD4:γ and CD4:η in CV1 cells. Cells were infected with virus expressing CD4 chimeras or $CD16_{PI}$, incubated for 9 hours at 37° C., and stained with phycoerythrin-conjugated anti-CD4 MAb Leu3A.

Human ζ (Weissman et al., *Proc. Natl. Acad. Sci. USA* 85:9709–9713 (1983b)) and γ (Küster et al., *J. Biol. Chem.* 265:6448–6452 (1990)) cDNAs were isolated by polymerase chain reaction from libraries prepared from the HPB-ALL tumor cell line (Aruffo et al., *Proc. Natl. Acad. Sci. USA* 84:8573–8577 (1987b)) and from human natural killer cells, while η cDNA (Jin et al., *Proc. Natl. Acad. Sci. USA* 87:3319–3323 (1990)) was isolated from a murine thymocyte library. ζ, η and γ cDNAs were joined to the extracellular domain of an engineered form of CD4 possessing a BamHI site just upstream of the membrane spanning domain (Aruffo et al., *Proc. Natl. Acad. Sci. USA* 84:8573–8577 (1987b); Zettlmeissl et al., *DNA Cell Biol.* 9347–353 (1990)) which was joined to the BamHI site naturally present in the ζ and η cDNAs at a similar location a few residues upstream of the membrane spanning domain (SEQ ID NOS: 1, 3, 4 and 6). To form the fusion protein with γ a BamHI site was engineered into the sequence at the same approximate location (FIG. 1; SEQ ID NO: 2 and 5). The gene fusions were introduced into a vaccinia virus expression plasmid bearing the *E. coli* gpt gene as a selectable marker, and inserted into the genome of the vaccinia WR strain by homologous recombination and selection for growth in mycophenolic acid (Falkner et al., *J. Virol.* 62:1849–1854 (1988); Boyle et al., *Gene* 65:123–128 (1988)). Flow cytometric analysis showed that the vaccinia recombinants direct the abundant production of CD4:ζ and CD4:γ fusion proteins at the cell surface, whereas the expression of CD4:η is substantially weaker (FIG. 1B). The latter finding is consistent with a recent report that transfection of an n cDNA expression plasmid into a murine hybridoma cell line gave substantially less expression than transfection of a comparable ζ expression plasmid (Clayton et al., *J. Exp. Med.* 172:1243–1253 (1990)). Immunoprecipitation of cells infected with the vaccinia recombinants revealed that the fusion proteins form covalent dimers, unlike the naturally occurring CD4 antigen. The molecular masses of the monomeric CD4:ζ and CD4:γ fusion proteins and native CD4 were found to be 63, 55 and 53 kD respectively. The larger masses of the fusion proteins are approximately consistent with the greater length of the intracellular portion, which exceeds that of native CD4 by 75 (CD4:ζ or 5 (CD4:γ) residues.

EXAMPLE III
CD4 Chimeras can Associate with Other Receptor Chains

Cell surface expression of the macrophage/natural killer cell form of human FcγRIII ($CD16_{TM}$) on transfectants is facilitated by cotransfection with murine (Kurosaki et al., *Nature* 342:805–807 (1989)) or human (Hibbs et al., *Science* 246:1608–1611 (1989)) γ, as well as by human ζ (Lanier et al., *Nature* 342:803–805 (1989)).

Figure 2:
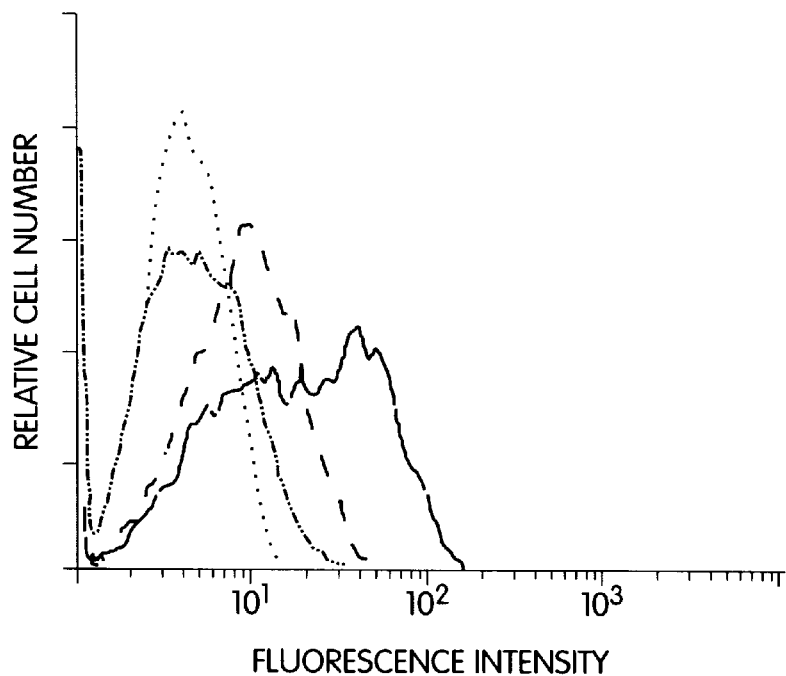
FIG. 2 shows surface expression of $CD16_{TM}$ following coinfection of $CD16_{TM}$ alone (dense dots), or coinfected with virus expressing CD4:γ (dashes) or CD4:ζ (solid line). Sparse dots, cells infected with CD4:ζ alone, stained with 3G8 (Fleit et al., *Proc. Natl. Acad. Sci. USA* 79:3275–3279 (1982)) (anti-CD16 MAb).

Consistent with these reports, expression of the chimeras also allowed surface expression of $CD16_{TM}$) when delivered to the target cell either by cotransfection or by coinfection with recombinant vaccinia viruses (FIG. 2). The promotion of $CD16_{TM}$ surface expression by ζ was more pronounced than promotion by γ (FIG. 2) in the cell lines examined, whereas native CD4 did not enhance $CD16_{TM}$ surface expression.

EXAMPLE IV
Asp ζ Mutants do not Coassociate with Fc Receptor

Figure 3:
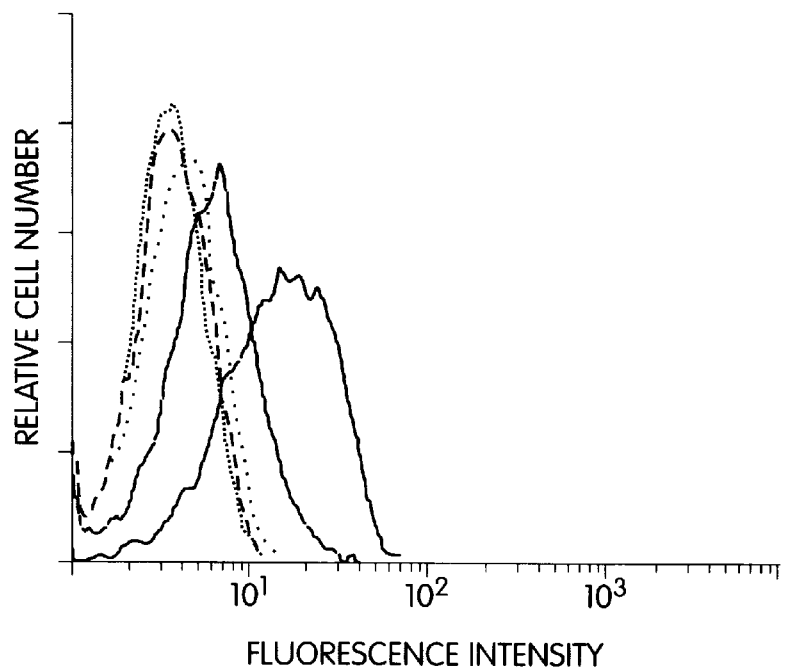
FIG. 3 shows surface expression of $CD16_{TM}$ following coinfection by viruses expressing $CD16_{TM}$ and the following ζ chimeras: CD4:ζ (thick line), CD4:ζ C11G (solid line); CD4:ζ (dashed line); CD4:ζ C11G/D15G (dense dots); no coinfection ($CD16_{TM}$ alone, sparse dots). Cells were incubated with anti-CD16 MAb 3G8 and phycoerythrin-conjugated Fab'$_2$ goat antibodies to mouse IgG. The level of expression of the ζ chimeras was essentially identical for the different mutants analyzed, and coinfection of cells with viruses expressing $CD16_{TM}$ and ζ chimeras did not appreciably alter surface expression of the chimeras.

To create chimeras which would not associate with existing antigen or Fc receptors, mutant ζ fusion proteins which lacked either the intramembranous Asp or intramembranous Cys residue or both were prepared. Flow cytometry showed that the intensity of cell surface expression by the different mutant chimeras was not appreciably different from the unmutated precursor, and immunoprecipitation experiments showed that total expression by the chimeras was similar. As expected, the mutant chimeras lacking the transmembrane cysteine residue were found not to form disulfide linked dimers. The two mutant chimeras lacking Asp were incapable of supporting the surface expression of $CD16^{TM}$, whereas the monomeric chimeras lacking Cys but bearing Asp allowed $CD16_{TM}$ to be coexpressed, but at lower efficiency than the parental dimer (FIG. 3).

Figure 4A:
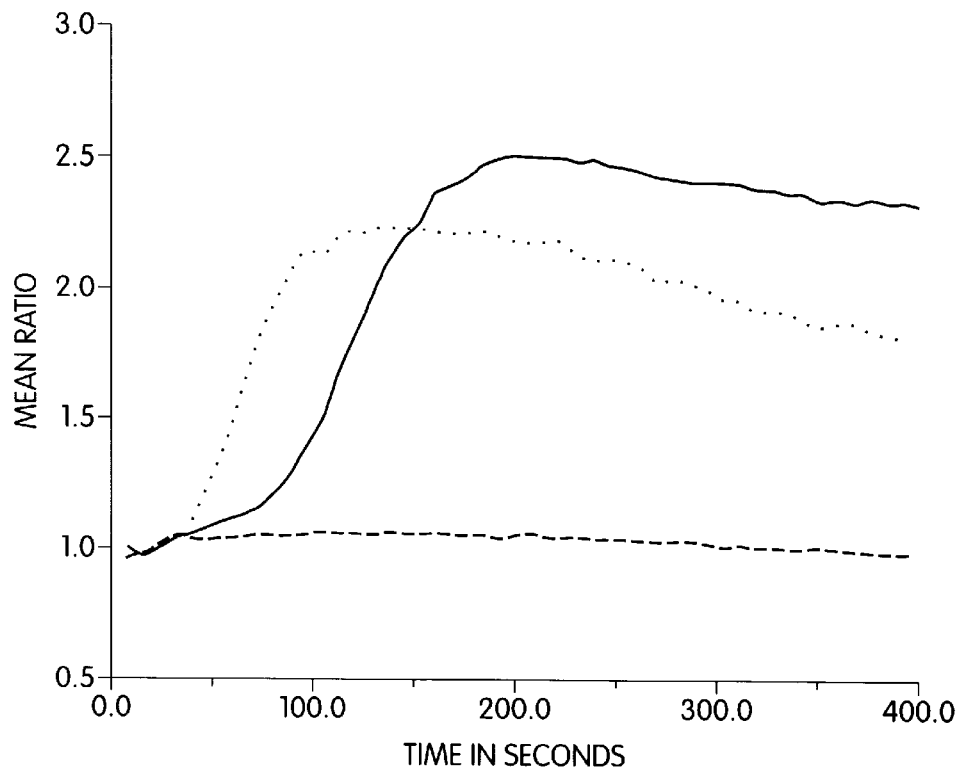
FIGS. 4A–D shows increased intracellular free calcium ion follows crosslinking of mutant ζ chimeras in a T cell line. Jurkat E6 cells (Weiss et al., *J. Immunol.* 133:123–128 (1984)) were infected with recombinant vaccinia viruses and analyzed by flow cytometry. The results shown are for the gated CD4$^+$ population, so that only cells expressing the relevant chimeric protein are analyzed. The mean ratio of violet to blue Indo-1 fluorescence reflects the intracellular free calcium concentration in the population as a whole and the percentage of responding cells reflects the fraction of cells which exceed a predetermined threshold ratio (set so that 10% of untreated cells are positive).
Figure 4B:
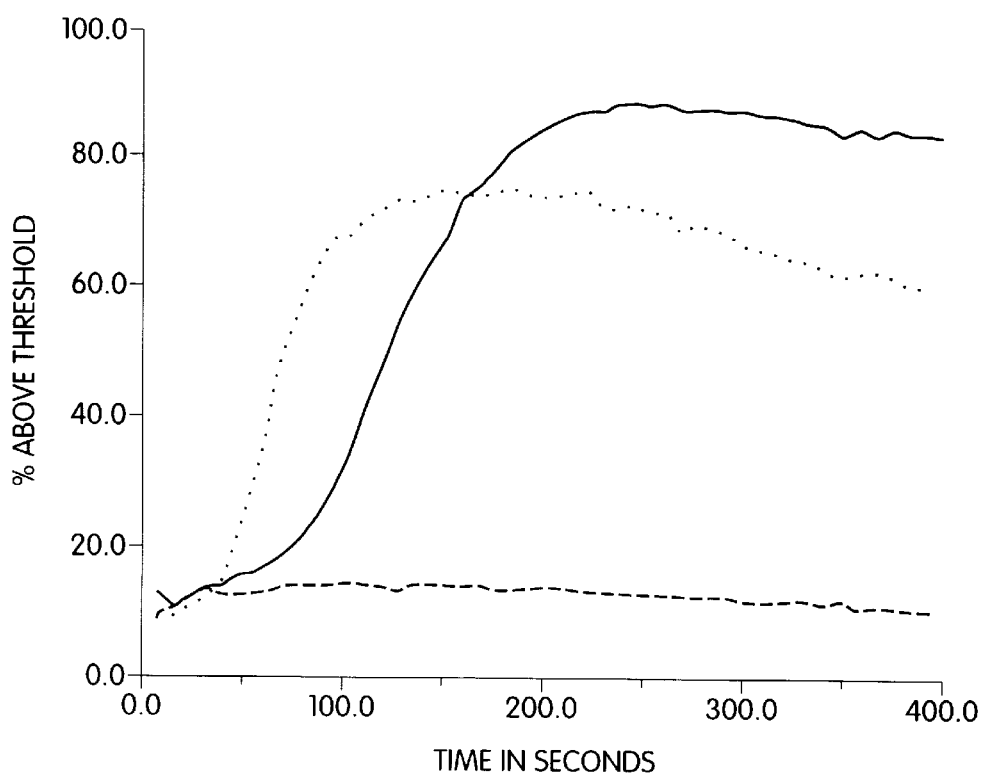
Figure 4C:
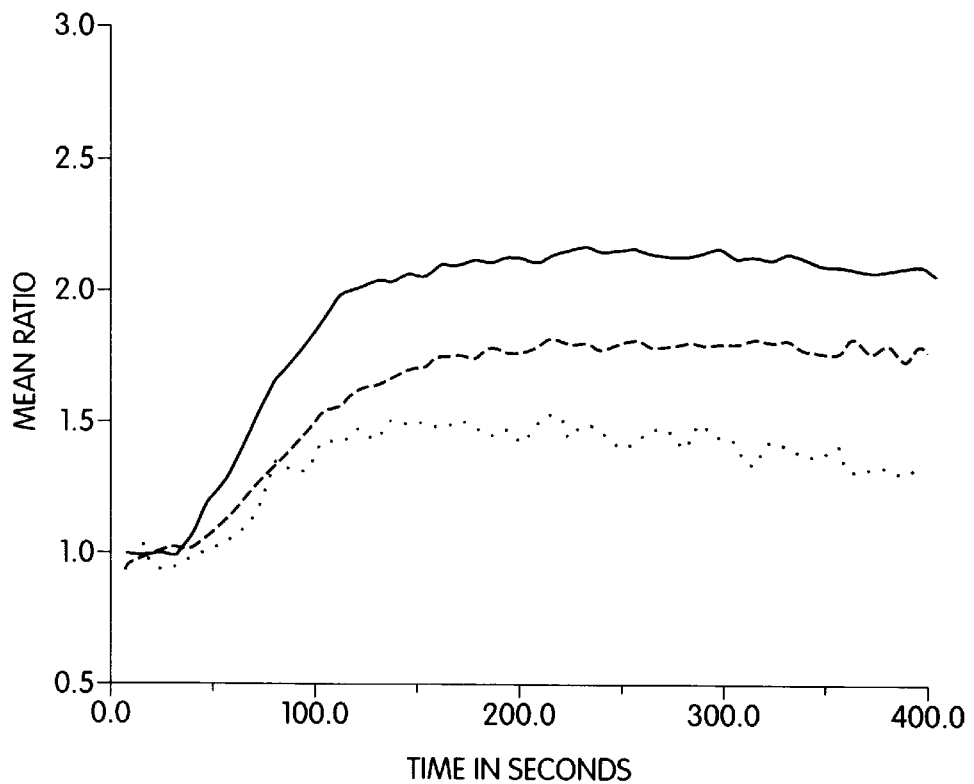
Figure 4D:
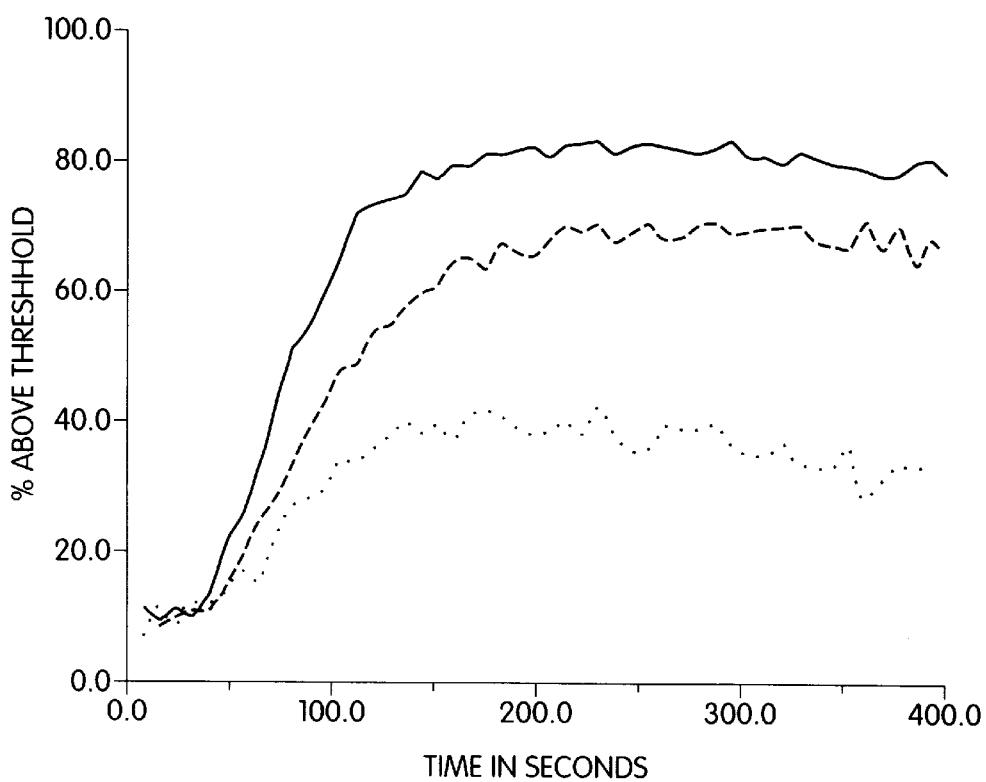

EXAMPLE V
Mutant Receptors Retain the Ability to Initiate a Calcium Response To determine whether crosslinking of the fusion proteins would allow the accumulation of free intracellular calcium in a manner similar to that known to occur with the T cell antigen receptor, cells of the human T cell leukemia line, Jurkat E6 (ATCC Accessior Number TIB 152, American Type Culture Collection, Rockville, Md.), were infected with the vaccinia recombinants and the relative cytoplasmic calcium concentration following crosslinking of the extracellular domain with antibodies was measured. Flow cytometric measurements were performed with cells loaded with the calcium sensitive dye Indo-1 (Grynkiewicz et al.,*J. Biol. Chem.* 260:3340–3450 (1985); Rabinovitch et al., *J. Immunol.* 137:952–961 (1986)). FIGS. 4A–D shows the results of calcium flux experiments with cells infected with CD4:ζ and the $Asp^-$ and $Cys^-$ mutants of ζ. Crosslinking of the chimeras, reproducibly increased intracellular calcium. CD4:η and CD4:γ similarly allowed accumulation intracellular calcium in infected cells. Jurkat cells express low levels of CD4 on the cell surface, however, crosslinking of the native CD4 in the presence or absence of CD16:ζ does not alter intracellular calcium levels (FIGS. 4A–B).

EXAMPLE VI
CD4:ζ, η, and γ Chimeras Mediate Cytolysis of Targets Expressing HIV gp120/41

To determine whether the chimeric receptors would trigger cytolytic effector programs, a model target:effector system based on CD4 recognition of the HIV envelope gp120/gp41 complex was created. HeLa cells were infected with recombinant vaccinia viruses expressing gp120/gp41

Figure 5A:
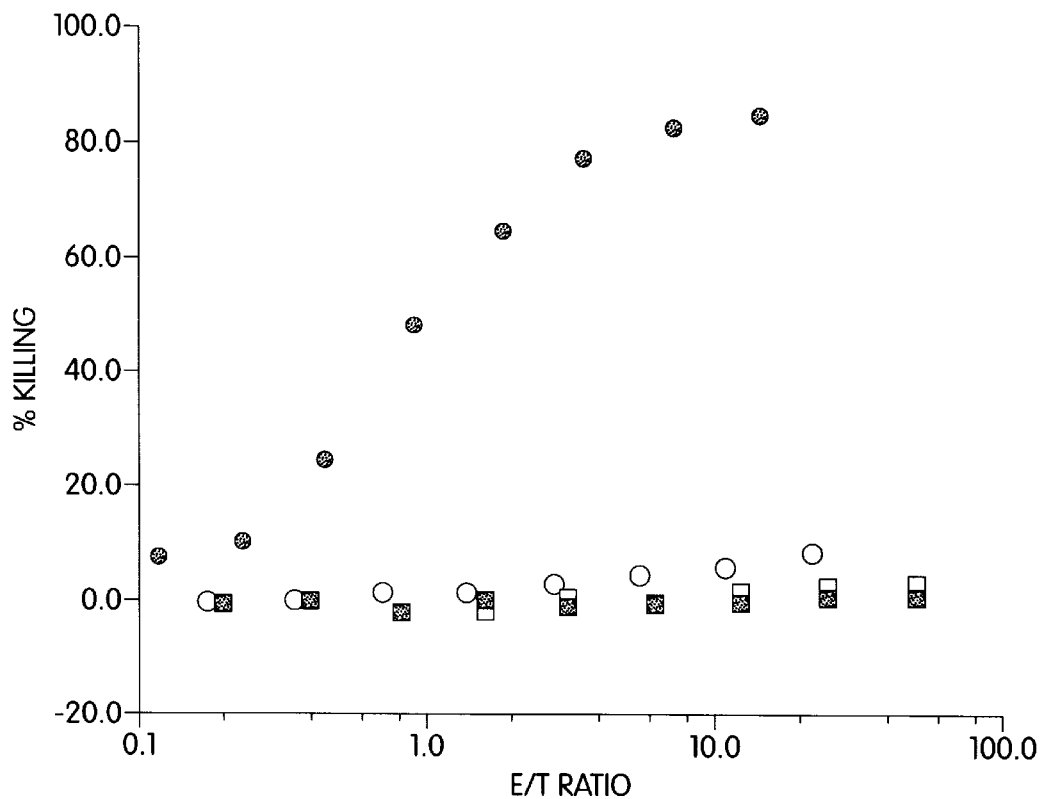
FIGS. 5A–C shows that CD4:ζ, CD4:η, and CD4:γ receptors allow cytolytic T lymphocytes (CTL) to kill targets expressing HIV-1 gp120/41.
Figure 5B:
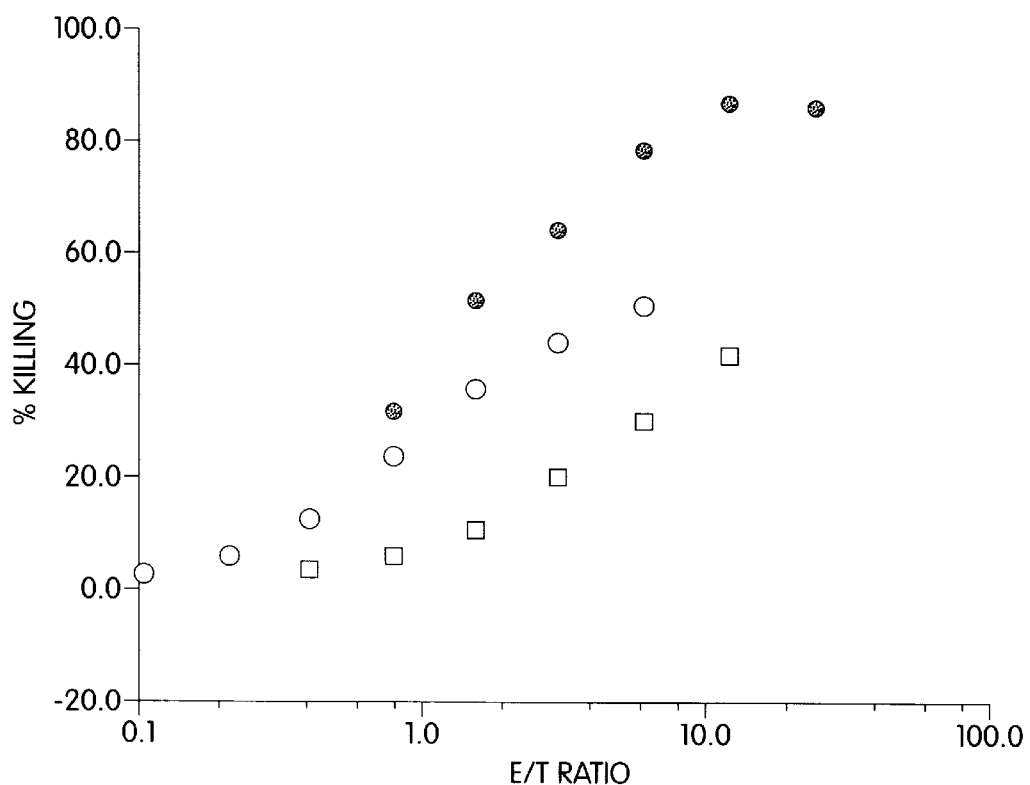
Figure 5C:
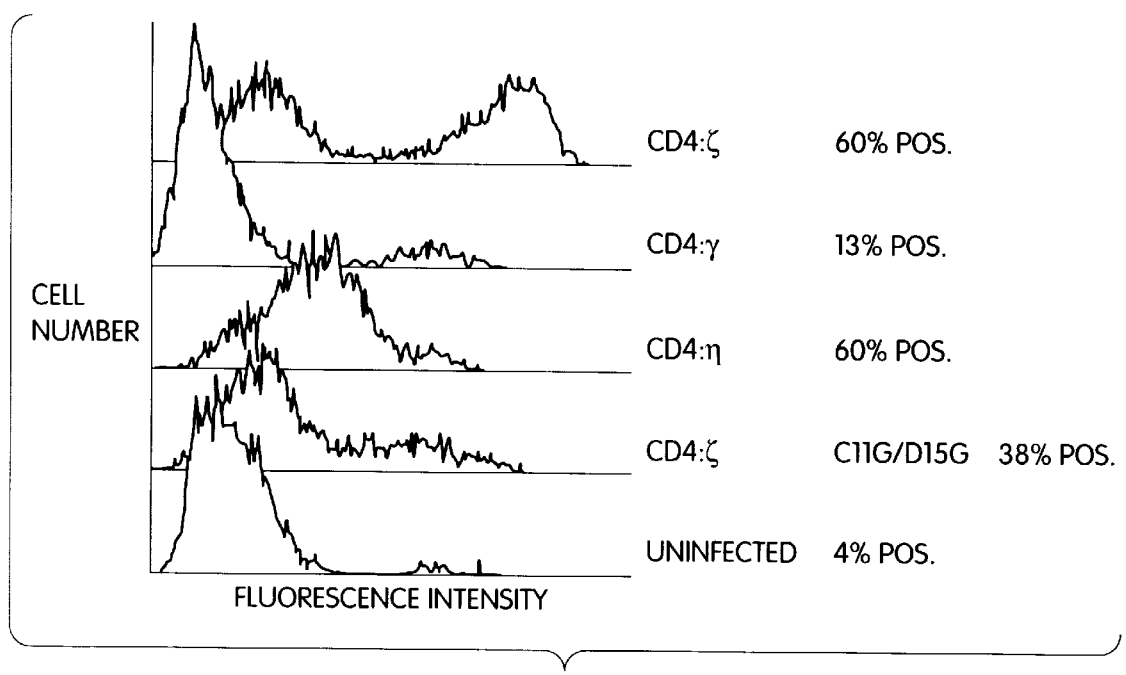

(Chakrabarti et al., *Nature* 320:535–537 (1986); Earl et al., *J. Virol.* 64:2448–2451 (1990)) and labeled with $^{51}$Cr. The labeled cells were incubated with cells from a human allospecific (CD8$^+$, CD4$^-$) cytotoxic T lymphocyte line which had been infected with vaccinia recombinants expressing the CD4:ζ, CD4:η, or CD4:γ chimeras, or the CD4:ζCys11Gly:Asp15Gly double mutant chimera. FIGS. 5A–C shows that HeLa cells expressing gp120/41 were specifically lysed by cytotoxic T lymphocytes (CTL) expressing CD4 chimeras. Uninfected HeLa cells were not targeted by CTL armed with CD4:ζ chimeras, and HeLa cells expressing gp120/41 were not recognized by uninfected CTL. To compare the efficacy of the various chimeras, the effector to target ratios were corrected for the fraction of CTL expressing CD4 chimeras, and for the fraction of HeLa cells expressing gp120/41, as measured by flow cytometry. FIG. 5C shows a cytometric analysis of CD4 expression by the CTL used in the cytolysis experiment shown in FIGS. 5A and 5B. Although the mean density of surface CD4:ζ greatly exceeded the mean density of CD4:η, the cytolytic efficiencies of cells expressing either form were similar. Correcting for the fraction of targets expressing gp202, the efficiency of cytolysis mediated by CD4:ζ and CD4:η proteins are comparable to the best efficiencies reported for specific T cell receptor target:effector pairs (the mean effector to target ratio for 50% release by T cells expressing CD4:ζ was 1.9±0.99, n=10. The CD4:γ fusion was less active, as was the CD4:ζ fusion lacking the transmembrane Asp and Cys residues. However in both cases significant cytolysis was observed (FIGS. 5B–C).

Figure 6A:
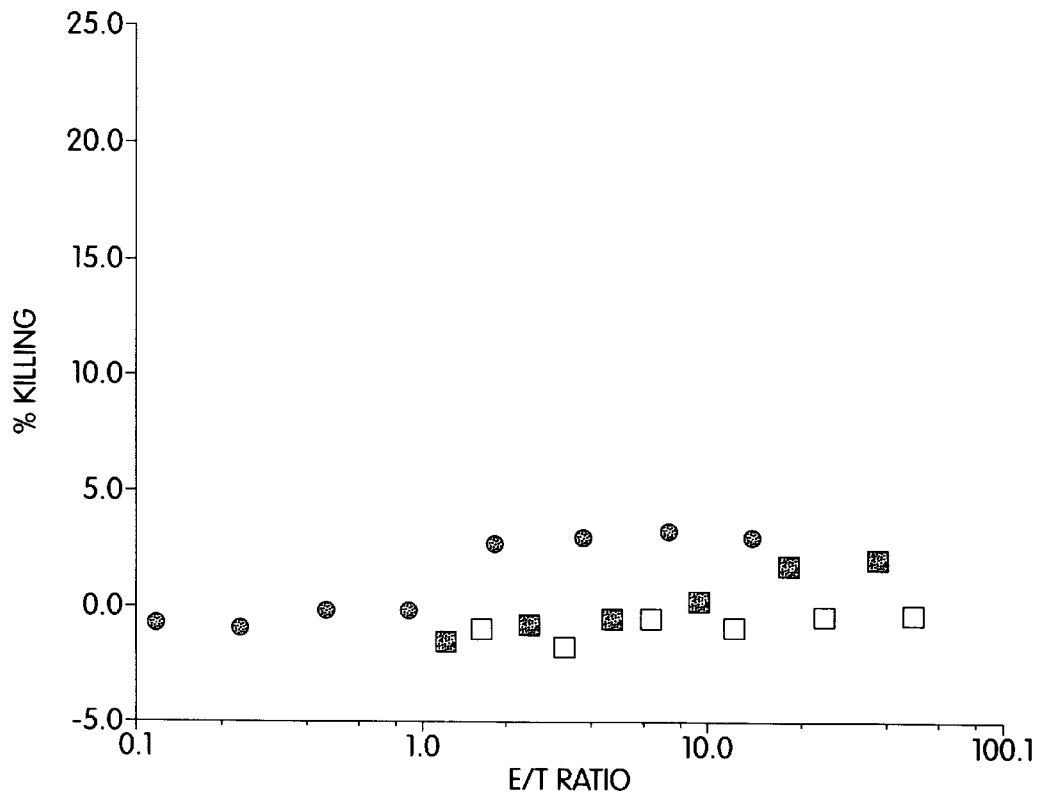
FIGS. 6A–B shows specificity of CD4-directed cytolysis.

To control for the possibility that vaccinia infection might promote artefactual recognition by CTL, similar cytolysis experiments were performed with target cells infected with vaccinia recombinants expressing the phosphatidylinositol linked form of CD16 (CD16$_{PI}$) and labeled with $^{51}$Cr, and with CTL infected with control recombinants expressing either CD16$_{PI}$ or CD16:ζ. FIG. 6A shows that T cells expressing non-CD4 chimeras do not recognize native HeLa cells or HeLa cells expressing gp120/41, and similarly that T cells expressing CD4 chimeras do not recognize HeLa cells expressing other vaccinia-encoded surface proteins. In addition, CTLs expressing non-chimeric CD4 do not significantly lyse HeLa cells expressing gp120/41 (FIG. 6A).

EXAMPLE VII
MHC Class II-Bearing Cells are not Targeted by the Chimeras

Figure 6B:
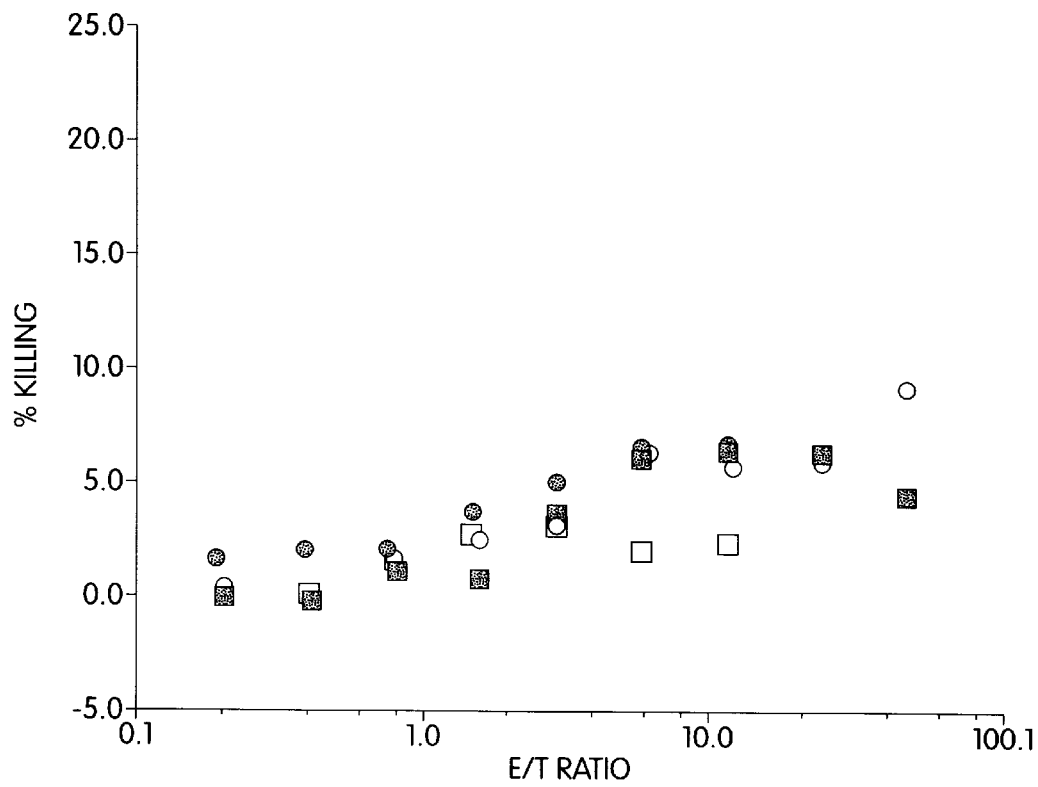

CD4 is thought to interact with a nonpolymorphic sequence expressed by MHC class II antigen (Gay et al., *Nature* 328:626–629 (1987); Sleckman et al., *Nature* 328:351–353 (1987)). Although a specific interaction between CD4 and class II antigen has never been documented with purified proteins, under certain conditions adhesion between cells expressing CD4 and cells expressing class II molecules can be demonstrated (Doyle et al., *Nature* 330:256–259 (1987); Clayton et al., *J. Exp. Med.* 172:1243–1253 (1990); Lamarre et al., *Science* 245:743–746 (1989)). Next examined was whether killing could be detected against cells bearing class II. FIG. 6B shows that there is no specific cytolysis directed by CD4:ζ against the Raji B cell line, which expresses abundant class II antigen. Although a modest (≈5%) cytolysis is observed, a class II-negative mutant of Raji, RJ2.2.5, (Accolla, *J. Exp. Med.* 157:1053–1058 (1983)) shows a similar susceptibility, as do Raji cells incubated with uninfected T cells.

Figure 7A:
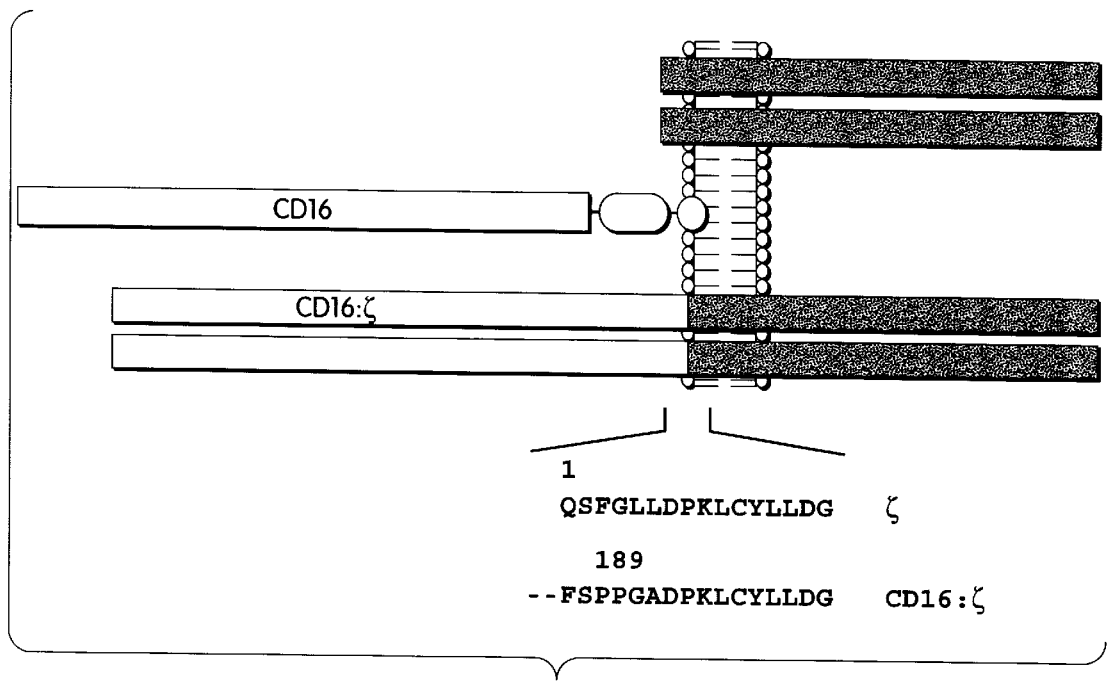
FIGS. 7A–B shows characterization of the CD16:ζ chimeric receptor.

EXAMPLE VIII
Sequence Requirements for Induction of Cytolysis by the T Cell Antigen/Fc Receptor Zeta Chain Although chimeras between CD4 and ζ can arm cytotoxic T lymphocytes (CTL) to kill target cells expressing HIV gp120, an alternative to CD4 was sought in order to unambiguously compare the properties of zeta chimeras introduced into human T cell lines. Such lines can express CD4, making it difficult to specifically define the relationship between the type or degree of calcium mobilization and the cytotoxic potential of the different chimeras. To circumvent this, chimeras were created between ζ and CD16 in which the extracellular domain of CD16 is attached to the transmembrane and intracellular sequences of ζ (FIG. 7A). The gene fusions were introduced into a vaccinia virus expression plasmid bearing the *E. coli* gpt gene as a selectable marker and inserted into the genome of the vaccinia WR strain by homologous recombination and selection for growth in mycophenolic acid (Falkner and Moss, *J. Virol.* 62:1849 (1988); Boyle and Coupar, *Gene* 65:123 (1988)).

Figure 7B:
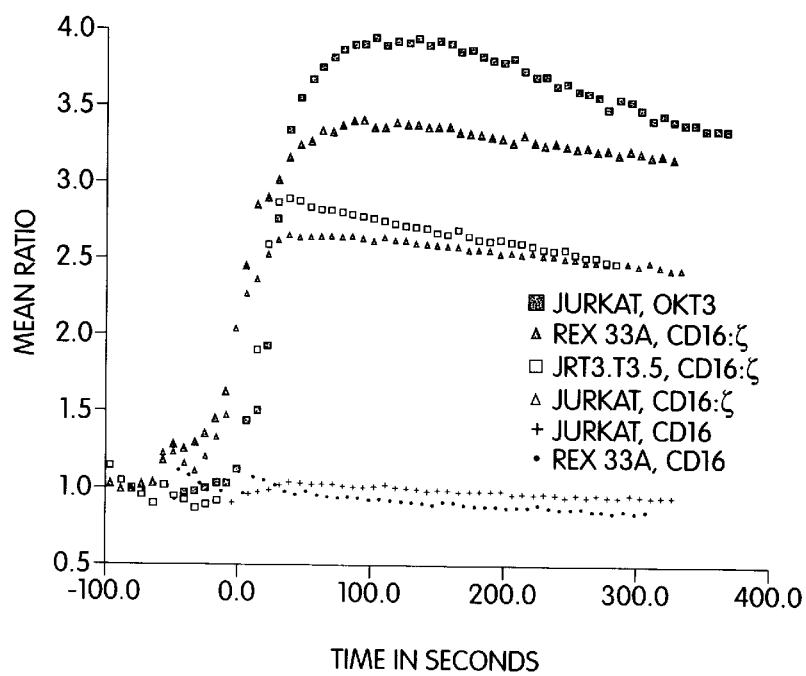

T cell lines were infected with the vaccinia recombinants and the relative cytoplasmic free calcium ion concentration was measured following crosslinking of the extracellular domains with antibodies. Both spectrofluorimetric (bulk population) and flow cytometric (single cell) measurements were performed with cells loaded with the dye Indo-1 (Grynkiewicz et al., *J. Biol. Chem.* 260:3440 (1985); Rabinovitch et al., *J. Immunol.* 137:952 (1986)). FIG. 7B shows an analysis of data collected from cells of the Jurkat human T cell leukemia line infected with vaccinia recombinants expressing CD16:ζ fusion protein. Crosslinking of the chimeras reproducibly increased intracellular calcium, while similar treatment of cells expressing nonchimeric CD16 had little or no effect. When the chimera was expressed in mutant cell lines lacking antigen receptor, either REX33A (Breitmeyer et al., *J. Immunol.* 138:726 (1987); Sancho et al., *J. Biol. Chem* 264:20760 (1989)), or Jurkat mutant JRT3.T3.5 (Weiss et al., *J. Immunol.* 135:123 (1984)); or a strong response to CD16 antibody crosslinking was seen. Similar data have been collected on the REX20A (Breitmeyer et al., supra, 1987; Blumberg et al., *J. Biol. Chem.* 265:14036 (1990)) mutant cell line, and a CD3/Ti negative mutant of the Jurkat cell line established in this laboratory. Infection with recombinants expressing CD16:ζ did not restore the response to anti-CD3 antibody, showing that the fusion protein did not act by rescuing intracellular CD3 complex chains.

Figures 8A, 8B:
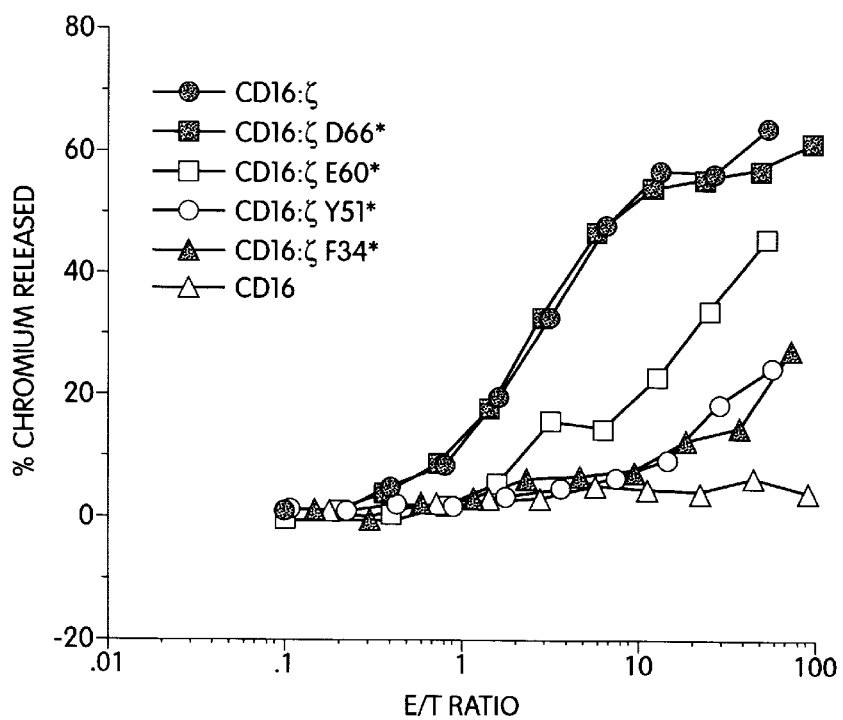
FIGS. 8A–B shows deletion analysis of cytolytic potential.

To evaluate the ability of the chimeras to redirect cell-mediated immunity, CTLs were infected with vaccinia recombinants expressing CD16 chimeras and used to specifically lyse hybridoma cells expressing membrane-bound anti-CD16 antibodies. This assay is an extension of a hybridoma cytotoxicity assay originally developed to analyze effector mechanisms of cells bearing Fc receptors (Graziano and Fanger, *J. Immunol.* 138:945, 1987; Graziano and Fanger, *J. Immunol.* 139:35–36, 1987; Shen et al., *Mol. Immunol.* 26:959, 1989; Fanger et al., *Immunol. Today* 10:92, 1989). FIG. 8B shows that expression of CD16:ζ in cytotoxic T lymphocytes allows the armed CTL to kill 3G8 (anti-CD16; Fleit et al., *Proc. Natl. Acad. Sci. USA* 79:3275, 1982) hybridoma cells, whereas CTL expressing the phosphatidylinositol-linked form of CD16 are inactive. CTL armed with CD16:ζ also do not kill hybridoma cells expressing an irrelevant antibody.

To identify the minimal ζ sequences necessary for cytolysis, a series of deletion mutants were prepared in which successively more of the ζ intracellular domain (SEQ ID NO: 44) was removed from the carboxyl terminus (FIG. 8A). Most of the intracellular domain of zeta could be removed with little consequence for cytolytic potential; the full length chimera CD16:ζ was essentially equal in efficacy to the chimera deleted to residue 65, CD16:ζAsp66* (FIG. 8B). A substantial decrease in cytotoxicity was observed on deletion to ζ residue 59 (chimera CD16:ζGlu60*), and further deletion to residue 50 resulted in slightly less activity. However complete loss of activity was not observed even when the intracellular domain was reduced to a three residue transmembrane anchor (FIG. 8B).

Because ζ is a disulfide linked dimer, one explanation for the retention of cytolytic activity was that endogenous ζ was forming heterodimers with the chimeric ζ deletion, thereby reconstituting activity. To test this idea, ζ residues 11 and 15 were changed from Asp and Cys respectively to Gly (Cys11Gly/Asp15Gly), and immunoprecipitations were carried out as follows. Approximately $2 \times 10^6$ CV1 cells were infected for one hour in serum free DME medium with recombinant vaccinia at a multiplicity of infection (moi) of at least ten. Six to eight hours post-infection, the cells were detached from the plates with PBS/1 mM EDTA and surface labeled with 0.2 mCi $^{125}$I per $2 \times 10^6$ cells using lactoperoxidase and $H_2O_2$ by the method of Clark and Einfeld (*Leukocyte Typing II, pp* 155–167, Springer-Verlag, N.Y., 1986). The labeled cells were collected by centrifugation and lysed in 1% NP-40, 0.1% SDS, 0.15M NaCl, 0.05M Tris, pH 8.0, 5 mM $MgCl_2$, 5 mM KCl, 0.2M iodoacetamide and 1 mM PMSF. Nuclei were removed by centrifugation, and CD16 proteins were immunoprecipitated with antibody 3G8 (Fleit et al., supra, 1982; Medarex) and anti-mouse IgG agarose (Cappel, Durham, N.C.). Samples were electrophoresed through an 8% polyacrylamide/SDS gel under non-reducing conditions or through a 10% gel under reducing conditions. These immunoprecipitations confirmed that the CD16:ζCys11Gly/Asp15Gly chimera did not associate in disulfide-linked dimer structures.

The cytolytic activity of the mutant receptors was also tested. The mutated chimera deleted to residue 65 (CD16:ζCys11Gly/Asp15Gly/Asp66*) was, depending on the conditions of assay, two to eight fold less active in the cytolysis assay than the comparable unmutated chimera (CD16:ζAsp66*), which was usually within a factor of two of, or indistinguishable in activity from, CD16:ζ (FIG. 9B). The reduction in activity of the mutant chimeras is comparable to the reduction seen with CD4 chimeras of similar structure (see above) and is most likely attributable to the lower efficiency of ζ monomers compared to dimers. In contrast, the Asp$^-$, Cys$^-$ mutated chimera deleted to residue 59 had no cytolytic activity (FIG. 9B), supporting the hypothesis that association with other chains mediated by the transmembrane Cys and/or Asp residues was responsible for the weak persistence of cytolytic activity in deletions more amino terminal than residue 65.

Figure 9A:
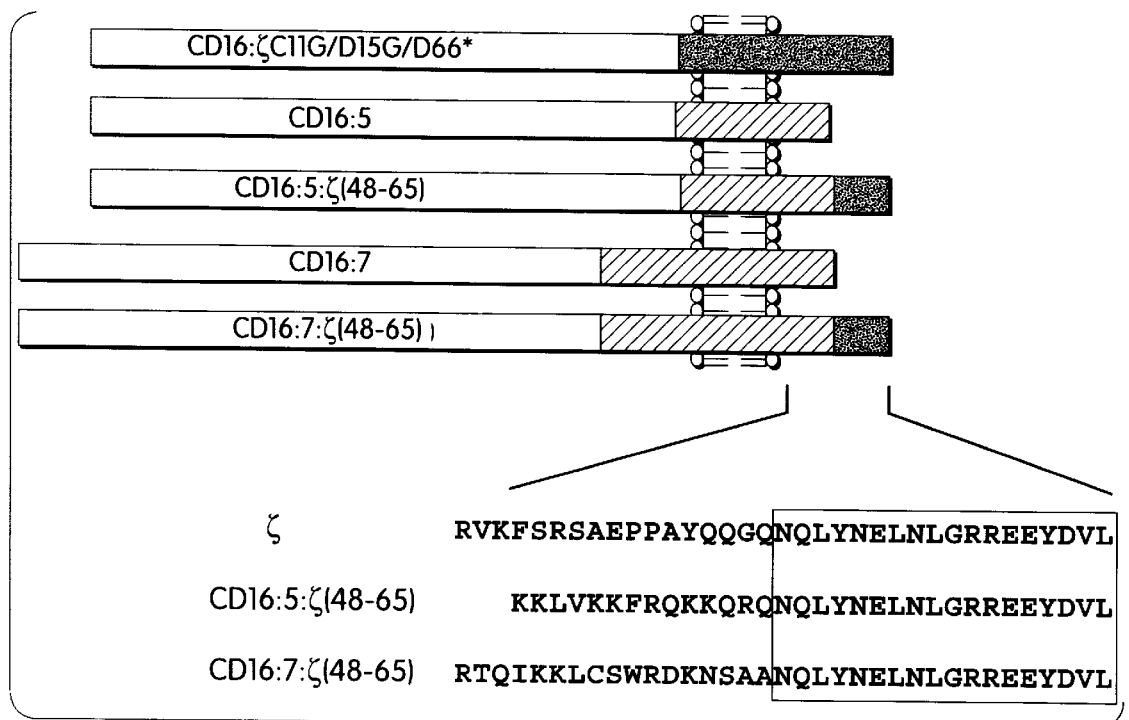
FIGS. 9A–D shows that elimination of the potential for transmembrane interactions reveals a short ζ segment capable of mediating cytolysis.
Figure 9B:
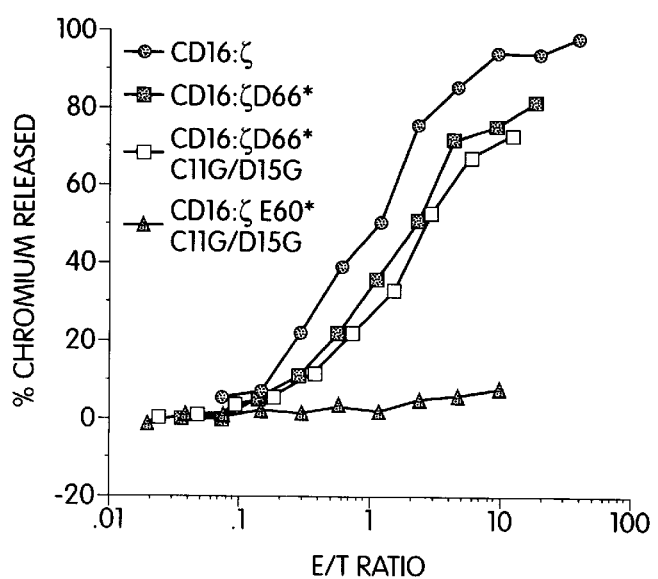
Figure 9C:
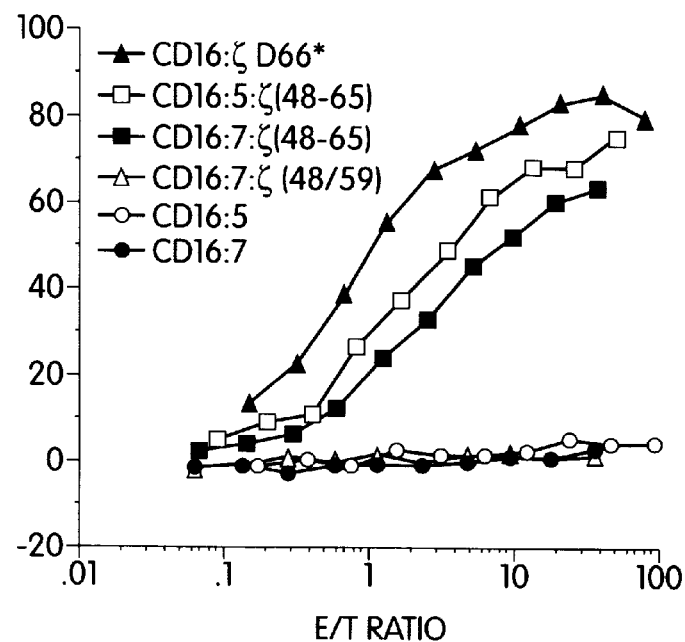
Figure 9D:
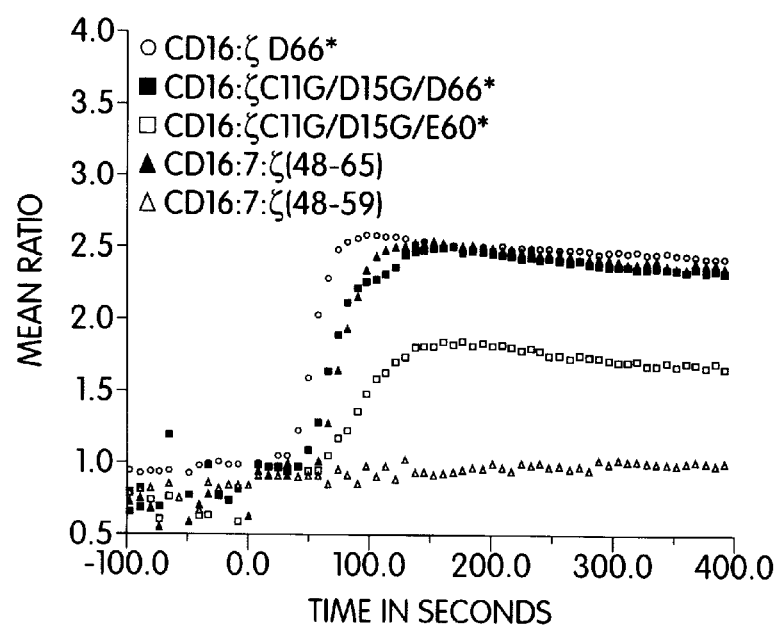
Figure 10A:
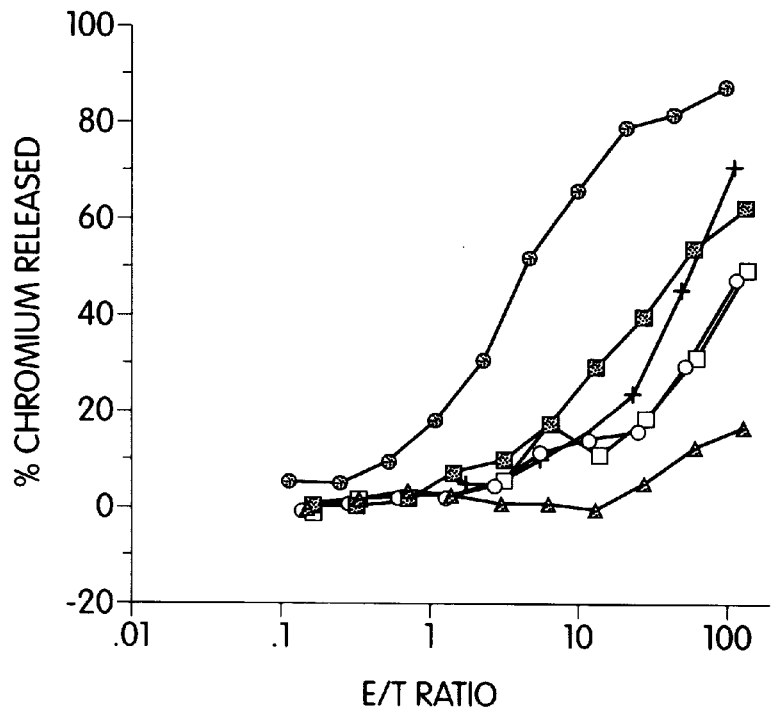
FIGS. 10A–F shows the contribution of individual amino acids to the activity of the 18 residue cytolytic signal-transducing motif.
Figure 10B:
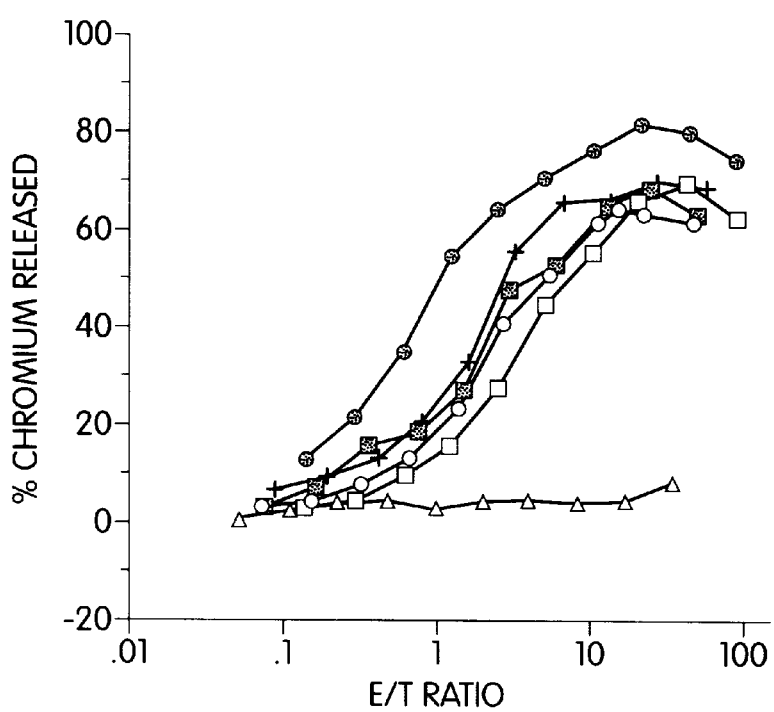
Figure 10C:
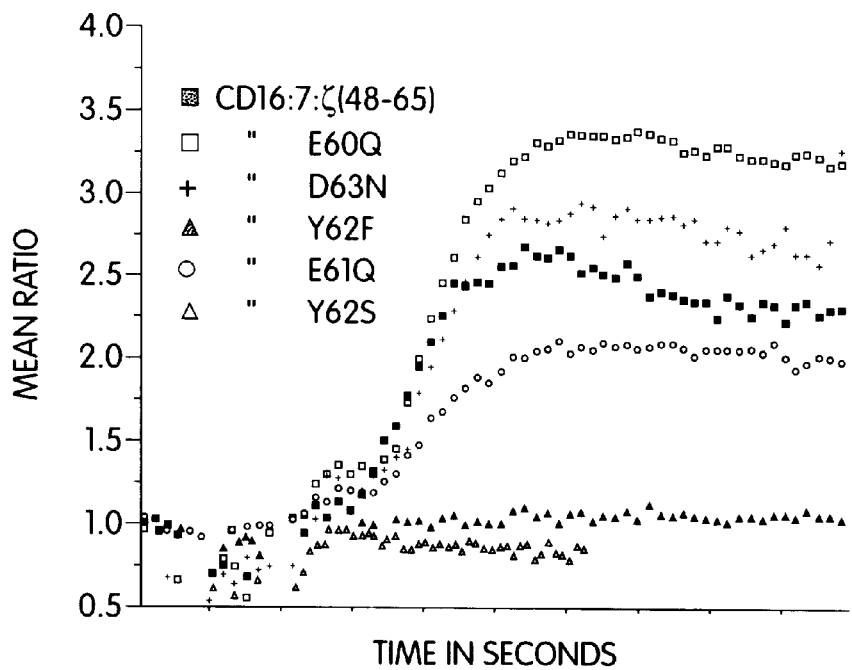
Figure 10D:
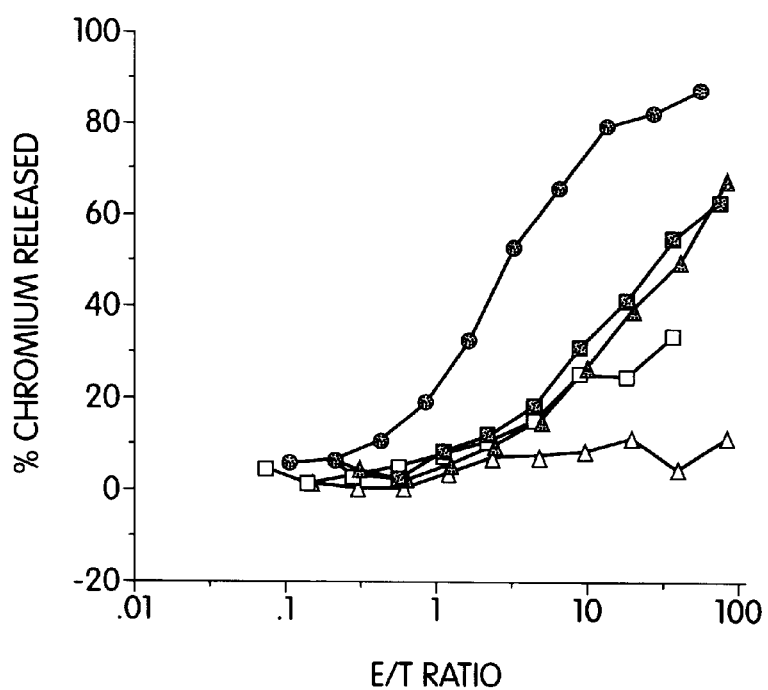
Figure 10E:
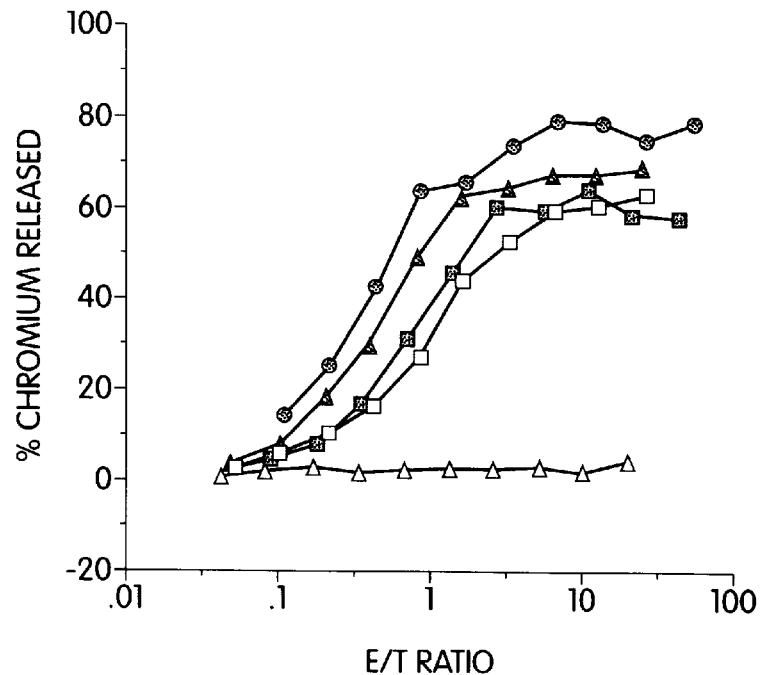
Figure 10F:
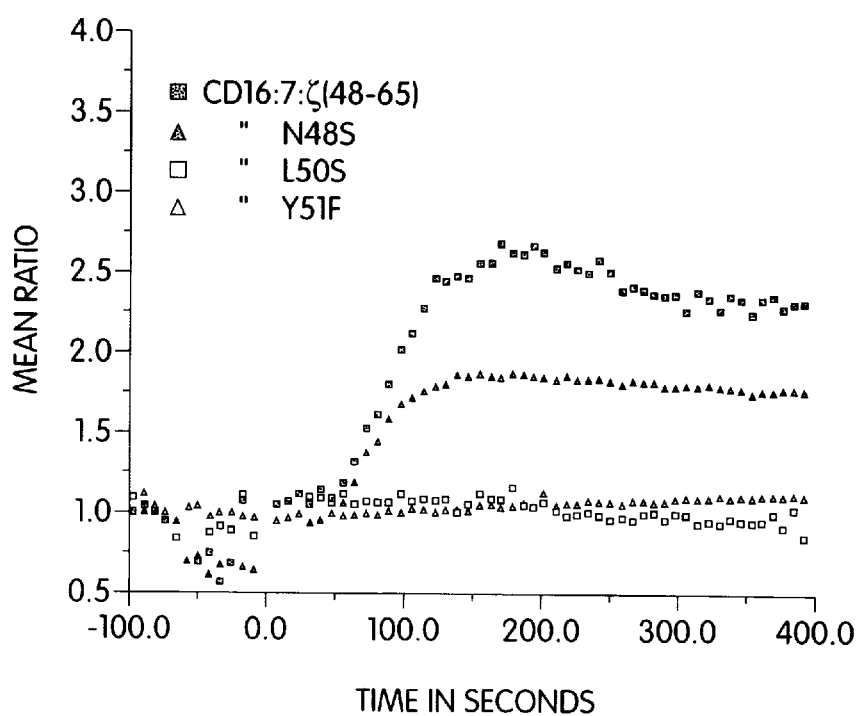

Flow cytometric studies showed that the deletion mutants lacking transmembrane Asp and Cys residues could still promote an increase in free intracellular calcium ion in response to antibody crosslinking in a TCR$^-$ mutant Jurkat cell line (FIG. 9D). Similar results were obtained for chimeras expressed in the parental Jurkat line. In the case of CD16:ζCys11Gly/Asp15Gly/Glu60*, these data demonstrate that the ability to mediate calcium responsiveness can be mutationally separated from the ability to support cytolysis.

To definitively eliminate the possible contribution of ζ transmembrane residues, the transmembrane and first 17 cytoplasmic residues of ζ were replaced by sequences encoding the membrane spanning and first 14 or first 17 cytoplasmic residues of the CD5 or CD7 antigens, respectively (FIG. 9A). The resulting tripartite fusion proteins CD16:5:ζ(48–65) and CD16:7:ζ(48–65) did not form disulfide-linked dimers as do the simpler CD16:ζ chimeras, because they lacked the cysteine residue in the ζ transmembrane domain. Both tripartite chimeras were able to mobilize calcium in Jurkat and TCR negative cell lines (FIG. 9D) and to mount a cytolytic response in CTL (FIG. 9C and data not shown). However truncation of the ζ portion to residue 59 in chimera CD16:7:ζ(48–59) abrogates the ability of tripartite fusion to direct calcium responsiveness in TCR positive or negative Jurkat cells or cytolysis in mature CTL (FIGS. 9C and 9D and data not shown).

To examine the contributions of individual residues within the 18-residue motif, we prepared a number of mutant variants by site-directed mutagenesis, and evaluated their ability to mediate receptor-directed killing under conditions of low (FIGS. 10A and 10D) or high (FIGS. 10B and 10E) expression of chimeric receptor. FIGS. 10A–F shows that while a number of relatively conservative substitutions (i.e., replacing acidic residues with their cognate amides, or tyrosine with phenylalanine) which spanned residues 59 to 63 yielded moderate compromise of cytolytic efficacy, in general the variants retained the ability to mobilize calcium. However collectively these residues comprise an important submotif inasmuch as their deletion eliminates cytolytic activity. Conversion of Tyr 62 to either Phe or Ser eliminated both the cytotoxic and calcium responses. At the amino terminus of the 18 residue segment, replacement of Tyr 51 with Phe abolished both calcium mobilization and cytolytic activity, while substitution of Leu with Ser at position 50 eliminated the calcium response while only partially impairing cytolysis. Without being bound to a particular hypothesis, it is suspected that the inability of the Leu50Ser mutant to mobilize calcium in short term flow cytometric assays does not fully reflect its ability to mediate a substantial increase in free intracellular calcium ion over the longer time span of the cytolysis assay. However, calcium-insensitive cytolytic activity has been reported for some cytolytic T cell lines, and the possibility that a similar phenomenon underlies the results described herein has not been ruled out. Replacement of Asn48 with Ser partially impaired cytotoxicity in some experiments while having little effect in others.

Figure 11A:
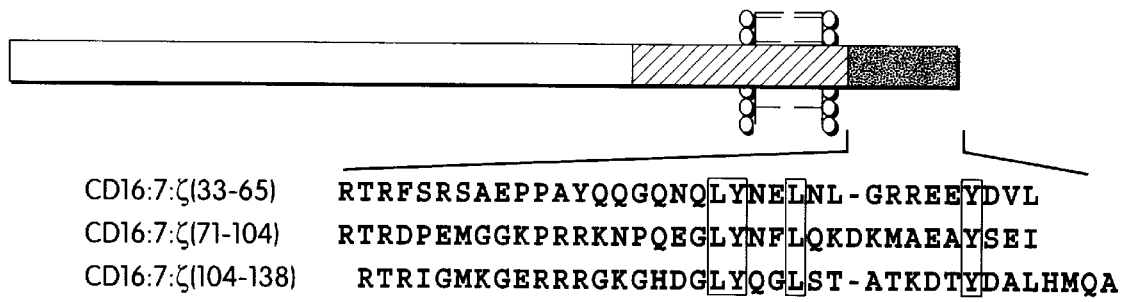
FIGS. 11A–B shows alignment of internal repeats of ζ and comparison of their ability to support cytolysis.
Figure 11B:
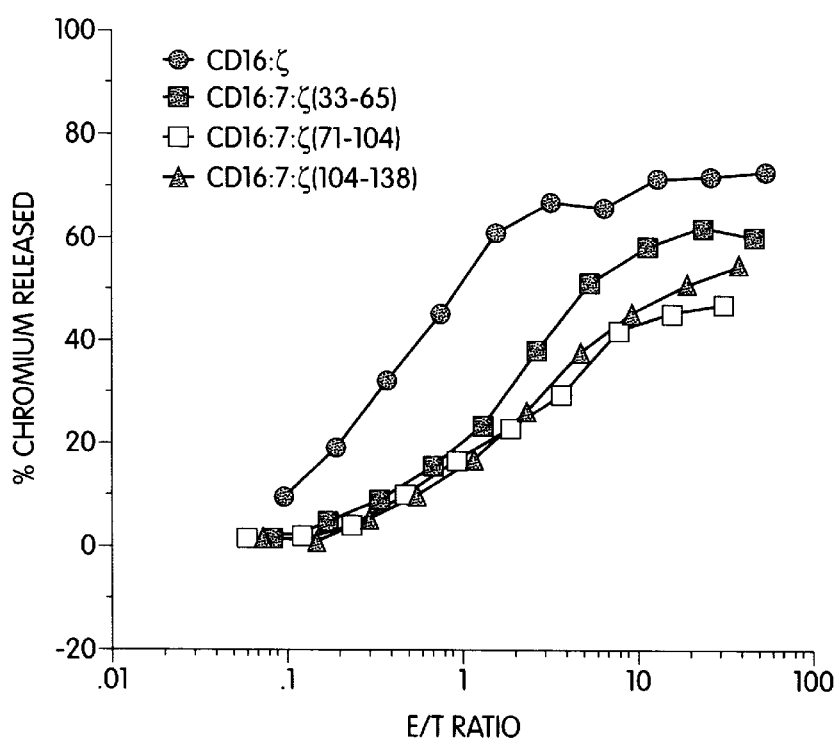

To investigate the potential role of redundant sequence elements, the intracellular domain of ζ was divided into three segments, spanning residues 33 to 65, 71 to 104, and 104 to 138. Each of these segments was attached to a CD16:CD7 chimera by means of a MluI site introduced just distal to the basic membrane anchoring sequences of the intracellular domain of CD7 (see below; FIG. 11A) Comparison of the cytolytic efficacy of the three elements showed they were essentially equipotent (FIG. 11B). Sequence comparison (FIG. 11A) shows that the second motif bears eleven residues between tyrosines, whereas the first and third motifs bear ten.

Although a precise accounting of the process of T cell activation has not been made, it is clear that aggregation of the antigen receptor, or of receptor chimeras which bear ζ intracellular sequences, triggers calcium mobilization, cytokine and granule release, and the appearance of cell surface markers of activation. The active site of ζ, a short linear peptide sequence probably too small to have inherent enzymatic activity, likely interacts with one or at most a few proteins to mediate cellular activation. It is also clear that mobilization of free calcium is not by itself sufficient for cellular activation, as the ability to mediate cytolysis can be mutationally separated from the ability to mediate calcium accumulation.

As shown herein, addition of 18 residues from the intracellular domain of ζ to the transmembrane and intracellular domain of two unrelated proteins allows the resulting chimeras to redirect cytolytic activity against target cells which bind to the extracellular portion of the fusion proteins, although chimeras bearing the 18 residue motif are approximately eight-fold less active than chimeras based on full length ζ, the reduced activity can be attributed to the loss of transmembrane interactions which normally allow wild-type ζ to form disulfide linked dimers. That is, ζ deletion constructs which have the same carboxyl terminus as the motif and lack transmembrane Cys and Asp residues typically show slightly less activity than chimeras bearing only the 18 residue motif.

The cytolytic competency element on which we have focused has two tyrosines and no serines or threonines, restricting the possible contributions of phosphorylation to activity. Mutation of either tyrosine destroys activity, however, and although preliminary experiments do not point to a substantial tyrosine phosphorylation following crosslinking of chimeric surface antigens bearing the 18 reside motif, the possible participation of such phosphorylation at a low level cannot be excluded. In addition to the effects noted at the two tyrosine residues, a number of amino acid replacements at the amino and carboxyl terminus of the motif weaken activity under conditions of low receptor density.

Sequences similar to the ζ active motif can be found in the cytoplasmic domains of several other transmembrane proteins, including the CD3 δ and γ molecules, the surface IgM associated proteins mb1 and B29, and the β and γ chains of the high affinity IgE receptor, FcεRI (Reth, *Nature* 338:383, 1989). Although the function of these sequences is uncertain, if efficiently expressed, each may be capable of autonomous T cell activation, and such activity may explain the residual TCR responsiveness seen in a zeta-negative mutant cell line (Sussman et al., *Cell* 52:85, 1988).

ζ itself bears three such sequences, approximately equally spaced, and a rough trisection of the intracellular domain shows that each is capable of initiating a cytolytic response. η, a splice isoform of ζ (Jin et al., supra, 1990; Clayton et al., *Proc. Natl. Acad. Sci. USA* 88:5202, 1991), lacks the carboxyl half of the third motif. Because removal of the carboxyl half of the first motif abolishes activity, it appears likely that the majority of the biological effectiveness of η can be attributed to the first two motifs. Although by different measures η is equally as active as ζ in promoting antigen-mediated cytokine release (Bauer et al., *Proc. Natl. Acad. Sci. USA* 88:3842, 1991) or redirected cytolysis (see above), n is not phosphorylated in response to receptor stimulation (Bauer et al., supra, 1991). Thus either the presence of all three motifs is required for phosphorylation, or the third motif represents a favored substrate for an unidentified tyrosine kinase.

EXAMPLE IX
Cytolytic signal Transduction by Human Fc Receptor

To evaluate the actions of different human Fc receptor subtypes, chimeric molecules were created in which the extracellular domain of the human CD4, CD5 or CD16 antigens were joined to the transmembrane and intracellular domains of the FcRIIγA, B1, B2, and C subtypes (nomenclature of Ravetch and Kinet, *Ann. Rev. Immunol.* 9:457, 1991). Specifically, cDNA sequences corresponding to the transmembrane and cytoplasmic domains of the previously described FcRIIA, B1, and B2 isoforms were amplified from the preexisting clone PC23 or from a human tonsil cDNA library (constructed by standard techniques) using the following synthetic oligonucleotides primers:

CCC GGA TCC CAG CAT GGG CAG CTC TT (SEQ ID NO: 18; FcRII A forward);

CGC GGG GCG GCC GCT TTA GTT ATT ACT GTT GAC ATG GTC GTT (SEQ ID NO: 19; FcRII A reverse);

GCG GGG GGA TCC CAC TGT CCA AGC TCC CAG CTC TTC ACC G (SEQ ID NO: 20; FcRII B1 and FcRII B2 forward); and GCG GGG GCG GCC GCC TAA ATA CGG TTC TGG TC (SEQ ID NO: 21; FcRII B1 and FcRII B2 reverse).

These primers contained cleavage sites for the enzymes BamHI and NotI, respectively, indented 6 residues from the 5' end. The NotI site was immediately followed by an antisense stop codon, either CTA or TTA. All primers contained 18 or more residues complementary to the 5' and 3' ends of the desired fragments. The cDNA fragment corresponding to the FcRIIγC cytoplasmic domain, which differs from the IIA isoform in only one amino acid residue (L for P at residue 268) was generated by site directed mutagenesis by overlap PCR using primers of sequence:

TCA GAA AGA GAC AAC CTG AAG AAA CCA ACA A (SEQ ID NO:22) and

TTG TTG GTT TCT TCA GGT TGT GTC TTT CTG A (SEQ ID NO: 23).

Figure 12:
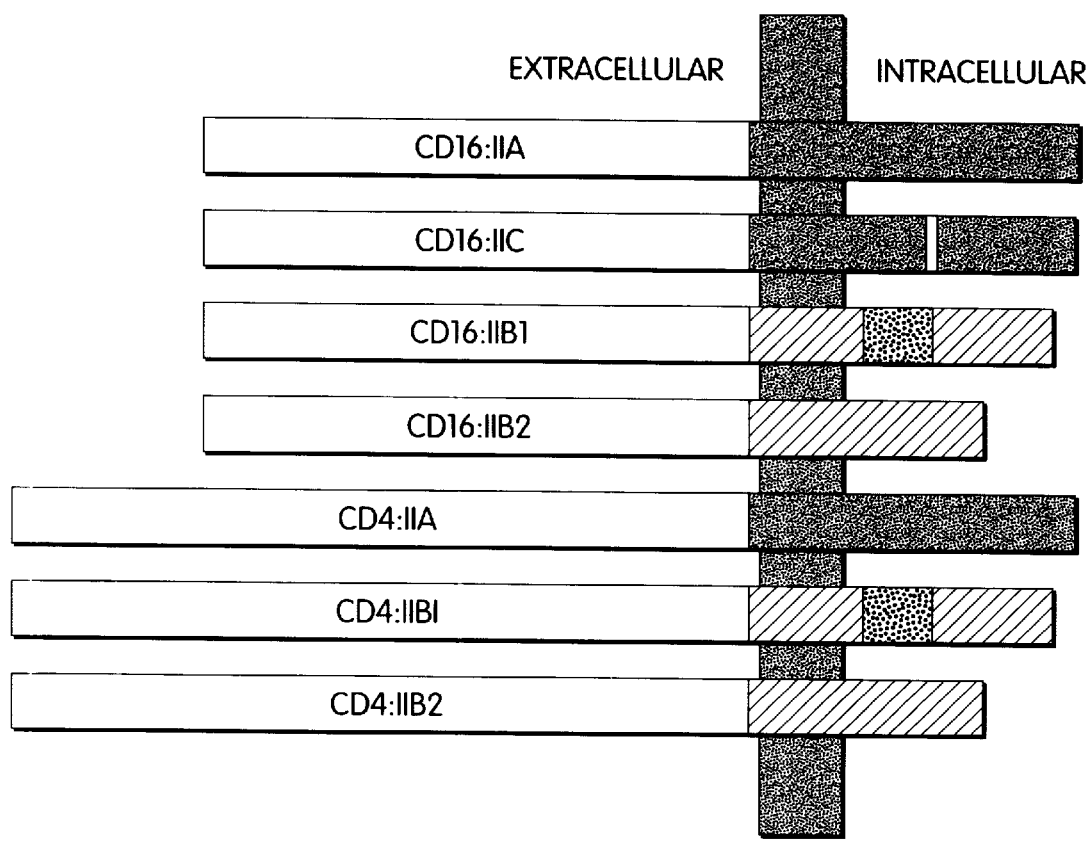
FIG. 12 is a schematic diagram of the CD16:FcRγII chimeras.

The PCR fragments were inserted into vaccinia virus expression vectors which contained the CD16 or CD4 extracellular domains respectively and subsequently inserted into wild type vaccinia by recombination at the thymidine kinase locus, using selection for cointegration of *E. coli* gpt to facilitate identification of the desired recombinants. The identities of all isoforms (shown in FIG. 12) were confirmed by dideoxy sequencing.

Production of the chimeric receptor proteins was further confirmed by immunoprecipitation studies. Approximately $10^7$ JRT3.T3.5 cells were infected for one hour in serum free IMDM medium with recombinant vaccinia at a multiplicity of infection of at least ten. Twelve hours post-infection, the cells were harvested and surface labeled with 0.5 mCi $^{125}$I per $10^7$ cells using the lactoperoxidase/glucose oxidase method (Clark and Einfeld, supra). The labeled cells were collected by centrifugation and lysed 1% NP-40, 0.1 mM $MgCl_2$, 5 mM KCl, 0.2M iodoacetamide and 1 mM PMSF. Nuclei were removed by centrifugation, and CD16 fusion proteins immunoprecipitated with antibody 4G8 and anti-mouse IgG agarose. Samples were electrophoresed under reducing conditions. All immunoprecipitated chimeric receptor molecules were of the expected molecular masses.

Figure 13A:
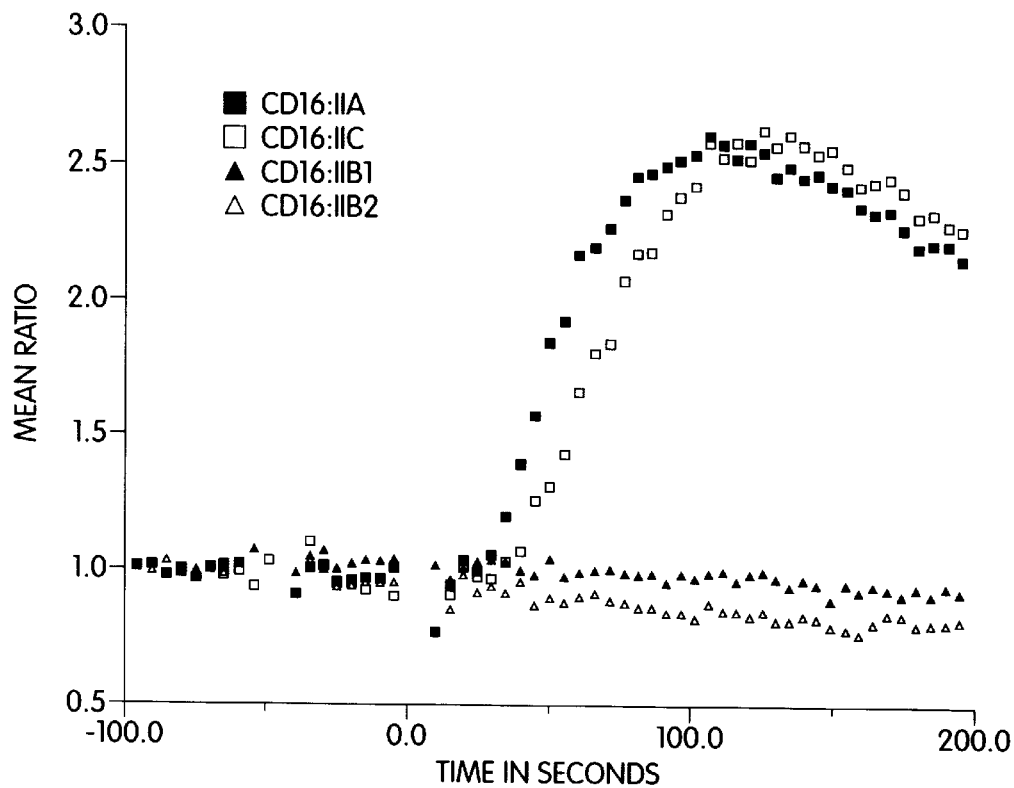
FIGS. 13A–B shows calcium mobilization following crosslinking of CD4:FcRγII and CD16:FcRγII chimeras.
Figure 13B:
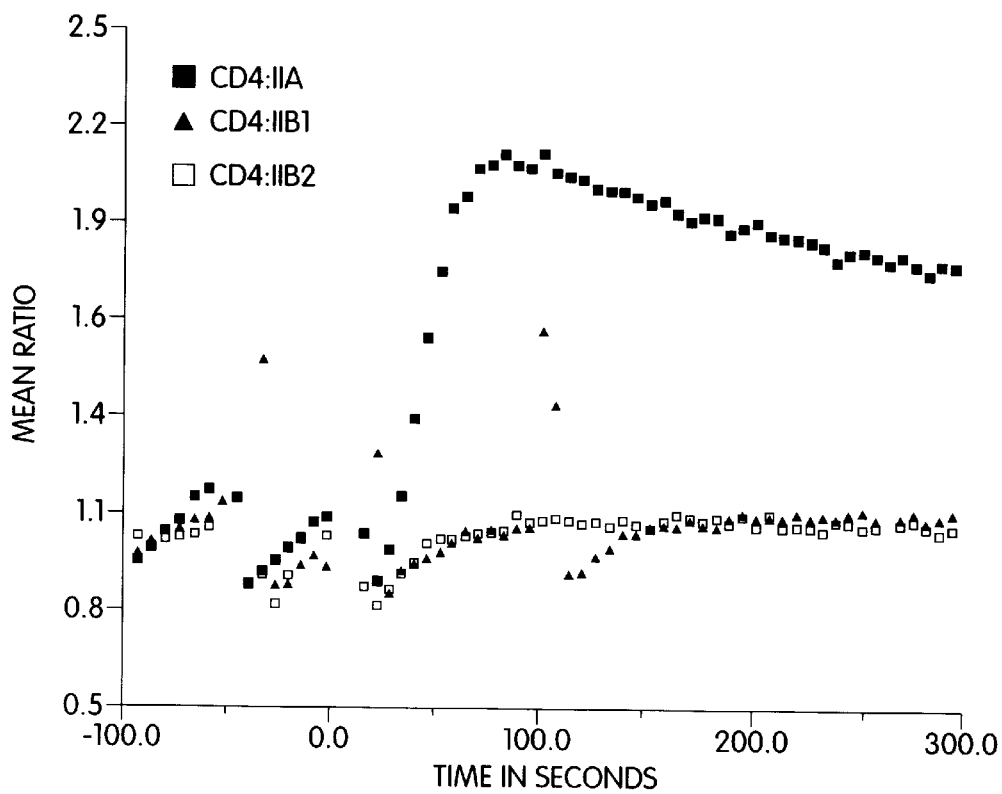

To test the ability of the chimeric receptors to mediate an increase in cytoplasmic free calcium ion, the recombinant viruses were used to infect the TCR⁻ mutant Jurkat cell line JRT3.T3.5 (as described herein) and cytoplasmic free calcium was measured in the cells (as described herein) following crosslinking of the receptor extracellular domains with monoclonal antibody 3G8 or Leu-3A (as described herein). These experiments revealed that the intracellular domains of FcRγII A and C were capable of mediating an increase in cytoplasmic free calcium ion after crosslinking of the extracellular domains, whereas the intracellular domains of FcRγII B1 and B2 were inactive under comparable conditions (FIGS. 13A and 13B). The CD4, CD5 and CD16 hybrids of FcRγII A shared essentially equal capacity to promote the calcium response (FIGS. 13A–B). Other cell lines, from both monocytic and lymphocytic lineages, were capable of responding to the signal initiated by crosslinking of the extracellular domains.

Figure 14A:
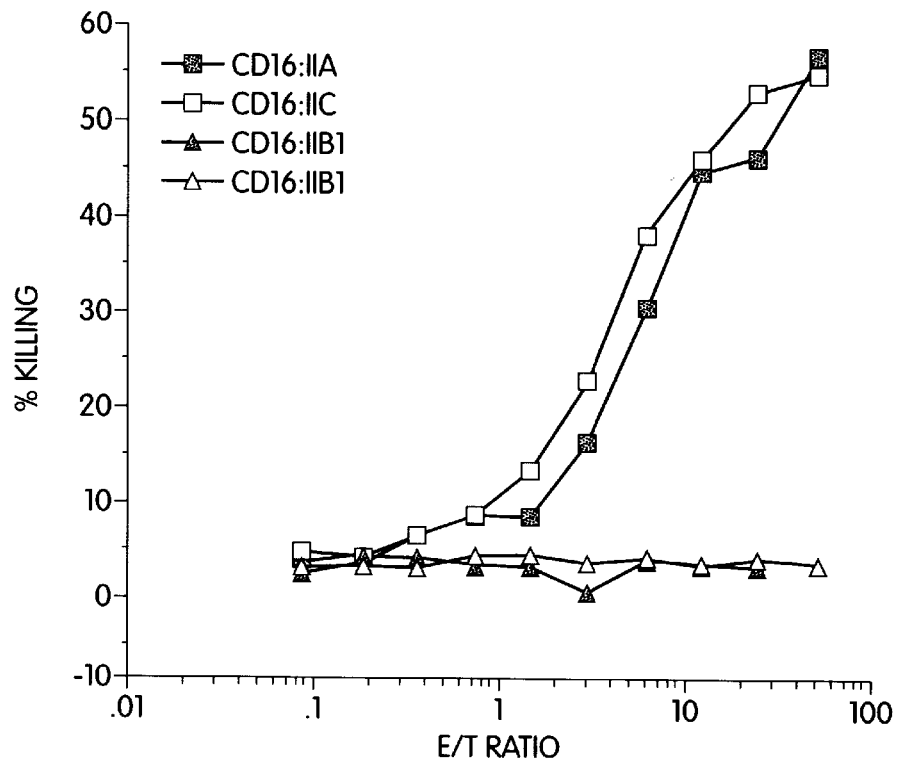
FIGS. 14A–B shows cytolysis assays of CD4:FcRγII and CD16:FcRγII chimeras.

To explore the involvement of the different FcRγII intracellular domains in cytolysis, human cytotoxic T lymphocytes (CTL) were infected with vaccinia recombinants expressing CD16:FcRγII A, B1, B2 and C chimeras. The infected cells were then cocultured with $^{51}$Cr-loaded hybridoma cells (i.e., 3G8 10-2 cells) which expressed cell surface antibody to CD16. In this assay CTLs bearing the CD16 chimera killer the hybridoma target cells (allowing release of free $^{51}$Cr) if the CD16 extracellular domain of the chimera has been joined to an intracellular segment capable of activating the lymphocyte effector program; this cytolysis assay is described in detail below. FIG. 14A shows that CTL armed with CD16:FcRγIIA and C, but not FcRγII B1 or B2, are capable of lysing target cells expressing cell surface anti-CD16 antibody.

Figure 14B:
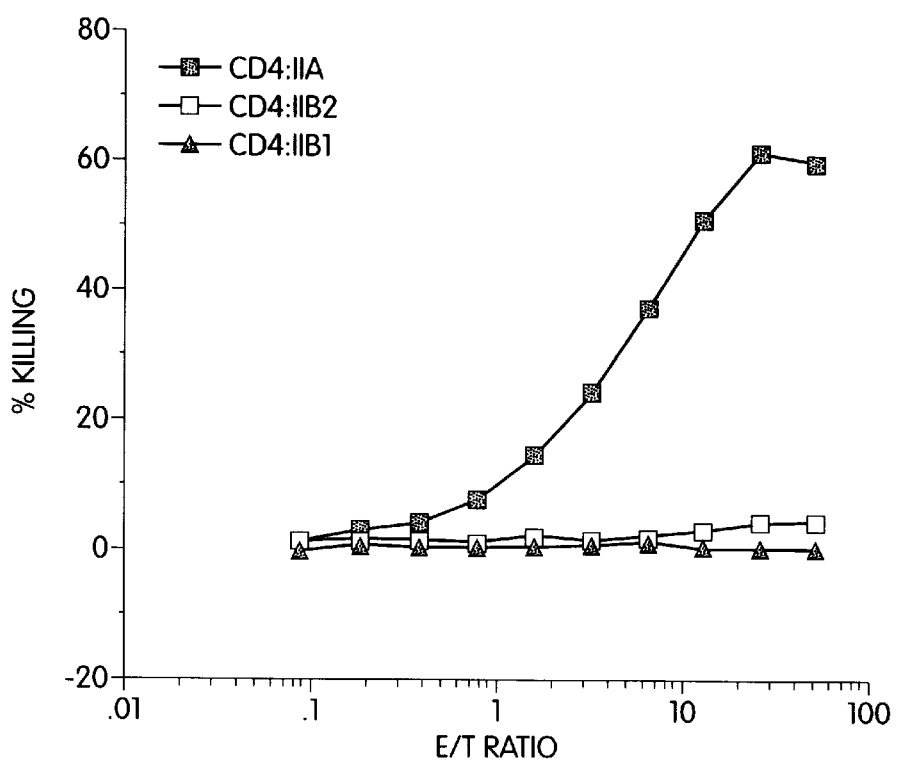

To eliminate the possibility that the specific cytolysis was in some way attributable to interaction with the CD16 moiety, cytolysis experiments were conducted in which the FcRII intracellular domains were attached to a CD4 extracellular domain. In this case the target cells were HeLa cells expressing HIV envelope gp120/41 proteins (specifically, HeLa cells infected with the vaccinia vector vPE16 (available from the National Institute of Allergy and Infections Disease AIDS Depository, Bethesda, Md.). As in the CD16 system, target cells expressing HIV envelope were susceptible to lysis by T cells expressing the CD4:FcRγII A chimera, but not FcRγII B1 or B2 (FIG. 14B).

Figure 15A:
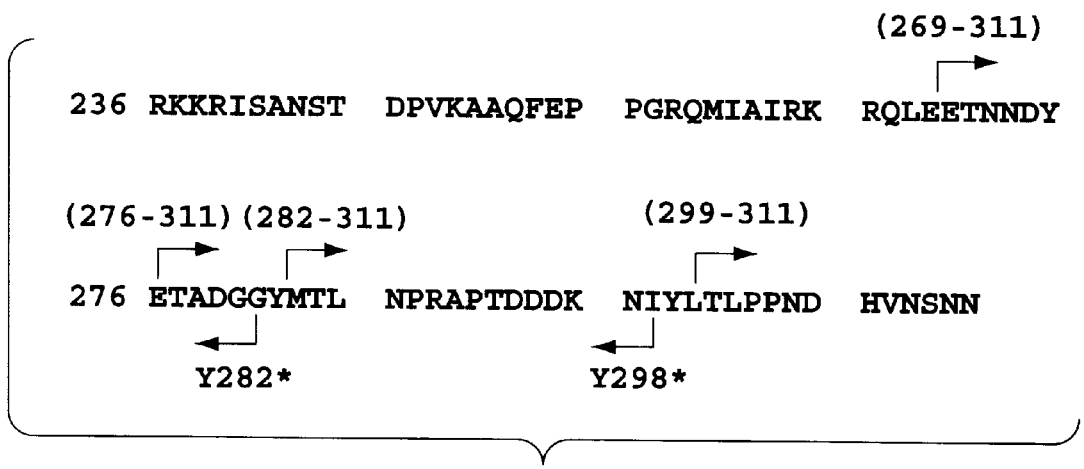
FIGS. 15A–E shows identification of residues in the FcRγII A tail (SEQ ID NO: 53)which are important for cytolysis.

The intracellular domains of FcRγII A and C share no appreciable sequence homology with any other protein, including the members of the extended FcRγ/TCRζ family. To define the sequence elements responsible for induction of cytolysis, 5' and 3' deletions of the intracellular domain coding sequences (described below and shown in FIG. 15A) were prepared and were evaluated for efficacy in calcium mobilization and cytolysis assays (as described herein). In the experiments in which the amino terminal portion of the intracellular domain was removed, the transmembrane domain of FcRγII was replaced with the transmembrane domain of the unrelated CD7 antigen to eliminate the possible contribution of interactions mediated by the membrane-spanning domain.

Figure 15B:
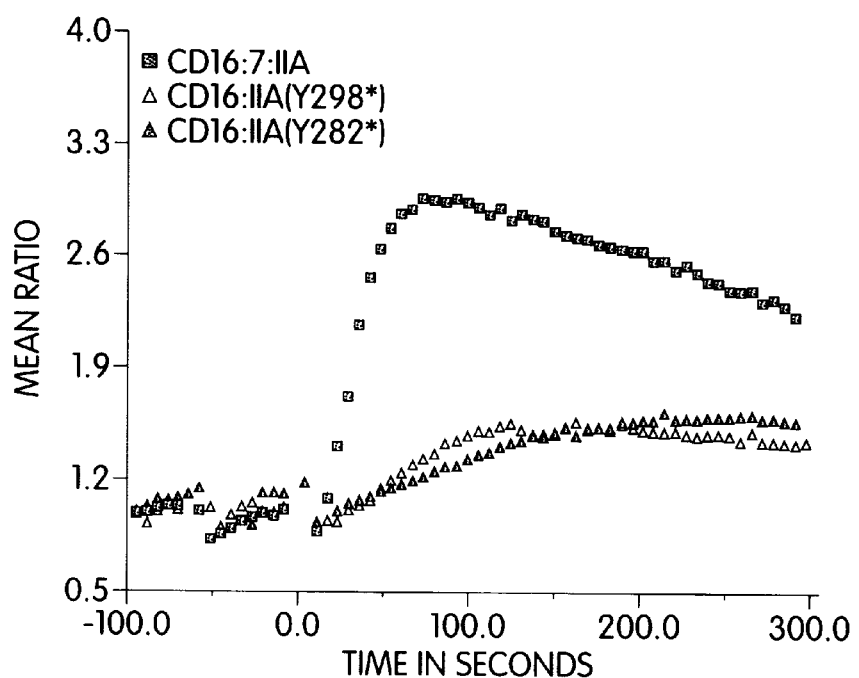
Figure 15C:
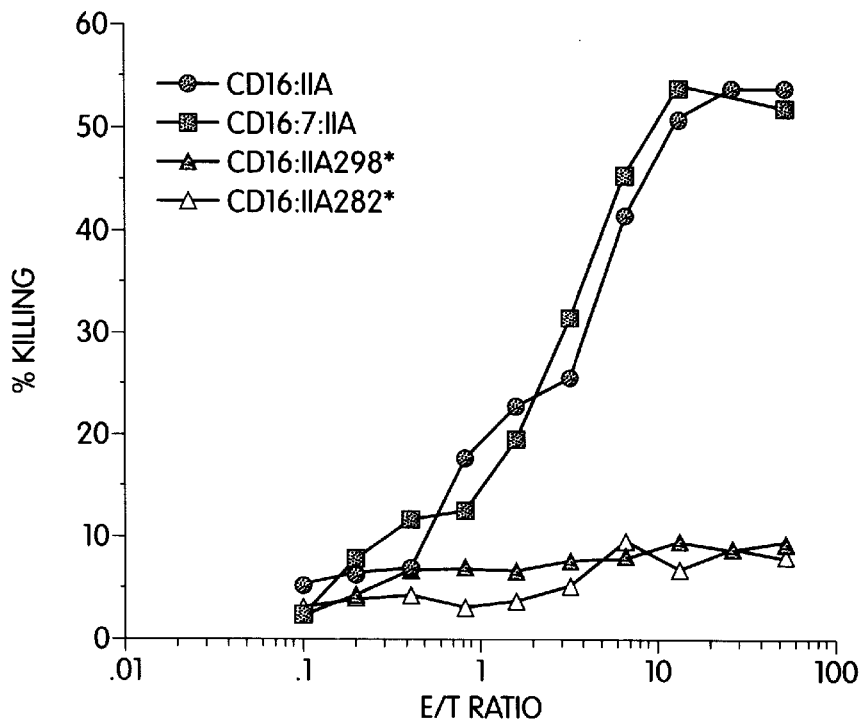
Figure 15D:
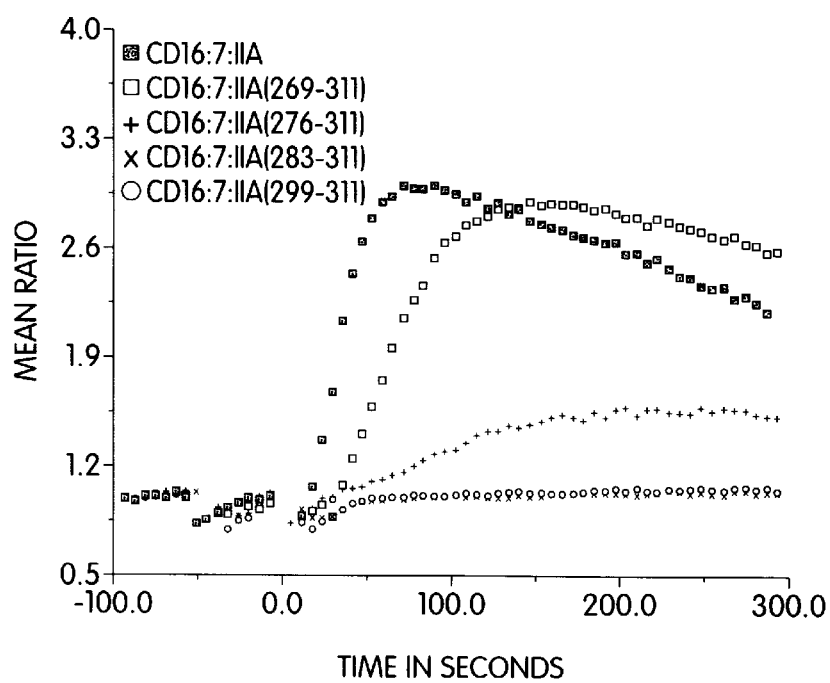
Figure 15E:
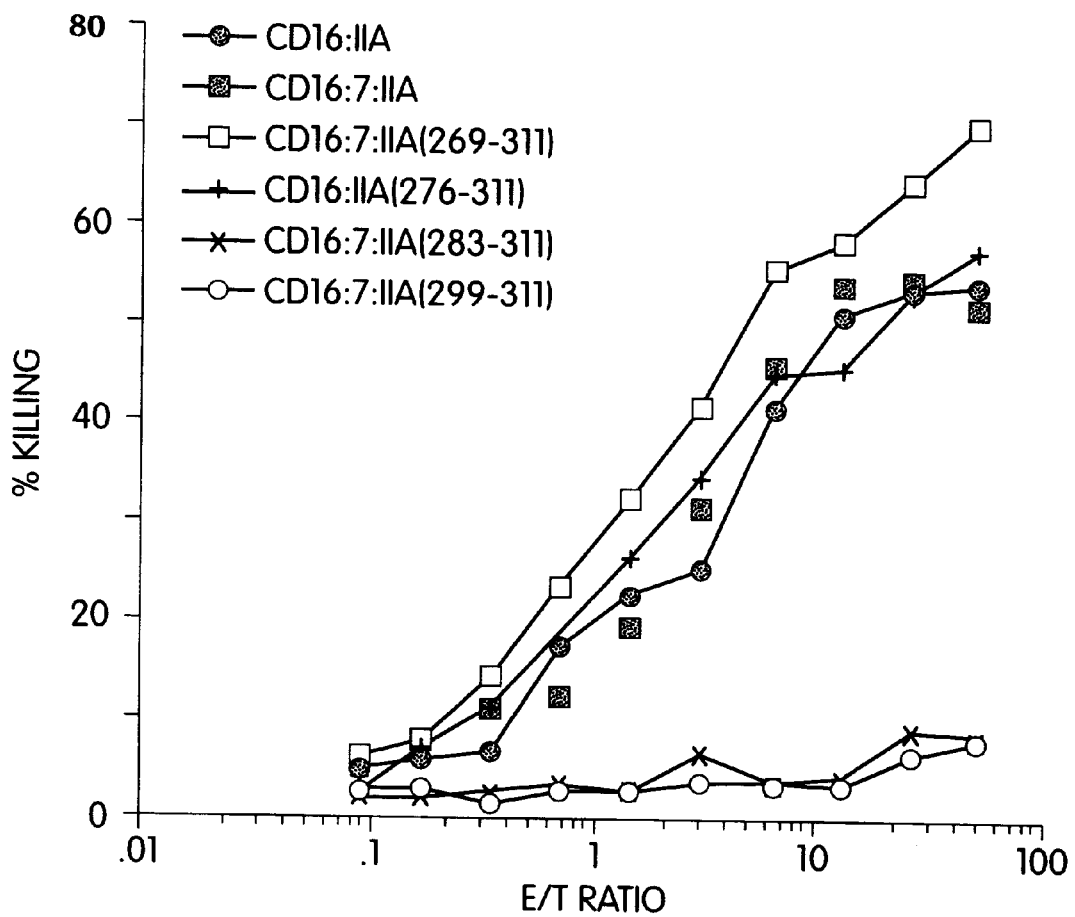

FIGS. 15B and 15C show that removal of the 14 carboxyl-terminal residues, including tyrosine 298, resulted in a complete loss of cytolytic capacity and a substantial reduction in calcium mobilization potential. Further deletion to just before tyrosine 282 gave an identical phenotype (FIGS. 15B and 15C). Deletion from the N-terminus of the intracellular domain to residue 268 had no substantial effect on either calcium profile or cytolytic potency, whereas deletion to residue 275 markedly impaired free calcium release but had little effect on cytolysis (FIGS. 15D and 15E). Further deletion, to residue 282, gave FcRγII tails which lacked the ability to either mobilize calcium or trigger cytolysis (FIGS. 15D and 15E). The 'active element' defined by these crude measures is relatively large (36 amino acids) and contains two tyrosines separated by 16 residues.

EXAMPLE X
Targeted Cytolysis by Lymphocytes Bearing Chimeric CD4 Receptors Which do not Support Infection As discussed above, effector molecules may be engineered which redirect the cytolytic activity of CTLs in an MHC-independent manner. For example, a chimera composed of the extracellular domain of CD4 fused to the ζ chain in a human CTL clone, WH3, specifically kills target cells displaying the surface envelope glycoprotein of HIV-1, gp120. Since the extracellular domain of the CD4 molecule confers susceptibility to HIV infection, however, the armed CTLs may become targets for the virus, resulting in a decrease in their potency (Dalgleish et al., Nature 312:767 (1984); Klatzmann et al., Nature 312:767 (1984)). To prevent such an outcome, chimeric effector molecules were designed based on CD4 which are effective in specifically targeting HIV-infected cells for cell-mediated killing but which do not confer susceptibility to infection by HIV.

A tripartite fusion protein was created by genetic apposition of the extracellular domain of CD4 (FIG. 23) to the hinge, second, and third constant domains of human IgG1 heavy chain (Zettlmeissl et al. *DNA Cell Biol.* 9:347 (1990)) (FIG. 25), which were joined in this case to a portion of the first transmembrane exon of human membrane-bound IgG1, followed by a portion of the human CD7 antigen consisting of the sequences between the sole Ig-like domain and the stop transfer sequence following the transmembrane domain (Aruffo and Seed, *EMBO J.* 6:3313 (1987)) (FIG. 26). The primary amino acid sequence of the extracellular moiety of the CD7 segment consisted of a proline-rich region suggestive of a stalk-like structure which projects the Ig-like domain away from the cell surface (Aruffo and Seed *EMBO J.* 6:3313 (1987)) (FIG. 26). Recombinant vaccinia viruses were prepared to express this and related chimeras as described herein. In particular, recombinant vaccinia viruses were generated by homologous recombination in CV-1 cells. At least two rounds of plaque visualization with OKT4 or Leu3a followed by plaque purification was performed for each stock prior to preparation of high titer stocks in CV-1 cells.

The tripartite chimera (CD4(D1–D4):Ig:CD7) (FIG. 20, molecule "A") showed efficient cell surface expression and was tested for the ability to act as an HIV receptor in a vaccinia-based syncytia formation assay (Lifson et al., *Nature* 323:725 (1986)); Ashorn et al., *J. Virol.* 64:2149 (1990)). HeLa cells infected with a recombinant vaccinia virus (vPE16) encoding the envelope glycoprotein of HIV-1 (Earl et al., *J. Virol.* 64:2448 (1990)) were co-cultured with HeLa cells infected either with CD4, CD4:ζ, or CD4 (D1–D4):Ig:CD7. Six cm dishes of HeLa cells (ATCC, Rockville, Md.) at 50% confluence were infected in serum-free medium for 1 hour at an approximate multiplicity of infection (MOI) of 10. The cells were incubated for an additional 5–6 hours in complete medium and then detached with phosphate buffered saline (PBS) containing 1 mM EDTA. Cells expressing envelope and CD4 chimera were mixed at a 1:1 ratio, and replated in 6 cm dishes with complete medium. Syncytia were scored at 6–8 hours post-cocultivation and photographed.

Co-cultures of CD4 and vPE16 led to formation of readily detectable multinucleated giant cells. Also, a chimera consisting of the extracellular domain of CD4 fused to the ζ chain of the TCR (FIG. 27) (CD4:ζ) was able to mediate syncytia formation, whereas cells expressing CD4(D1–D4):Ig:CD7 gave no sign of cell fusion. We also tested a construct expressing only the first and second domains of CD4 (FIG. 24), CD4(D1,D2):Ig:CD7 (FIG. 20, molecule "B"), since in another context the amino terminal two domains of the CD4 have been shown to be necessary for infectivity by HIV (Landau et al., *Nature* 334:159 (1988)). This molecule proved insusceptible to HIV-induced syncytia formation as well. Binding studies with soluble $^{125}$I-labelled gp120 established that both CD4(D1–D4):Ig:CD7 and CD4 (D1,D2):Ig:CD7 had uncompromised affinity for gp120.

We next determined whether chimeric molecules which resisted syncytium formation would be able to redirect cell killing if endowed with a trigger moiety as described herein. We fused the intracellular domain of ζ (FIG. 27) to the 3' end of CD4(D1–D4):Ig:CD7 and CD4(D1,D2):Ig:CD7 and prepared the corresponding recombinant vaccinia viruses. These constructs, CD4(D1–D4):Ig:CD7:ζ and CD4(D1, D2):Ig:CD7:ζ (FIG. 20, molecules "C" and "D"), were expressed in the human CTL clone WH3 and tested for their ability to target and kill HeLa cells expressing the surface envelope glycoprotein of HIV (using the methods described herein). FIG. 21 shows that the intracellular domain of ζ fused to either CD4(D1–D4):Ig:CD7 or CD4(D1,D2):Ig:CD7 can confer killing ability; constructs lacking the ζ chain were not able to mediate this activity. CD4:ζ, a positive control, mediated a slightly more effective cytotoxicity, and CD4(D1,D2):Ig:CD7:ζ a somewhat less effective cytotoxicity than CD4(D1–D4):Ig:CD7:ζ (FIG. 21). However, it is clear that both CD4(D1–D4):Ig:CD7:ζ and CD4(D1,D2):Ig:CD7:ζ chimeras have the capacity to mediate specific killing of cells expressing HIV envelope proteins on their surface. The tetrapartite chimeras were consistently incapable of mediating syncytium formation in the vaccinia-based assay. We have also demonstrated that a single ζ motif of the sort shown in FIG. 11A is sufficient to confer cytolytic activity to a CD4(D1–D4) chimera.

Radioimmunoprecipitation experiments established that the fusion molecules were predominantly if not entirely dimers. In these experiments, protein-A agarose beads were used to immunoprecipitate the solubilized extract of metabolically labelled HeLa cells infected with recombinant vaccinia expressing CD4(D1–D4):Ig:CD7:ζ and CD4(D1,D2):Ig:CD7:ζ chimeras. The immunoprecipitated material was fractionated by polyacrylamide gel electrophoresis under reducing and nonreducing conditions. In particular, approximately 5×10$^6$ HeLa-S3 cells were infected as described above for vPE16 with the appropriate vaccinia virus stock. Cells were metabolically labelled with 200 μCi/ml of Tran$^{35}$S-Label (ICN Radiochemicals, Irvine, Calif.) for 6–8 hours in cysteine and methionine-deficient medium and detached with PBS containing 1 mM EDTA. Cells were subsequently pelleted and lysed in 150 mM NaCl, 50 mM Tris pH 7.5, 5 mM EDTA, 0.5% NP-40, 0.1% SDS, 5 mM EDTA, 1 mM PMSF. Following the removal of the nuclei by centrifugation, one fifth of each cell extract was adsorbed onto washed protein A-conjugated agarose beads for 2 hours at 4° C. The beads were subsequently washed with PBS containing 1% NP-40 and eluted in sample buffer containing SDS in the presence or absence of mercaptoethanol. The results of these experiments demonstrated that the majority of the immunoprecipitated CD4 (D1–D4):Ig:CD7:ζ and CD4(D1,D2):Ig:CD7:ζ chimeras migrated as dimers of the expected molecular mass under nonreducing conditions.

To directly evaluate the ability of cells expressing the CD4 fusion molecules to support HIV infection, we performed long term infectivity studies on transfectants expressing CD4(D1–D4):Ig:CD7 and CD4(D1,D2):Ig:CD7. Stable transfectants of CD4(D1–D4):Ig:CD7 and CD4(D1,D2):Ig:CD7 and CD4 were prepared in a subline of 293 cells, a readily transfectable cell line of human embryonic kidney origin. The chimeric molecules were subcloned in bidirectional vectors in which the hygromycin B gene was driven by the herpes simplex virus thymidine kinase promoter. A 60–70% confluent 10 cm dish of cells was transfected with 10 μg of this plasmid DNA by calcium phosphate coprecipitation. Prior to transfection, the plasmids were linearized at the unique Sfi I site, and the ends made flush with T4 DNA polymerase. At 24 hours post-transfection, the cells were split fourfold and at 48 hours post-transfection the cells were put under selection with hygromycin B (Sigma, St. Louis, Mo.) at 400 μg/ml. Every 3–4 days, cells were supplied with fresh medium containing hygromycin.

Resistant colonies were picked, expanded, and their expression assessed by indirect immunofluorescence using fluorescein-conjugated anti-human IgG Fc (Organon Teknika, West Chester, Pa.) or Q4120, an antibody reactive with human CD4 (Sigma) followed by flow cytometry (Coulter, Hialeah, Fla.). Two independent clones from each construct with levels of cell surface CD4 comparable to that shown by the other cell lines were selected for analysis. FIG. 22 shows that, following exposure to HIV, p24 was detected in the CD4 stable transfectant cultures as early as 3 days post-infection. The presence of multinucleated giant cells and characteristic ballooning was evident as early as 5 days post-infection in these cultures. No significant p24 levels or evidence of multinucleated giant cells was detectable in the untransfected parental cell line or in either of two independently derived isolates of CD4(D1–D4):Ig:CD7 and CD4 (D1,D2):Ig:CD7 transfectants after 32 days in culture (FIG. 22).

Upon completion of the infectivity studies, cells were analyzed for cell surface CD4 expression. CD4 surface epitope density was significantly reduced in infected cultures expressing CD4, consistent with viral down-modulation, but was unaffected in cultures expressing CD4 (D1–D4):Ig:CD7 and CD4(D1,D2):Ig:CD7. These experiments establish that it is possible to create chimeric molecules bearing the apical two domains of CD4 which, when fused to T cell receptor ζ chain, have the capacity to target and kill HIV-infected cells, but which do not support CD4-mediated HIV infection.

Additional experiments suggest that it is the physical distance between the extracellular domain of the CD4 molecule and the lipid bilayer that confers the ability to resist HIV infection. In a first experiment, we constructed a chimeric molecule bearing a deletion of the CD7 stalk and transmembrane domain; this deletion removed the proline rich region of the CD7 transmembrane portion. When this domain was fused to the extracellular domain of CD4, it maintained its ability to efficiently anchor the extracellular domain of the CD4 molecule, as measured by cell surface expression of the CD4 molecule (as described herein). However, the potential to resist syncytium formation induced by the HIV envelope glycoprotein was lost. Thus, deletion of the proline-rich region of the CD7 molecule, a region likely to form an α-helical coil structure, effectively reduced the distance between the extracellular domain of CD4 and the lipid bilayer and abrogated the ability of the chimera to resist syncytium formation.

In a second experiment, we, demonstrated that the ability to resist HIV-induced syncytium formation may be conferred upon a CD4/CD5 chimera which had previously been documented to serve as a transmembrane anchor for a CD4 extracellular domain but which was unable to resist HIV-induced syncytium formation. In this experiment, the hinge, CH2, and CH3 domains of the human IgG1 heavy chain were inserted into the CD4/CD5 molecule; the resulting chimera resisted syncytium formation, again suggesting that the distance afforded by the immunoglobulin domains is sufficient to confer resistance to HIV-induced syncytium formation.

In a third experiment, a CD4 domain was extended varying distances from the cell membrane using synthetic alpha helices of varying length. In particular, synthetic oligonucleotides representing repeated alpha helical motifs of lysine and glutamic acid residues flanked by two alanine residues were designed (see FIG. 28 for the primary nucleic acid and amino acid sequences). In previous studies, such amino acid sequences were found to occur with high frequency in alpha helices, suggesting that such repeated motifs would adopt an alpha helical conformation and that placement of such alpha helices between the transmembrane domain and extracellular domains of CD4 would project CD4 away from the cell membrane. By varying the length of the alpha helical segment, a calculation of the projection distance necessary to resist HIV entry was determined based on known values for alpha helical rise and turn. These results are presented in Table 1.

TABLE 1

|   | Syncytia Formation | Thy-1 Expression |
|---|---|---|
| A. CD4 + H + CH2 + CH3 + CD7tm + stk | − | − |
| B. CD4 (D1, D2) + H + CH2 + CH3 + CD7tm + stk | − | − |
| C. CD4 + CD7tm + stk | +/−[a] | + |
| D. CD4 + CD7tm (long version) | + | + |
| E. CD4 + CD7tm (short version) | + | + |
| F. CD4 + CD5tm | + | + |
| G. CD4 + CH2 + CH3 + CD5tm | − | − |
| H. CD4 + CH3 + CD5tm | − | ND |
| I. CD4 + CD34tm | + | + |
| J. CD4 + synthetic alpha helix (24 angstroms) + CD34tm | ND | − |
| K. CD4 + synthetic alpha helix (48 angstroms) + CD34tm | ND | +/−[a] |
| L. CD4 + synthetic alpha helix (72 angstroms) + CD34tm | ND | − |

[a]Substantial reduction in the number of syncytia or thy-1-expressing cells.

In this Table, "CD4" represents CD4(D1–D4) unless otherwise noted; "H" "CH2", and "CH3" represent the hinge, CH2, and CH3 regions of the human IgG1 heavy chain, respectively; "CD7tm and stk" represents the CD7 transmembrane and stalk regions; "CD7tm (long version)" and "CD7tm (short version)" represent respectively the CD7 transmembrane region and the CD7 transmembrane region deleted for the proline-rich domain (as discussed above); "CD5tm" represents the CD5 transmembrane region; and "CD34tm" represents the CD34 transmembrane region. In entries J–L, the length of the alpha helical region is denoted in angstroms; these values are based on the fact that there are 3.6 residues per turn of an alpha helix, corresponding to 5.4 Å (or 1.5Å per residue). Accordingly, a 16 residue alpha helix would project the extracellular domain of CD4 about 24 angstroms. The 48 and 72 angstrom alpha helices were constructed by sequential concatemerization of the BstY1 fragment into the fragment's unique Bam1 site (see FIG. 28), followed by selection of clones with the proper orientation.

Syncytia formation was scored in co-cultivation assays with HeLa cells expressing the HIV-1 envelope glycoprotein from the vaccinia virus vPE-16 construct (see above).

Thy-1 expression was measured as follows. A live retrovirus vector was constructed based on the hxb.2 clone of HIV-1. In this vector, the non-essential nef gene was replaced with the coding sequence of rat thy-1, an efficiently expressed cell surface molecule that is anchored to the membrane by a phosphatidyl-inositol linkage. The virus derived from this molecular clone, designated hxb/thy-1, was infectious as evidenced by its cytopathological effects and by the Production of p24 in culture supernatants of infected C8166 cells (a human CD4+ leukemic T-cell line). In addition, upon exposure to hxb/thy-1, HeLa cells transiently transfected with CD4 showed signs of thy-1 expression in as early as 18 hours post-infection, as would be expected of a message regulated in a nef-like manner. Messages encoded by the nef gene normally fall into a class of viral regulatory proteins which are multiply spliced and lack the rev-response element. These messages can accumulate constitutively in the cytoplasm as early viral gene products. The thy-1 messages were expected to be similarly regulated, that is, to occur early in the life cycle of the virus. In short, this system facilitated the assay of HIV entry, with thy-1 expression employed as a surrogate for viral entry. Various CD4-based chimeras were transiently transfected into HeLa cells using standard DEAE-dextran methods. The transfected cells were exposed to hxb/thy-1 virus at 48 hours post-transfection and scored for thy-1 expression at 24–48 hours post-infection. In the results shown in Table 1, thy-1 expression was measured at 24 hours post-infection using a commercially available Thy-1 monoclonal antibody (Accurate).

From the data presented in Table 1, we concluded that the extracellular domains of CD4 should optimally be projected away from the cell membrane by at least 48 angstroms, and preferably by at least 72 angstroms in order to resist HIV-1 infection.

Using a strategy similar to the general strategy described herein, chimeras based on anti-HIV envelope antibodies may be constructed which target HIV-infected cells. Examples of such antibodies are described in Gorny et al., *Proc. Natl. Acad. Sci. USA* 86:1624 (1989) and Marasco et al., *J. Clin. Invest.* 90:1467 (1992).

EXAMPLE XI

Additional T Cell Receptor and B Cell Receptor Trigger Proteins

Other intracellular and transmembrane signal transducing domains according to the invention may be derived from the T cell receptor proteins, CD3 delta and T3 gamma, and the B cell receptor proteins, mb1 and B29. The amino acid sequences of these proteins are shown in FIG. 16 (CD3 delta; SEQ ID NO: 24), FIG. 17 (T3 gamma; SEQ ID NO: 25), FIG. 18 (md1; SEQ ID NO: 26) and FIG. 19 (B29; SEQ ID NO: 27). The portions of the sequences sufficient for cytolytic signal transduction (and therefore preferably included in a chimeric receptor of the invention) are shown in brackets. Chimeric receptors which include these protein domains are constructed and used in the therapeutic methods of the invention generally as described above.

EXAMPLE XII

Experimental Methods

Vaccinia Infection and Radioimmunoprecipitation

Approximately 5×10⁶ CV1 cells were infected for one hour in serum free DME medium with recombinant vaccinia at a multiplicity of infection (moi) of at least ten (titer measured on CV1 cells). The cells were placed in fresh medium after infection and labelled metabolically with 200 μCi/ml ³⁵S-methionine plus cysteine (Tran³⁵S-label, ICN; Costo Mesa, Calif.) in methionine and cysteine free DMEM (Gibco; Grand Island, N.Y.) for six hours. The labelled cells were detached with PBS containing 1 mM EDTA, collected by centrifugation, and lysed in 1% NP-40, 0.1% SDS, 0.15 M NaCl, 0.05M Tris pH 8.0, 5 mM EDTA, and 1 mM PMSF. Nuclei were removed by centrifugation, and CD4 proteins immunoprecipitated with OKT4 antibody and anti-mouse IgG agarose (Cappel, Durham, N.C.). Samples were electrophoresed through 8% polyacrylamide/SDS gels under non-reducing (NR) and reducing (R) conditions. Gels containing $^{35}$S-labelled samples were impregnated with En$^3$Hance (New England Nuclear, Boston, Ma.) prior to autoradiography. Facilitated expression of the transmembrane form of CD16, CD16$_{TM}$, was measured by comparing its expression in CV1 cells singly infected with CD16$_{TM}$ with expression in cells coinfected with viruses encoding CD16$_{TM}$ and ζ or γ chimeras. After infection and incubation for six hours or more, cells were detached from plates with PBS, 1 mM EDTA and the expression of CD16TM or the chimeras was measured by indirect immunofluorescence and flow cytometry.

Calcium Flux Assay

Jurkat subline E6 (Weiss et al., *J. Immunol.* 133:123–128 (1984)) cells were infected with recombinant vaccinia viruses for one hour in serum free IMDM at an moi of 10 and incubateded for three to nine hours in IMDM, 10% FBS. Cells were collected by centrifugation and resuspended at 3×10$^6$ cells/ml in complete medium containing 1 mM Indo-1 acetomethoxyester (Grynkiewicz et al., *J. Biol. Chem.* 260:3340–3450 (1985)) (Molecular Probes) and incubated at 37° C. for 45 minutes. The Indo-1 loaded cells were pelleted and resuspended at 1×10$^6$/ml in serum free IMDM and stored at room temperature in the dark. Cells were analyzed for free calcium ion by simultaneous measurement of the violet and blue fluorescence emission by flow cytometry (Rabinovitch et al., *J. Immunol.* 137:952–961 (1986)). To initiate calcium flux, either phycoerythrin (PE)-conjugated Leu-3A (anti-CD4) (Becton Dickinson, Lincoln Park, N.J.) at 1 μg/ml was added to the cell suspension followed by 10 μg/ml of unconjugated goat anti-mouse IgG at time 0 or unconjugated 3G8 (anti-CD16) monoclonal antibody was added to the cell suspension at 10 μg/ml followed by 10 μg/ml of PE-conjugated Fab$_2$' goat anti-monse IgG at time 0. Histograms of the violet/blue emission ratio were collected from the PE positive (infected) cell population, which typically represented 40–80% of all cells. The T cell antigen receptor response in uninfected cells was triggered by antibody OKT3, without crosslinking. For experiments involving CD16 chimeric receptors, samples showing baseline drift toward lower intracellular calcium (without antibody) were excluded from the analysis. Histogram data were subsequently analyzed by conversion of the binary data to ASCII using Write Hand Man (Cooper City, Fla.) software, followed by analysis with a collection of FORTRAN programs. The violet/blue emission ratio prior to the addition of the second antibody reagents was used to establish the normalized initial ratio, set equal to unity, and the resting threshold ratio, set so that 10% of the resting population would exceed threshold.

Cytolysis Assay

Human T cell line WH3, a CD8$^+$ CD4$^-$ HLA B44 restricted cytolytic line was maintained in IMDM, 10% human serum with 100 U/ml of IL-2 and was periodically stimulated either nonspecifically with irradiated (3000 rad) HLA-unmatched peripheral blood lymphocytes and 1 μg/ml of phytohemagglutinin, or specifically, with irradiated B44bearing mononuclear cells. After one day of nonspecific stimulation, the PHA was diluted to 0.5 μg/ml by addition of fresh medium, and after three days the medium was changed. Cells were grown for at least 10 days following stimulation before use in cytotoxicity assays. The cells were infected with recombinant vaccinia at a multiplicity of infection of 6at least 10 for one hour in serum free medium, followed by incubation in complete medium for three hours. Cells were harvested by centrifugation and resuspended at a density of 1×10$^7$ cells/ml; 100 μl were added to each well of a U-bottom microtiter plate containing 100 μl/well of complete medium. Cells were diluted in two-fold serial steps. Two wells for each sample did not contain lymphocytes, to allow spontaneous chromium release and total chromium uptake to be measured. The target cells, from HeLa subline S3, were infected in 6.0 or 10.0 cm plates at an approximate moi of 10 for one hour in serum free medium, followed by incubation in complete medium for three hours. They were then detached from the dishes with PBS, 1 mM EDTA and counted. An aliquot of 10$^6$ target cells (HeLa, Raji, or RJ2.2.5 cells for the CD4 chimeric receptor experiments and 3G8 10-2 cells; Shen et al., *Mol. Immunol.* 26:959 (1989) for the CD16 chimeric receptor experiments) was centrifuged and resuspended in 50 μl of sterile $^{51}$Cr-sodium chromate (1 mCi/ml, Dupont Wilmington, Del.) for one hour at 37° C. with intermittent mixing, then washed three times with PBS. 100 μl of labelled cells resuspended in medium at 10$^5$ cells/ml were added to each well. Raji and RJ2.2.5 target cells were labelled in the same manner as HeLa cells. The microtiter plate was spun at 750×g for 1 minute and incubated for 4 hours at 37° C. At the end of the incubation period, the cells in each well were resuspended by gentle pipetting, a sample removed to determine the total counts incorporated, and the microtiter plate spun at 750×g for 1 minute. 100 μl aliquots of supernatant were removed and counted in a gamma ray scintillation counter. The percent killing was corrected for the fraction of infected target cells (usually 50–90%) measured by flow cytometry. For infected effector cells the effector:target ratio was corrected for the percent of cells infected (usually 20–50% for the CD4 chimeric receptor experiments and >70% for the CD16 chimeric receptor experiments).

In Vitro Mutagenesis of the ζ Sequence

To create point mutations in amino acid residues 11 and or 15 of the ζ sequence, synthetic oligonucleotide primers extending from the BamHI site upstream of the ζ transmembrane domain, and converting native ζ residue 11 from Cys to Gly (C11G) or residue 15 from Asp to Gly (D15G) or both (C11G/D15G) were prepared and used in PCR reactions to generate mutated fragments which were reinserted into the wild type CD4:ζ constructs.

To create ζ deletions, ζ cDNA sequences were amplified by PCR using synthetic oligonucleotide primers designed to create a stop codon (UAG) after residues 50, 59, or 65. The primers contained the cleavage site for the enzyme NotI indented five or six-residues from the 5' end, usually in a sequence of the form CGC GGG CGG CCG CTA (SEQ ID NO: 11), where the last three residues correspond to the stop anticodon. The NotI and stop anticodon sequences were followed by 18 or more residues complementary to the desired 3' end of the fragment. The resulting chimeras were designated CD16:ζY51*, CD16:ζE60* and CD16:ζD66* respectively. The BamHI site upstream of the transmembrane domain and the NotI site were used to generate fragments that were reintroduced into the wild type CD16:ζ construct. Monomeric ζ chimeras were created by liberating the ζ transmembrane and membrane proximal intracellular sequences by BamHI and SacI digestion of the Asp$^-$ and Cys$^-$ CD4:ζ construct described above and inserting the fragment into the CD16:ζE60* and CD16:ζD66* construct respectively. CD16:7:ζ(48–65) and CD16:7ζ(48–59) Tripartite Chimera construction.

To prepare the construct CD16:ζD66*, the ζ cDNA sequence corresponding to the transmembrane domain and the 17 following residues of the cytoplasmic domain was replaced by corresponding transmembrane and cytoplasmic domain obtained from the CD5 and CD7 cDNA. The CD5 and CD7 fragments were generated by a PCR reaction using forward oligonucleotides including a BamHI restriction cleavage site and corresponding to the region just upstream of the transmembrane domain of CD5 and CD7 respectively and the following reverse oligonucleotides overlapping the CD5 and CD7 sequences respectively and the ζ sequence which contained the SacI restriction cleavage site.

CD5:ζ: CGC GGG CTC GTT ATA GAG CTG GTT CTG GCG CTG CTT CTT CTG (SEQ ID NO: 12)

CD7:ζ: CGC GGG GAG CTC GTT ATA GAG CTG GTT TGC CGC CGA ATT CTT ATC CCG (SEQ ID NO: 13).

The CD5 and CD7 PCR products were digested with BamHI and SacI and ligated to BamHI and SacI digested CD16:ζE60* and replacing the ζ sequence from BamHI to SacI by the CD7 fragment. To make the constructs CD16:CD5 and CD16:CD7, CD5 and CD7 fragments were obtained by PCR using an oligonucleotide containing a NotI restriction cleavage site and encoding a stop codon (UAA) after the residue Gln416 and Ala193 of CD5 and CD7 respectively. The CD5 and CD7 PCR fragment were digested with BamHI and NotI and inserted in the CD16:ζAsp66* construct.

In Vitro Mutagenesis of the N-terminal Residues Within the ζ Cytolytic signal-Transducing Motif Synthetic oligonucleotide primers extending from the SacI site inside the ζ motif and converting native residue 48 from Asn to Ser (N48S), residue 50 from Leu to Ser (L50S) and residue 51 from Tyr to Phe (Y51F) were synthesized and used in a PCR reaction to generate fragments that were reintroduced into the wild type CD16:7:ζ(48–65) construct.

In Vitro Mutagenesis of c-terminal Residues Within the ζ Cytolytic Signal-Transducing Motif Synthetic oligonucleotide primers extending from the NotI site 3' to the stop codon and converting native residue 60 from Glu to Gln (E60Q), residue 61 from Glu to Gln (E61Q), residue 62 from Tyr to Phe or Ser (Y62F or Y62S) and residue 63 from Asp to Asn (D63N) were synthesized and used in PCR to generate fragments that were subcloned into the wild type CD16:ζD66* construct from the BamHI site to the NotI site.

CD16:7:ζ(33–65), CD16:7:ζ(71–104), CD16:7:ζ(104–137) Chimera Constructions

A CD7 transmembrane fragment bearing MluI and NotI sites at the junction between the transmembrane and intracellular domains was obtained by PCR using an oligonucleotide with the following sequence: CGC GGG GCG GCC ACG CGT CCT CGC CAG CAC ACA (SEQ ID NO:14). The resulting PCR fragment was digested with BamHI and NotI and reinserted into the CD16:7:ζ(48–65) construct. ζ fragments encoding residues 33 to 65, 71 to 104, and 104 to 137 were obtained by PCR reaction using pairs of primers containing MluI sites at the 5' end of the forward primers and stop codons followed by NotI sites at the 5' end of the reverse primers. In each case the restriction sites were indented six residues from the 5' terminus of the primer to insure restriction enzyme cleavage.

ζ 33: CGC GGG ACG CGT TTC AGC CGT CCT CGC CAG CAC ACA (SEQ ID NO: 15);

ζ 71: CGC GGG ACG CGT GAC CCT GAG ATG GGG GGA AAG (SEQ ID NO: 16); and

ζ 104: CGC GGG ACG CGT ATT GGG ATG AAA GGC GAG CGC (SEQ ID NO: 17).

Construction of FcRγIIA Deletion Mutants

Carboxyl terminal FcRIIA deletion mutants were constructed by PCR in the same fashion as for the full length constructs, converting the sequences encoding tyrosine at positions 282 and 298 into stop codons (TAA). The N-terminal deletions were generated by amplifying fragments encoding successively less of the intracellular domain by PCR, using oligonucleotides which allowed the resulting fragments to be inserted between MluI and NotI restriction sites into a previously constructed expression plasmid encoding the CD16 extracellular domain fused to the CD7 transmembrane domain, the latter terminating in a MluI site ant the junction between the transmembrane and the intracellular domain.

OTHER EMBODIMENTS

The examples described above demonstrate that aggregation of ζ, η, or γ chimeras suffices to initiate the cytolytic effector cell response in T cells. The known range of expression of ζ, η, and γ, which includes T lymphocytes, natural killer cells, basophilic granulocytes, macrophages and mast cells, suggests that conserved sequence motifs may interact with a sensory apparatus common to cells of hematopoietic origin and that an important component of host defense in the immune system may be mediated by receptor aggregation events.

The potency of the cytolytic response and the absence of a response to target cells bearing MHC class II receptors demonstrates that chimeras based on ζ, η, or γ form the basis for a genetic intervention for AIDS through adoptive immunotherapy. The broad distribution of endogenous ζ and γ and evidence that Fc receptors associated with γ mediate cytotoxicity in different cells types (Fanger et al., *Immunol. Today* 10:92–99 (1989)) allows a variety of cells to be considered for this purpose. For example, neutrophilic granulocytes, which have a very short lifespan ($\approx$4h) in circulation and are intensely cytolytic, are attractive target cells for expression of the chimeras. Infection of neutrophils with HIV is not likely to result in virus release, and the abundance of these cells (the most prevalent of the leukocytes) should facilitate host defense. Another attractive possibility for host cells are mature T cells, a population presently accessible to retroviral engineering (Rosenberg, S. A. *Sci Am.* 262:62–69 (1990)). With the aid of recombinant IL-2, T cell populations can be expanded in culture with relative ease, and the expanded populations typically have a limited lifespan when reinfused (Rosenberg et al., *N. Engl. J. Med.* 323:570–578 (1990)).

Under the appropriate conditions, HIV recognition by cells expressing CD4 chimeras should also provide mitogenic stimuli, allowing the possibility that the armed cell population could respond dynamically to the viral burden. Although we have focused here on the behavior of the fusion proteins in cytolytic T lymphocytes, expression of the chimeras in helper lymphocytes might provide an HIV-mobilized source of cytokines which could counteract the collapse of the helper cell subset in AIDS. Recent description of several schemes for engineering resistance to infection at steps other than virus penetration (Friedman et al., *Nature* 335:452–454 (1988); Green et al., *Cell* 58:215–223 (1989); Malim et al., *Cell* 58:205–214 (1989); Trono et al., *Cell* 59:113–120 (1989); Buonocore et al., *Nature* 345:625–628 (1990)) suggests that cells bearing CD4 chimeras could be designed to thwart virus production by expression of appropriate agents having an intracellular site of action.

The ability to transmit signals to T lymphocytes through autonomous chimeras also provides the ability for the regulation of retrovirally engineered lymphocytes in vivo. Crosslinking stimuli, mediated for example by specific IgM antibodies engineered to remove complement-binding domains, may allow such lymphocytes to increase in number in situ, while treatment with similar specific IgG antibodies (for example recognizing an amino acid variation engineered into the chimeric chain) could selectively deplete the engineered population. Additionally, anti-CD4 IgM antibodies do not require additional crosslinking to mobilize calcium in Jurkat cells expressing CD4:ζ chimeras. The ability to regulate cell populations without recourse to repeated extracorporeal amplification may substantially extend the range and efficacy of current uses proposed for genetically engineered T cells.

While the invention has been described in connection with specific embodiments thereof, it will be understood that it is capable of further modifications and this application is intended to cover variations, uses, or adaptations of the invention and including such departures from the present disclosure as come within the art to which the invention pertains and as may be applied to the essential features hereinbefore set forth as follows in the scope of the appended claims.

What is claimed is:

1. A method of directing a cellular immune response against HIV or an HIV-infected cell in a mammal, said method comprising administering to said mammal an effective amount of therapeutic cells, said therapeutic cells expressing a membrane-bound, proteinaceous chimeric receptor comprising (a) an extracellular portion which includes a fragment of CD4 which specifically recognizes and binds said HIV or said HIV-infected cell but which does not mediate HIV infection, (b) a transmembrane portion, and (c) an intracellular portion which signals said therapeutic cell to destroy said receptor-bound HIV or said HIV-infected cell.

2. The method of claim 1, wherein said CD4 fragment consists of amino acids 1–394 of SEQ ID NO: 29.

3. The method of claim 1, wherein said CD4 fragment consists of amino acids 1–200 of SEQ ID NO: 31.

4. The method of claim 1, wherein said transmembrane portion comprises the CD7 transmembrane domain of SEQ ID NO: 35.

5. The method of claim 1, wherein said extracellular portion further comprises the hinge, CH2, and CH3 domains of the human IgG1 molecule of SEQ ID NO: 32.

6. The method of claim 1, wherein said CD4 fragment is separated from said therapeutic cell membrane by between 48 and 72 angstroms.

7. The method of claim 1, wherein said intracellular portion is the signal-transducing portion of a T cell receptor protein, a B cell receptor protein, or an Fc receptor protein.

8. The method of claim 7, wherein said T cell receptor protein is ζ.

9. The method of claim 1, wherein said therapeutic cells are selected from the group consisting of: (a) T lymphocytes; (b) cytotoxic T lymphocytes; (c) natural killer cells; (d) neutrophils; (e) granulocytes; (f) macrophages; and (g) mast cells.

10. The method of claim 1, wherein said transmembrane portion comprises a CD5 transmembrane domain.

11. The method of claim 1, wherein said transmembrane portion comprises a CD34 transmembrane domain.

12. The method of claim 1, wherein said CD4 fragment is separated from said therapeutic cell membrane by two or three proteinaceous alpha helices.

13. The method of claim 1, wherein said mammal is a human.

* * * * *

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
        (A) LENGTH: 1728 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:1:

```
ATGAACCGGG GAGTCCCTTT TAGGCACTTG CTTCTGGTGC TGCAACTGGC GCTCCTCCCA        60

GCAGCCACTC AGGGAAACAA AGTGGTGCTG GGCAAAAAAG GGGATACAGT GGAACTGACC       120

TGTACAGCTT CCCAGAAGAA GAGCATACAA TTCCACTGGA AAAACTCCAA CCAGATAAAG       180

ATTCTGGGAA ATCAGGGCTC CTTCTTAACT AAAGGTCCAT CCAAGCTGAA TGATCGCGCT       240

GACTCAAGAA GAAGCCTTTG GGACCAAGGA AACTTCCCCC TGATCATCAA GAATCTTAAG       300

ATAGAAGACT CAGATACTTA CATCTGTGAA GTGGAGGACC AGAAGGAGGA GGTGCAATTG       360

CTAGTGTTCG GATTGACTGC CAACTCTGAC ACCCACCTGC TTCAGGGGCA GAGCCTGACC       420

CTGACCTTGG AGAGCCCCCC TGGTAGTAGC CCCTCAGTGC AATGTAGGAG TCCAAGGGGT       480

AAAAACATAC AGGGGGGGAA GACCCTCTCC GTGTCTCAGC TGGAGCTCCA GGATAGTGGC       540

ACCTGGACAT GCACTGTCTT GCAGAACCAG AAGAAGGTGG AGTTCAAAAT AGACATCGTG       600

GTGCTAGCTT TCCAGAAGGC CTCCAGCATA GTCTATAAGA AAGAGGGGA ACAGGTGGAG       660

TTCTCCTTCC CACTCGCCTT TACAGTTGAA AAGCTGACGG GCAGTGGCGA GCTGTGGTGG       720

CAGGCGGAGA GGGCTTCCTC CTCCAAGTCT TGGATCACCT TTGACCTGAA GAACAAGGAA       780

GTGTCTGTAA ACGGGTTAC CCAGGACCCT AAGCTCCAGA TGGGCAAGAA GCTCCCGCTC       840

CACCTCACCC TGCCCCAGGC CTTGCCTCAG TATGCTGGCT CTGGAAACCT CACCCTGGCC       900

CTTGAAGCGA AAACAGGAAA GTTGCATCAG GAAGTGAACC TGGTGGTGAT GAGAGCCACT       960

CAGCTCCAGA AAAATTTGAC CTGTGAGGTG TGGGGACCCA CCTCCCCTAA GCTGATGCTG      1020

AGCTTGAAAC TGGAGAACAA GGAGGCAAAG GTCTCGAAGC GGGAGAAGCC GGTGTGGGTG      1080

CTGAACCCTG AGGCGGGGAT GTGGCAGTGT CTGCTGAGTG ACTCGGGACA GGTCCTGCTG      1140

GAATCCAACA TCAAGGTTCT GCCCACATGG TCCACCCCGG TGCACGCGGA TCCCAAACTC      1200

TGCTACTTGC TAGATGGAAT CCTCTTCATC TACGGAGTCA TCATCACAGC CCTGTACCTG      1260

AGAGCAAAAT TCAGCAGGAG TGCAGAGACT GCTGCCAACC TGCAGGACCC CAACCAGCTC      1320

TACAATGAGC TCAATCTAGG GCGAAGAGAG GAATATGACG TCTTGGAGAA GAAGCGGGCT      1380

CGGGATCCAG AGATGGGAGG CAAACAGCAG AGGAGGAGGA ACCCCCAGGA AGGCGTATAC      1440

AATGCACTGC AGAAAGACAA GATGCCAGAA GCCTACAGTG AGATCGGCAC AAAAGGCGAG      1500
```

```
AGGCGGAGAG GCAAGGGGCA CGATGGCCTT TACCAGGACA GCCACTTCCA AGCAGTGCAG    1560

TTCGGGAACA GAAGAGAGAG AGAAGGTTCA GAACTCACAA GGACCCTTGG GTTAAGAGCC    1620

CGCCCCAAAG GTGAAAGCAC CCAGCAGAGT AGCCAATCCT GTGCCAGCGT CTTCAGCATC    1680

CCCACTCTGT GGAGTCCATG GCCACCCAGT AGCAGCTCCC AGCTCTAA                 1728
```

(2) INFORMATION FOR SEQ ID NO:2:

(i) SEQUENCE CHARACTERISTICS:
        (A) LENGTH: 1389 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATGAACCGGG GAGTCCCTTT TAGGCACTTG CTTCTGGTGC TGCAACTGGC GCTCCTCCCA      60

GCAGCCACTC AGGGAAACAA AGTGGTGCTG GGCAAAAAAG GGGATACAGT GGAACTGACC     120

TGTACAGCTT CCCAGAAGAA GAGCATACAA TTCCACTGGA AAAACTCCAA CCAGATAAAG     180

ATTCTGGGAA ATCAGGGCTC CTTCTTAACT AAAGGTCCAT CCAAGCTGAA TGATCGCGCT     240

GACTCAAGAA GAAGCCTTTG GGACCAAGGA AACTTCCCCC TGATCATCAA GAATCTTAAG     300

ATAGAAGACT CAGATACTTA CATCTGTGAA GTGGAGGACC AGAAGGAGGA GGTGCAATTG     360

CTAGTGTTCG GATTGACTGC CAACTCTGAC ACCCACCTGC TTCAGGGGCA GAGCCTGACC     420

CTGACCTTGG AGAGCCCCCC TGGTAGTAGC CCCTCAGTGC AATGTAGGAG TCCAAGGGGT     480

AAAAACATAC AGGGGGGGAA GACCCTCTCC GTGTCTCAGC TGGAGCTCCA GGATAGTGGC     540

ACCTGGACAT GCACTGTCTT GCAGAACCAG AAGAAGGTGG AGTTCAAAAT AGACATCGTG     600

GTGCTAGCTT TCCAGAAGGC CTCCAGCATA GTCTATAAGA AGAGGGGGA ACAGGTGGAG      660

TTCTCCTTCC CACTCGCCTT TACAGTTGAA AAGCTGACGG GCAGTGGCGA GCTGTGGTGG     720

CAGGCGGAGA GGGCTTCCTC CTCCAAGTCT TGGATCACCT TTGACCTGAA GAACAAGGAA     780

GTGTCTGTAA ACGGGTTAC CCAGGACCCT AAGCTCCAGA TGGGCAAGAA GCTCCCGCTC      840

CACCTCACCC TGCCCCAGGC CTTGCCTCAG TATGCTGGCT CTGGAAACCT CACCCTGGCC     900

CTTGAAGCGA AAACAGGAAA GTTGCATCAG GAAGTGAACC TGGTGGTGAT GAGAGCCACT     960

CAGCTCCAGA AAAATTTGAC CTGTGAGGTG TGGGGACCCA CCTCCCCTAA GCTGATGCTG    1020

AGCTTGAAAC TGGAGAACAA GGAGGCAAAG GTCTCGAAGC GGGAGAAGCC GGTGTGGGTG    1080

CTGAACCCTG AGGCGGGGAT GTGGCAGTGT CTGCTGAGTG ACTCGGGACA GGTCCTGCTG    1140

GAATCCAACA TCAAGGTTCT GCCCACATGG TCCACCCCGG TGCACGCGGA TCCGCAGCTC    1200

TGCTATATCC TGGATGCCAT CCTGTTTTTG TATGGTATTG TCCTTACCCT GCTCTACTGT    1260

CGACTCAAGA TCCAGGTCCG AAAGGCAGAC ATAGCCAGCC GTGAGAAATC AGATGCTGTC    1320

TACACGGGCC TGAACACCCG GAACCAGGAG ACATATGAGA CTCTGAAACA TGAGAAACCA    1380

CCCCAATAG                                                            1389
```

(2) INFORMATION FOR SEQ ID NO:3:

(i) SEQUENCE CHARACTERISTICS:
        (A) LENGTH: 1599 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

```
ATGAACCGGG GAGTCCCTTT TAGGCACTTG CTTCTGGTGC TGCAACTGGC GCTCCTCCCA      60
GCAGCCACTC AGGGAAACAA AGTGGTGCTG GGCAAAAAAG GGGATACAGT GGAACTGACC     120
TGTACAGCTT CCCAGAAGAA GAGCATACAA TTCCACTGGA AAAACTCCAA CCAGATAAAG     180
ATTCTGGGAA ATCAGGGCTC CTTCTTAACT AAAGGTCCAT CCAAGCTGAA TGATCGCGCT     240
GACTCAAGAA GAAGCCTTTG GGACCAAGGA AACTTCCCCC TGATCATCAA GAATCTTAAG     300
ATAGAAGACT CAGATACTTA CATCTGTGAA GTGGAGGACC AGAAGGAGGA GGTGCAATTG     360
CTAGTGTTCG GATTGACTGC CAACTCTGAC ACCCACCTGC TTCAGGGGCA GAGCCTGACC     420
CTGACCTTGG AGAGCCCCCC TGGTAGTAGC CCCTCAGTGA ATGTAGGAG TCCAAGGGGT      480
AAAAACATAC AGGGGGGGAA GACCCTCTCC GTGTCTCAGC TGGAGCTCCA GGATAGTGGC     540
ACCTGGACAT GCACTGTCTT GCAGAACCAG AAGAAGGTGA AGTTCAAAAT AGACATCGTG     600
GTGCTAGCTT TCCAGAAGGC CTCCAGCATA GTCTATAAGA AGAGGGGGA ACAGGTGGAG      660
TTCTCCTTCC CACTCGCCTT TACAGTTGAA AAGCTGACGG GCAGTGGCGA GCTGTGGTGG     720
CAGGCGGAGA GGGCTTCCTC CTCCAAGTCT TGGATCACCT TTGACCTGAA GAACAAGGAA     780
GTGTCTGTAA AACGGGTTAC CCAGGACCCT AAGCTCCAGA TGGGCAAGAA GCTCCCGCTC     840
CACCTCACCC TGCCCCAGGC CTTGCCTCAG TATGCTGGCT CTGGAAACCT CACCCTGGCC     900
CTTGAAGCGA AAACAGGAAA GTTGCATCAG GAAGTGAACC TGGTGGTGAT GAGAGCCACT     960
CAGCTCCAGA AAAATTTGAC CTGTGAGGTG TGGGGACCCA CCTCCCCTAA GCTGATGCTG    1020
AGCTTGAAAC TGGAGAACAA GGAGGCAAAG GTCTCGAAGC GGGAGAAGCC GGTGTGGGTG    1080
CTGAACCCTG AGGCGGGGAT GTGGCAGTGT CTGCTGAGTG ACTCGGGACA GGTCCTGCTG    1140
GAATCCAACA TCAAGGTTCT GCCCACATGG TCCACCCCGG TGCACGCGGA TCCCAAACTC    1200
TGCTACCTGC TGGATGGAAT CCTCTTCATC TATGGTGTCA TTCTCACTGC CTTGTTCCTG    1260
AGAGTGAAGT TCAGCAGGAG CGCAGAGCCC CCCGCGTACC AGCAGGGCCA GAACCAGCTC    1320
TATAACGAGC TCAATCTAGG ACGAAGAGAG GAGTACGATG TTTTGGACAA GAGACGTGGC    1380
CGGGACCCTG AGATGGGGGG AAAGCCGAGA AGGAAGAACC CTCAGGAAGG CCTGTACAAT    1440
GAACTGCAGA AAGATAAGAT GGCGGAGGCC TACAGTGAGA TTGGGATGAA AGGCGAGCGC    1500
CGGAGGGGCA AGGGGCACGA TGGCCTTTAC CAGGGTCTCA GTACAGCCAC CAAGGACACC    1560
TACGACGCCC TTCACATGCA GGCCCTGCCC CCTCGCTAA                           1599
```

(2) INFORMATION FOR SEQ ID NO:4:

(i) SEQUENCE CHARACTERISTICS:
        (A) LENGTH: 575 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Met Asn Arg Gly Val Pro Phe Arg His Leu Leu Leu Val Leu Gln Leu
 1               5                  10                  15

Ala Leu Leu Pro Ala Ala Thr Gln Gly Asn Lys Val Val Leu Gly Lys
            20                  25                  30

Lys Gly Asp Thr Val Glu Leu Thr Cys Thr Ala Ser Gln Lys Lys Ser
        35                  40                  45
```

-continued

```
Ile Gln Phe His Trp Lys Asn Ser Asn Gln Ile Lys Ile Leu Gly Asn
 50                  55                  60
Gln Gly Ser Phe Leu Thr Lys Gly Pro Ser Lys Leu Asn Asp Arg Ala
 65                  70                  75                  80
Asp Ser Arg Arg Ser Leu Trp Asp Gln Gly Asn Phe Pro Leu Ile Ile
                 85                  90                  95
Lys Asn Leu Lys Ile Glu Asp Ser Asp Thr Tyr Ile Cys Glu Val Glu
                100                 105                 110
Asp Gln Lys Glu Glu Val Gln Leu Leu Val Phe Gly Leu Thr Ala Asn
            115                 120                 125
Ser Asp Thr His Leu Leu Gln Gly Gln Ser Leu Thr Leu Thr Leu Glu
130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
        195                 200                 205
Ser Ile Val Tyr Lys Lys Glu Gly Glu Gln Val Glu Phe Ser Phe Pro
210                 215                 220
Leu Ala Phe Thr Val Glu Lys Leu Thr Gly Ser Gly Glu Leu Trp Trp
225                 230                 235                 240
Gln Ala Glu Arg Ala Ser Ser Ser Lys Ser Trp Ile Thr Phe Asp Leu
                245                 250                 255
Lys Asn Lys Glu Val Ser Val Lys Arg Val Thr Gln Asp Pro Lys Leu
            260                 265                 270
Gln Met Gly Lys Lys Leu Pro Leu His Leu Thr Leu Pro Gln Ala Leu
        275                 280                 285
Pro Gln Tyr Ala Gly Ser Gly Asn Leu Thr Leu Ala Leu Glu Ala Lys
    290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Pro Val Trp Val Leu Asn Pro Glu Ala Gly Met Trp
        355                 360                 365
Gln Cys Leu Leu Ser Asp Ser Gly Gln Val Leu Leu Glu Ser Asn Ile
    370                 375                 380
Lys Val Leu Pro Thr Trp Ser Thr Pro Val His Ala Asp Pro Lys Leu
385                 390                 395                 400
Cys Tyr Leu Leu Asp Gly Ile Leu Phe Ile Tyr Gly Val Ile Ile Thr
                405                 410                 415
Ala Leu Tyr Leu Arg Ala Lys Phe Ser Arg Ser Ala Glu Thr Ala Ala
            420                 425                 430
Asn Leu Gln Asp Pro Asn Gln Leu Tyr Asn Glu Leu Asn Leu Gly Arg
        435                 440                 445
Arg Glu Glu Tyr Asp Val Leu Glu Lys Lys Arg Ala Arg Asp Pro Glu
    450                 455                 460
Met Gly Gly Lys Gln Gln Arg Arg Arg Asn Pro Gln Glu Gly Val Tyr
```

```
465                 470                 475                 480
Asn Ala Leu Gln Lys Asp Lys Met Pro Glu Ala Tyr Ser Glu Ile Gly
                485                 490                 495

Thr Lys Gly Glu Arg Arg Gly Lys Gly His Asp Gly Leu Tyr Gln
            500                 505                 510

Asp Ser His Phe Gln Ala Val Gln Phe Gly Asn Arg Arg Glu Arg Glu
            515                 520                 525

Gly Ser Glu Leu Thr Arg Thr Leu Gly Leu Arg Ala Arg Pro Lys Gly
    530                 535                 540

Glu Ser Thr Gln Gln Ser Ser Gln Ser Cys Ala Ser Val Phe Ser Ile
545                 550                 555                 560

Pro Thr Leu Trp Ser Pro Trp Pro Ser Ser Ser Gln Leu
                565                 570                 575

(2) INFORMATION FOR SEQ ID NO:5:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Met Asn Arg Gly Val Pro Phe Arg His Leu Leu Leu Val Leu Gln Leu
1               5                   10                  15

Ala Leu Leu Pro Ala Ala Thr Gln Gly Asn Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
    195                 200                 205

Ser Ile Val Tyr Lys Lys Glu Gly Glu Gln Val Glu Phe Ser Phe Pro
    210                 215                 220

Leu Ala Phe Thr Val Glu Lys Leu Thr Gly Ser Gly Glu Leu Trp Trp
225                 230                 235                 240

Gln Ala Glu Arg Ala Ser Ser Ser Lys Ser Trp Ile Thr Phe Asp Leu
```

```
                   245                 250                 255
Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
        290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
            340                 345                 350

Lys Arg Glu Lys Pro Val Trp Val Leu Asn Pro Glu Ala Gly Met Trp
        355                 360                 365

Gln Cys Leu Leu Ser Asp Ser Gly Gln Val Leu Leu Glu Ser Asn Ile
    370                 375                 380

Lys Val Leu Pro Thr Trp Ser Thr Pro Val His Ala Asp Pro Gln Leu
385                 390                 395                 400

Cys Tyr Ile Leu Asp Ala Ile Leu Phe Leu Tyr Gly Ile Val Leu Thr
                405                 410                 415

Leu Leu Tyr Cys Arg Leu Lys Ile Gln Val Arg Lys Ala Asp Ile Ala
            420                 425                 430

Ser Arg Glu Lys Ser Asp Ala Val Tyr Thr Gly Leu Asn Thr Arg Asn
        435                 440                 445

Gln Glu Thr Tyr Glu Thr Leu Lys His Glu Lys Pro Pro Gln
    450                 455                 460

(2) INFORMATION FOR SEQ ID NO:6:

(i) SEQUENCE CHARACTERISTICS:
        (A) LENGTH: 532 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Met Asn Arg Gly Val Pro Phe Arg His Leu Leu Leu Val Leu Gln Leu
1               5                   10                  15

Ala Leu Leu Pro Ala Ala Thr Gln Gly Asn Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
```

```
            130                 135                 140
Ser Pro Pro Gly Ser Ser Pro Ser Val Gln Cys Arg Ser Pro Arg Gly
145                 150                 155                 160
Lys Asn Ile Gln Gly Gly Lys Thr Leu Ser Val Ser Gln Leu Glu Leu
                165                 170                 175
Gln Asp Ser Gly Thr Trp Thr Cys Thr Val Leu Gln Asn Gln Lys Lys
            180                 185                 190
Val Glu Phe Lys Ile Asp Ile Val Val Leu Ala Phe Gln Lys Ala Ser
                195                 200                 205
Ser Ile Val Tyr Lys Lys Glu Gly Glu Gln Val Glu Phe Ser Phe Pro
            210                 215                 220
Leu Ala Phe Thr Val Glu Lys Leu Thr Gly Ser Gly Glu Leu Trp Trp
225                 230                 235                 240
Gln Ala Glu Arg Ala Ser Ser Lys Ser Trp Ile Thr Phe Asp Leu
                245                 250                 255
Lys Asn Lys Glu Val Ser Val Lys Arg Val Thr Gln Asp Pro Lys Leu
                260                 265                 270
Gln Met Gly Lys Lys Leu Pro Leu His Leu Thr Leu Pro Gln Ala Leu
            275                 280                 285
Pro Gln Tyr Ala Gly Ser Gly Asn Leu Thr Leu Ala Leu Glu Ala Lys
        290                 295                 300
Thr Gly Lys Leu His Gln Glu Val Asn Leu Val Val Met Arg Ala Thr
305                 310                 315                 320
Gln Leu Gln Lys Asn Leu Thr Cys Glu Val Trp Gly Pro Thr Ser Pro
                325                 330                 335
Lys Leu Met Leu Ser Leu Lys Leu Glu Asn Lys Glu Ala Lys Val Ser
            340                 345                 350
Lys Arg Glu Lys Pro Val Trp Val Leu Asn Pro Glu Ala Gly Met Trp
        355                 360                 365
Gln Cys Leu Leu Ser Asp Ser Gly Gln Val Leu Leu Glu Ser Asn Ile
        370                 375                 380
Lys Val Leu Pro Thr Trp Ser Thr Pro Val His Ala Asp Pro Lys Leu
385                 390                 395                 400
Cys Tyr Leu Leu Asp Gly Ile Leu Phe Ile Tyr Gly Val Ile Leu Thr
                405                 410                 415
Ala Leu Phe Leu Arg Val Lys Phe Ser Arg Ser Ala Glu Pro Pro Ala
            420                 425                 430
Tyr Gln Gln Gly Gln Asn Gln Leu Tyr Asn Glu Leu Asn Leu Gly Arg
        435                 440                 445
Arg Glu Glu Tyr Asp Val Leu Asp Lys Arg Arg Gly Arg Asp Pro Glu
    450                 455                 460
Met Gly Gly Lys Pro Arg Arg Lys Asn Pro Gln Glu Gly Leu Tyr Asn
465                 470                 475                 480
Glu Leu Gln Lys Asp Lys Met Ala Glu Ala Tyr Ser Glu Ile Gly Met
            485                 490                 495
Lys Gly Glu Arg Arg Arg Gly Lys Gly His Asp Gly Leu Tyr Gln Gly
        500                 505                 510
Leu Ser Thr Ala Thr Lys Asp Thr Tyr Asp Ala Leu His Met Gln Ala
        515                 520                 525
Leu Pro Pro Arg
        530

(2) INFORMATION FOR SEQ ID NO:7:
```

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO:7:

CGCGGGGTGA CCGTGCCCTC CAGCAGCTTG GGC                                33

(2) INFORMATION FOR SEQ ID NO:8:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO:8:

CGCGGGGATC CGTCGTCCAG AGCCCGTCCA GCTCCCCGTC CTGGGCCTCA              50

(2) INFORMATION FOR SEQ ID NO:9:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO:9:

CGCGGGCGGC CGCGACGCCG GCCAAGACAG CAC                                33

(2) INFORMATION FOR SEQ ID NO:10:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO:10:

CGCGTTGACG AGCAGCCAGT TGGGCAGCAG CAG                                33

(2) INFORMATION FOR SEQ ID NO:11:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: Other (xi) SEQUENCE DESCRIPTION: SEQ ID NO:11:

CGCGGGCGGC CGCTA                                                    15

(2) INFORMATION FOR SEQ ID NO:12:

(i) SEQUENCE CHARACTERISTICS:
          (A) LENGTH: 42 base pairs
          (B) TYPE: nucleic acid

```
        (C) STRANDEDNESS: single
        (D) TOPOLOGY: linear (ii) MOLECULE TYPE: Other (xi) SEQUENCE DESCRIPTION: SEQ ID NO:12:

CGCGGGCTCG TTATAGAGCT GGTTCTGGCG CTGCTTCTTC TG                      42

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:13:

CGCGGGGAGC TCGTTATAGA GCTGGTTTGC CGCCGAATTC TTATCCCG                48

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:14:

CGCGGGGCGG CCACGCGTCC TCGCCAGCAC ACA                                33

(2) INFORMATION FOR SEQ ID NO:15:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:15:

CGCGGGACGC GTTTCAGCCG TCCTCGCCAG CACACA                             36

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

CGCGGGACGC GTGACCCTGA GATGGGGGGA AAG                                33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other
```

(xi) SEQUENCE DESCRIPTION: SEQ ID NO:17:

CGCGGGACGC GTATTGGGAT GAAAGGCGAG CGC                             33

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:18:

CCCGGATCCC AGCATGGGCA GCTCTT                                    26

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

CGCGGGGCGG CCGCTTTAGT TATTACTGTT GACATGGTCG TT                  42

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:20:

GCGGGGGGAT CCCACTGTCC AAGCTCCCAG CTCTTCACCG                     40

(2) INFORMATION FOR SEQ ID NO:21:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:21:

GCGGGGCGG CCGCCTAAAT ACGGTTCTGG TC                              32

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:22:

TCAGAAAGAG ACAACCTGAA GAAACCAACA A                              31

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:23:

TTGTTGGTTT CTTCAGGTTG TGTCTTTCTG A                        31

(2) INFORMATION FOR SEQ ID NO:24:

(i) SEQUENCE CHARACTERISTICS:
        (A) LENGTH: 171 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:24:

```
Met Glu His Ser Thr Phe Leu Ser Gly Leu Val Leu Ala Thr Leu Leu
 1               5                  10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ala Ile Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170
```

(2) INFORMATION FOR SEQ ID NO:25:

(i) SEQUENCE CHARACTERISTICS:
        (A) LENGTH: 182 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:25:

```
Met Glu Gln Gly Lys Gly Leu Ala Val Leu Ile Leu Ala Ile Ile Leu
 1               5                  10                  15

Leu Gln Gly Thr Leu Ala Gln Ser Ile Lys Gly Asn His Leu Val Lys
```

```
                    20                  25                  30
Val Tyr Asp Tyr Gln Glu Asp Gly Ser Val Leu Leu Thr Cys Asp Ala
                35                  40                  45
Glu Ala Lys Asn Ile Thr Trp Phe Lys Asp Gly Lys Met Ile Gly Phe
    50                  55                  60
Leu Thr Glu Asp Lys Lys Lys Trp Asn Leu Gly Ser Asn Ala Lys Asp
65                  70                  75                  80
Pro Arg Gly Met Tyr Gln Cys Lys Gly Ser Gln Asn Lys Ser Lys Pro
                85                  90                  95
Leu Gln Val Tyr Tyr Arg Met Cys Gln Asn Cys Ile Glu Leu Asn Ala
                100                 105                 110
Ala Thr Ile Ser Gly Phe Leu Phe Ala Glu Ile Val Ser Ile Phe Val
                115                 120                 125
Leu Ala Val Gly Val Tyr Phe Ile Ala Gly Gln Asp Gly Val Arg Gln
                130                 135                 140
Ser Arg Ala Ser Asp Lys Gln Thr Leu Leu Pro Asn Asp Gln Leu Tyr
145                 150                 155                 160
Gln Pro Leu Lys Asp Arg Glu Asp Asp Gln Tyr Ser His Leu Gln Gly
                165                 170                 175
Asn Gln Leu Arg Arg Asn
                180

(2) INFORMATION FOR SEQ ID NO:26:

(i) SEQUENCE CHARACTERISTICS:
        (A) LENGTH: 220 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

Met Pro Gly Gly Leu Glu Ala Leu Arg Ala Leu Pro Leu Leu Leu Phe
1                   5                   10                  15
Leu Ser Tyr Ala Cys Leu Gly Pro Gly Cys Gln Ala Leu Arg Val Glu
                20                  25                  30
Gly Gly Pro Pro Ser Leu Thr Val Asn Leu Gly Glu Glu Ala Arg Leu
                35                  40                  45
Thr Cys Glu Asn Asn Gly Arg Asn Pro Asn Ile Thr Trp Trp Phe Ser
    50                  55                  60
Leu Gln Ser Asn Ile Thr Trp Pro Pro Val Pro Leu Gly Pro Gly Gln
65                  70                  75                  80
Gly Thr Thr Gly Gln Leu Phe Phe Pro Glu Val Asn Lys Asn Thr Gly
                85                  90                  95
Ala Cys Thr Gly Cys Gln Val Ile Glu Asn Asn Ile Leu Lys Arg Ser
                100                 105                 110
Cys Gly Thr Tyr Leu Arg Val Arg Asn Pro Val Pro Arg Pro Phe Leu
                115                 120                 125
Asp Met Gly Glu Gly Thr Lys Asn Arg Ile Ile Thr Ala Glu Gly Ile
                130                 135                 140
Ile Leu Leu Phe Cys Ala Val Val Pro Gly Thr Leu Leu Leu Phe Arg
145                 150                 155                 160
Lys Arg Trp Gln Asn Glu Lys Phe Gly Val Asp Met Pro Asp Asp Tyr
                165                 170                 175
Glu Asp Glu Asn Leu Tyr Glu Gly Leu Asn Leu Asp Asp Cys Ser Met
```

```
                    180             185             190
Tyr Glu Asp Ile Ser Arg Gly Leu Gln Gly Thr Tyr Gln Asp Val Gly
        195             200             205

Asn Leu His Ile Gly Asp Ala Gln Leu Glu Lys Pro
        210             215             220
```

(2) INFORMATION FOR SEQ ID NO:27:

(i) SEQUENCE CHARACTERISTICS:
        (A) LENGTH: 228 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

```
Met Ala Thr Leu Val Leu Ser Ser Met Pro Cys His Trp Leu Leu Phe
 1               5                  10                  15

Leu Leu Leu Leu Phe Ser Gly Glu Pro Val Pro Ala Met Thr Ser Ser
            20                  25                  30

Asp Leu Pro Leu Asn Phe Gln Gly Ser Pro Cys Ser Gln Ile Trp Gln
        35                  40                  45

His Pro Arg Phe Ala Ala Lys Lys Arg Ser Ser Met Val Lys Phe His
    50                  55                  60

Cys Tyr Thr Asn His Ser Gly Ala Leu Thr Trp Phe Arg Lys Arg Gly
65                  70                  75                  80

Ser Gln Gln Pro Gln Glu Leu Val Ser Glu Glu Gly Arg Ile Val Gln
                85                  90                  95

Thr Gln Asn Gly Ser Val Tyr Thr Leu Thr Ile Gln Asn Ile Gln Tyr
            100                 105                 110

Glu Asp Asn Gly Ile Tyr Phe Cys Lys Gln Lys Cys Asp Ser Ala Asn
        115                 120                 125

His Asn Val Thr Asp Ser Cys Gly Thr Glu Leu Leu Val Leu Gly Phe
    130                 135                 140

Ser Thr Leu Asp Gln Leu Lys Arg Arg Asn Thr Leu Lys Asp Gly Ile
145                 150                 155                 160

Ile Leu Ile Gln Thr Leu Leu Ile Ile Leu Phe Ile Ile Val Pro Ile
                165                 170                 175

Phe Leu Leu Leu Asp Lys Asp Asp Gly Lys Ala Gly Met Glu Glu Asp
            180                 185                 190

His Thr Tyr Glu Gly Leu Asn Ile Asp Gln Thr Ala Thr Tyr Glu Asp
        195                 200                 205

Ile Val Thr Leu Arg Thr Gly Glu Val Lys Trp Ser Val Gly Glu His
    210                 215                 220

Pro Gly Gln Glu
225
```

(2) INFORMATION FOR SEQ ID NO:28:

(i) SEQUENCE CHARACTERISTICS:
        (A) LENGTH: 1304 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

-continued

```
GCCTGTTTGA GAAGCAGCGG GCAAGAAAGA CGCAAGCCCA GAGGCCCTGC CATTTCTGTG     60

GGCTCAGGTC CCTACTGGCT CAGGCCCCTG CCTCCCTCGG CAAGGCCACA ATGAACCGGG    120

GAGTCCCTTT TAGGCACTTG CTTCTGGTGC TGCAACTGGC GCTCCTCCCA GCAGCCACTC    180

AGGGAAACAA AGTGGTGCTG GCAAAAAAG GGGATACAGT GGAACTGACC TGTACAGCTT     240

CCCAGAAGAA GAGCATACAA TTCCACTGGA AAAACTCCAA CCAGATAAAG ATTCTGGGAA    300

ATCAGGGCTC CTTCTTAACT AAAGGTCCAT CCAAGCTGAA TGATCGCGCT GACTCAAGAA    360

GAAGCCTTTG GGACCAAGGA AACTTCCCCC TGATCATCAA GAATCTTAAG ATAGAAGACT    420

CAGATACTTA CATCTGTGAA GTGGAGGACC AGAAGGAGGA GGTGCAATTG CTAGTGTTCG    480

GATTGACTGC CAACTCTGAC ACCCACCTGC TTCAGGGGCA GAGCCTGACC CTGACCTTGG    540

AGAGCCCCCC TGGTAGTAGC CCCTCAGTGC AATGTAGGAG TCCAAGGGGT AAAAACATAC    600

AGGGGGGGAA GACCCTCTCC GTGTCTCAGC TGGAGCTCCA GGATAGTGGC ACCTGGACAT    660

GCACTGTCTT GCAGAACCAG AAGAAGGTGG AGTTCAAAAT AGACATCGTG GTGCTAGCTT    720

TCCAGAAGGC CTCCAGCATA GTCTATAAGA AGAGGGGGA ACAGGTGGAG TTCTCCTTCC     780

CACTCGCCTT TACAGTTGAA AAGCTGACGG GCAGTGGCGA GCTGTGGTGG CAGGCGGAGA    840

GGGCTTCCTC CTCCAAGTCT TGGATCACCT TTGACCTGAA GAACAAGGAA GTGTCTGTAA    900

AACGGGTTAC CCAGGACCCT AAGCTCCAGA TGGGCAAGAA GCTCCCGCTC CACCTCACCC    960

TGCCCCAGGC CTTGCCTCAG TATGCTGGCT CTGGAAACCT CACCCTGGCC CTTGAAGCGA   1020

AAACAGGAAA GTTGCATCAG GAAGTGAACC TGGTGGTGAT GAGAGCCACT CAGCTCCAGA   1080

AAAATTTGAC CTGTGAGGTG TGGGGACCCA CCTCCCCTAA GCTGATGCTG AGCTTGAAAC   1140

TGGAGAACAA GGAGGCAAAG GTCTCGAAGC GGGAGAAGCC GGTGTGGGTG CTGAACCCTG   1200

AGGCGGGGAT GTGGCAGTGT CTGCTGAGTG ACTCGGGACA GGTCCTGCTG GAATCCAACA   1260

TCAAGGTTCT GCCCACATGG TCCACCCCGG TGCACGCGGA TCCC                    1304
```

(2) INFORMATION FOR SEQ ID NO:29:

(i) SEQUENCE CHARACTERISTICS:
        (A) LENGTH: 398 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:29:

```
Met Asn Arg Gly Val Pro Phe Arg His Leu Leu Val Leu Gln Leu
 1               5                  10                  15

Ala Leu Leu Pro Ala Ala Thr Gln Gly Asn Lys Val Val Leu Gly Lys
                20                  25                  30

Lys Gly Asp Thr Val Glu Leu Thr Cys Thr Ala Ser Gln Lys Lys Ser
                35                  40                  45

Ile Gln Phe His Trp Lys Asn Ser Asn Gln Ile Lys Ile Leu Gly Asn
                50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
```

|                | 115 |                |     | 120 |                |     |     | 125 |                |     |
|---|---|---|---|---|---|---|---|---|---|---|

Ser Asp Thr His Leu Leu Gln Gly Gln Ser Leu Thr Leu Thr Leu Glu
130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Leu Ala Phe Gln Lys Ala Ser
            195                 200                 205

Ser Ile Val Tyr Lys Lys Glu Gly Glu Gln Val Glu Phe Ser Phe Pro
210                 215                 220

Leu Ala Phe Thr Val Glu Lys Leu Thr Gly Ser Gly Glu Leu Trp Trp
225                 230                 235                 240

Gln Ala Glu Arg Ala Ser Ser Lys Ser Trp Ile Thr Phe Asp Leu
                245                 250                 255

Lys Asn Lys Glu Val Ser Val Lys Arg Val Thr Gln Asp Pro Lys Leu
                260                 265                 270

Gln Met Gly Lys Lys Leu Pro Leu His Leu Thr Leu Pro Gln Ala Leu
            275                 280                 285

Pro Gln Tyr Ala Gly Ser Gly Asn Leu Thr Leu Ala Leu Glu Ala Lys
290                 295                 300

Thr Gly Lys Leu His Gln Glu Val Asn Leu Val Val Met Arg Ala Thr
305                 310                 315                 320

Gln Leu Gln Lys Asn Leu Thr Cys Glu Val Trp Gly Pro Thr Ser Pro
                325                 330                 335

Lys Leu Met Leu Ser Leu Lys Leu Glu Asn Lys Glu Ala Lys Val Ser
                340                 345                 350

Lys Arg Glu Lys Pro Val Trp Val Leu Asn Pro Glu Ala Gly Met Trp
            355                 360                 365

Gln Cys Leu Leu Ser Asp Ser Gly Gln Val Leu Leu Glu Ser Asn Ile
            370                 375                 380

Lys Val Leu Pro Thr Trp Ser Thr Pro Val His Ala Asp Pro
385                 390                 395

(2) INFORMATION FOR SEQ ID NO:30:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

```
GCCTGTTTGA AAGCAGCGG GCAAGAAAGA CGCAAGCCCA GAGGCCCTGC CATTTCTGTG      60

GGCTCAGGTC CCTACTGGCT CAGGCCCCTG CCTCCCTCGG CAAGGCCACA ATGAACCGGG     120

GAGTCCCTTT TAGGCACTTG CTTCTGGTGC TGCAACTGGC GCTCCTCCCA GCAGCCACTC    180

AGGGAAACAA AGTGGTGCTG GGCAAAAAAG GGGATACAGT GGAACTGACC TGTACAGCTT    240

CCCAGAAGAA GAGCATACAA TTCCACTGGA AAAACTCCAA CCAGATAAAG ATTCTGGGAA    300

ATCAGGGCTC CTTCTTAACT AAAGGTCCAT CCAAGCTGAA TGATCGCGCT GACTCAAGAA    360

GAAGCCTTTG GGACCAAGGA AACTTCCCCC TGATCATCAA GAATCTTAAG ATAGAAGACT    420
```

```
CAGATACTTA CATCTGTGAA GTGGAGGACC AGAAGGAGGA GGTGCAATTG CTAGTGTTCG       480

GATTGACTGC CAACTCTGAC ACCCACCTGC TTCAGGGGCA GAGCCTGACC CTGACCTTGG       540

AGAGCCCCCC TGGTAGTAGC CCCTCAGTGC AATGTAGGAG TCCAAGGGGT AAAAACATAC      600

AGGGGGGGAA GACCCTCTCC GTGTCTCAGC TGGAGCTCCA GGATAGTGGC ACCTGGACAT      660

GCACTGTCTT GCAGAACCAG AAGAAGGTGG AGTTCAAAAT AGACATCGTG GTGCTAGCT      719
```

(2) INFORMATION FOR SEQ ID NO:31:

(i) SEQUENCE CHARACTERISTICS:
        (A) LENGTH: 203 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:31:

```
Met Asn Arg Gly Val Pro Phe Arg His Leu Leu Leu Val Leu Gln Leu
 1               5                   10                  15

Ala Leu Leu Pro Ala Ala Thr Gln Gly Asn Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala
        195                 200
```

(2) INFORMATION FOR SEQ ID NO:32:

(i) SEQUENCE CHARACTERISTICS:
        (A) LENGTH: 768 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

```
GCTAGCAGAG CCCAAATCTT GTGACAAAAC TCACACATGC CCACCGTGCC CAGCACCTGA       60

ACTCCTGGGG GGACCGTCAG TCTTCCTCTT CCCCCCAAAA CCCAAGGACA CCCTCATGAT      120
```

```
CTCCCGGACC CCTGAGGTCA CATGCGTGGT GGTGGACGTG AGCCACGAAG ACCCTGAGGT      180

CAAGTTCAAC TGGTACGTGG ACGGCGTGGA GGTGCATAAT GCCAAGACAA AGCCGCGGGA      240

GGAGCAGTAC AACAGCACGT ACCGGGTGGT CAGCGTCCTC ACCGTCCTGC ACCAGGACTG      300

GCTGAATGGC AAGGAGTACA AGTGCAAGGT CTCCAACAAA GCCCTCCCAG CCCCCATCGA      360

GAAAACCATC TCCAAAGCCA AGGGCAGCC CCGAGAACCA CAGGTGTACA CCCTGCCCCC       420

ATCCCGGGAT GAGCTGACCA AGAACCAGGT CAGCCTGACC TGCCTGGTCA AAGGCTTCTA      480

TCCCAGCGAC ATCGCCGTGG AGTGGGAGAG CAATGGGCAG CCGGAGAACA ACTACAAGAC      540

CACGCCTCCC GTGCTGGACT CCGACGGCTC CTTCTTCCTC TACAGCAAGC TCACCGTGGA      600

CAAGAGCAGG TGGCAGCAGG GGAACGTCTT CTCATGCTCC GTGATGCATG AGGCTCTGCA      660

CAACCACTAC ACGCAGAAGA GCCTCTCCCT GTCTCCGGGG CTGCAACTGG ACGAGACCTG      720

TGCTGAGGCC CAGGACGGGG AGCTGGACGG GCTCTGGACG ACGGATCC                   768
```

(2) INFORMATION FOR SEQ ID NO:33:

(i) SEQUENCE CHARACTERISTICS:
        (A) LENGTH: 254 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:33:

```
Glu Pro Lys Ser Cys Asp Lys Thr His Thr Cys Pro Pro Cys Pro Ala
 1               5                  10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
           100                 105                 110

Leu Pro Ala Pro Ile Glu Lys Thr Ile Ser Lys Ala Lys Gly Gln Pro
       115                 120                 125

Arg Glu Pro Gln Val Tyr Thr Leu Pro Pro Ser Arg Asp Glu Leu Thr
   130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Leu Gln Leu Asp Glu Thr Cys Ala Glu
```

```
225                 230                 235                 240
Ala Gln Asp Gly Glu Leu Asp Gly Leu Trp Thr Thr Asp Pro
                245                 250
```

(2) INFORMATION FOR SEQ ID NO:34:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
CCAAGGGCCT CTGCCCTCCC TGCCCCACCG ACAGGCTCCG CCCTCCCTGA CCCGCAGACA    60

GCCTCTGCCC TCCCTGACCC GCCAGCAGCC TCTGCCCTCC CTGCGGCCCT GGCGGTGATC   120

TCCTTCCTCC TCGGGCTGGG CCTGGGGGTG GCGTGTGTGC TGGCGAGGAC GCGT         174
```

(2) INFORMATION FOR SEQ ID NO:35:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:35:

```
Pro Arg Ala Ser Ala Leu Pro Ala Pro Pro Thr Gly Ser Ala Leu Pro
1               5                   10                  15

Asp Pro Gln Thr Ala Ser Ala Leu Pro Asp Pro Pro Ala Ala Ser Ala
                20                  25                  30

Leu Pro Ala Ala Leu Ala Val Ile Ser Phe Leu Leu Gly Leu Gly Leu
            35                  40                  45

Gly Val Ala Cys Val Leu Ala Arg Thr Arg
        50                  55
```

(2) INFORMATION FOR SEQ ID NO:36:

(i) SEQUENCE CHARACTERISTICS:
        (A) LENGTH: 345 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
ACGCGTTTCA GCAGGAGCGC AGAGCCCCCC GCGTACCAGC AGGGCCAGAA CCAGCTCTAT    60

AACGAGCTCA ATCTAGGACG AAGAGAGGAG TACGATGTTT TGGACAAGAG ACGTGGCCGG   120

GACCCTGAGA TGGGGGGAAA GCCGAGAAGG AAGAACCCTC AGGAAGGCCT GTACAATGAA   180

CTGCAGAAAG ATAAGATGGC GGAGGCCTAC AGTGAGATTG GGATGAAAGG CGAGCGCCGG   240

AGGGGCAAGG GCACGATGG CCTTTACCAG GGTCTCAGTA CAGCCACCAA GGACACCTAC   300

GACGCCCTTC ACATGCAGGC CCTGCCCCCT CGCTAAAGCG GCCGC                   345
```

(2) INFORMATION FOR SEQ ID NO:37:

(i) SEQUENCE CHARACTERISTICS:
        (A) LENGTH: 111 amino acids (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:37:

Thr Arg Phe Ser Arg Ser Ala Glu Pro Pro Ala Tyr Gln Gln Gly Gln
1               5                   10                  15

Asn Gln Leu Tyr Asn Glu Leu Asn Leu Gly Arg Arg Glu Glu Tyr Asp
            20                  25                  30

Val Leu Asp Lys Arg Arg Gly Arg Asp Pro Glu Met Gly Gly Lys Pro
        35                  40                  45

Arg Arg Lys Asn Pro Gln Glu Gly Leu Tyr Asn Glu Leu Gln Lys Asp
50                  55                  60

Lys Met Ala Glu Ala Tyr Ser Glu Ile Gly Met Lys Gly Glu Arg Arg
65                  70                  75                  80

Arg Gly Lys Gly His Asp Gly Leu Tyr Gln Gly Leu Ser Thr Ala Thr
                85                  90                  95

Lys Asp Thr Tyr Asp Ala Leu His Met Gln Ala Leu Pro Pro Arg
            100                 105                 110

(2) INFORMATION FOR SEQ ID NO:38:

(i) SEQUENCE CHARACTERISTICS:
        (A) LENGTH: 16 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:38:

Gln Ser Phe Gly Leu Leu Asp Pro Lys Leu Cys Tyr Leu Leu Asp Gly
1               5                   10                  15

(2) INFORMATION FOR SEQ ID NO:39:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:39:

Pro Thr Trp Ser Thr Pro Val His Ala Asp Pro Lys Leu Cys Tyr Leu
1               5                   10                  15

Leu Asp Gly (2) INFORMATION FOR SEQ ID NO:40:

(i) SEQUENCE CHARACTERISTICS:
        (A) LENGTH: 12 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:40:

Leu Gly Glu Pro Gln Leu Cys Tyr Ile Leu Asp Ala
1               5                   10

(2) INFORMATION FOR SEQ ID NO:41:

(i) SEQUENCE CHARACTERISTICS:
        (A) LENGTH: 19 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:41:

```
Pro Thr Trp Ser Thr Pro Val His Ala Asp Pro Gln Leu Cys Tyr Ile
 1               5                  10                  15

Leu Asp Ala
```

(2) INFORMATION FOR SEQ ID NO:42:

(i) SEQUENCE CHARACTERISTICS:
        (A) LENGTH: 16 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:42:

```
Gln Ser Phe Gly Leu Leu Asp Pro Lys Leu Cys Tyr Leu Leu Asp Gly
 1               5                  10                  15
```

(2) INFORMATION FOR SEQ ID NO:43:

(i) SEQUENCE CHARACTERISTICS:
        (A) LENGTH: 16 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:43:

```
Phe Ser Pro Pro Gly Ala Asp Pro Lys Leu Cys Tyr Leu Leu Asp Gly
 1               5                  10                  15
```

(2) INFORMATION FOR SEQ ID NO:44:

(i) SEQUENCE CHARACTERISTICS:
        (A) LENGTH: 142 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:44:

```
Gln Ser Phe Gly Leu Leu Asp Pro Lys Leu Cys Tyr Leu Leu Asp Gly
 1               5                  10                  15

Ile Leu Phe Ile Tyr Gly Val Ile Leu Thr Ala Leu Phe Leu Arg Val
                20                  25                  30

Lys Phe Ser Arg Ser Ala Glu Pro Pro Ala Tyr Gln Gln Gly Gln Asn
                35                  40                  45

Gln Leu Tyr Asn Glu Leu Asn Leu Gly Arg Arg Glu Glu Tyr Asp Val
        50                  55                  60

Leu Asp Lys Arg Arg Gly Arg Asp Pro Glu Met Gly Gly Lys Pro Arg
 65                  70                  75                  80

Arg Lys Asn Pro Gln Glu Gly Leu Tyr Asn Glu Leu Gln Lys Asp Lys
                85                  90                  95
```

```
Met Ala Glu Ala Tyr Ser Glu Ile Gly Met Lys Gly Glu Arg Arg Arg
            100                 105                 110

Gly Lys Gly His Asp Gly Leu Tyr Gln Gly Leu Ser Thr Ala Thr Lys
        115                 120                 125

Asp Thr Tyr Asp Ala Leu His Met Gln Ala Leu Pro Pro Arg
    130                 135                 140
```

(2) INFORMATION FOR SEQ ID NO:45:

(i) SEQUENCE CHARACTERISTICS:
        (A) LENGTH: 35 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:45:

```
Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu
        35
```

(2) INFORMATION FOR SEQ ID NO:46:

(i) SEQUENCE CHARACTERISTICS:
        (A) LENGTH: 32 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:46:

```
Lys Lys Leu Val Lys Lys Phe Arg Gln Lys Lys Gln Arg Gln Asn Gln
1               5                   10                  15

Leu Tyr Asn Glu Leu Asn Leu Gly Arg Arg Glu Glu Tyr Asp Val Leu
            20                  25                  30
```

(2) INFORMATION FOR SEQ ID NO:47:

(i) SEQUENCE CHARACTERISTICS:
        (A) LENGTH: 35 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:47:

```
Arg Thr Gln Ile Lys Lys Leu Cys Ser Trp Arg Asp Lys Asn Ser Ala
1               5                   10                  15

Ala Asn Gln Leu Tyr Asn Glu Leu Asn Leu Gly Arg Arg Glu Glu Tyr
            20                  25                  30

Asp Val Leu
        35
```

(2) INFORMATION FOR SEQ ID NO:48:

(i) SEQUENCE CHARACTERISTICS:
        (A) LENGTH: 35 amino acids
        (B) TYPE: amino acid (C) STRANDEDNESS: unknown
            (D) TOPOLOGY: linear (ii) MOLECULE TYPE: protein (xi) SEQUENCE DESCRIPTION: SEQ ID NO:48:

Arg Thr Arg Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu
        35

(2) INFORMATION FOR SEQ ID NO:49:

(i) SEQUENCE CHARACTERISTICS:
            (A) LENGTH: 36 amino acids
            (B) TYPE: amino acid
            (C) STRANDEDNESS: unknown
            (D) TOPOLOGY: linear (ii) MOLECULE TYPE: protein (xi) SEQUENCE DESCRIPTION: SEQ ID NO:49:

Arg Thr Arg Asp Pro Glu Met Gly Gly Lys Pro Arg Arg Lys Asn Pro
1               5                   10                  15

Gln Glu Gly Leu Tyr Asn Glu Leu Gln Lys Asp Lys Met Ala Glu Ala
            20                  25                  30

Tyr Ser Glu Ile
        35

(2) INFORMATION FOR SEQ ID NO:50:

(i) SEQUENCE CHARACTERISTICS:
            (A) LENGTH: 38 amino acids
            (B) TYPE: amino acid
            (C) STRANDEDNESS: unknown
            (D) TOPOLOGY: linear (ii) MOLECULE TYPE: protein (xi) SEQUENCE DESCRIPTION: SEQ ID NO:50:

Arg Thr Arg Ile Gly Met Lys Gly Glu Arg Arg Arg Gly Lys Gly His
1               5                   10                  15

Asp Gly Leu Tyr Gln Gly Leu Ser Thr Ala Thr Lys Asp Thr Tyr Asp
            20                  25                  30

Ala Leu His Met Gln Ala
        35

(2) INFORMATION FOR SEQ ID NO:51:

(i) SEQUENCE CHARACTERISTICS:
            (A) LENGTH: 63 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:51:

GGATCCCAAG GCCAGGCTAA AGCCGAAGCC GCGAAGGCCG AGGCTAAGGC CGAAGCAGAT    60

CTG    63

(2) INFORMATION FOR SEQ ID NO:52:

-continued

```
    (i) SEQUENCE CHARACTERISTICS:
        (A) LENGTH: 20 amino acids
        (B) TYPE: amino acid
        (C) STRANDEDNESS: unknown
        (D) TOPOLOGY: linear (ii) MOLECULE TYPE: protein (xi) SEQUENCE DESCRIPTION: SEQ ID NO:52:

Asp Pro Lys Ala Glu Ala Lys Ala Glu Ala Lys Ala Glu Ala Lys Ala
1               5                  10                  15

Glu Ala Asp Leu
            20

(2) INFORMATION FOR SEQ ID NO:53:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:53:

Arg Lys Lys Arg Ile Ser Ala Asn Ser Thr Asp Pro Val Lys Ala Ala
1               5                  10                  15

Gln Phe Glu Pro Pro Gly Arg Gln Met Ile Ala Ile Arg Lys Arg Gln
            20                  25                  30

Leu Glu Glu Thr Asn Asn Asp Tyr Glu Thr Ala Asp Gly Gly Tyr Met
        35                  40                  45

Thr Leu Asn Pro Arg Ala Pro Thr Asp Asp Asp Lys Asn Ile Tyr Leu
    50                  55                  60

Thr Leu Pro Pro Asn Asp His Val Asn Ser Asn Asn
65                  70                  75
```